(12) United States Patent
Graupe et al.

(10) Patent No.: US 8,518,874 B2
(45) Date of Patent: *Aug. 27, 2013

(54) HCV INHIBITORS

(75) Inventors: Michael Graupe, Pacifica, CA (US);
John O. Link, San Francisco, CA (US);
Chandrasekar Venkataramani,
Redwood City, CA (US)

(73) Assignee: Virobay, Inc., Menlo Park, CA (US)

( * ) Notice: Subject to any disclaimer, the term of this patent is extended or adjusted under 35 U.S.C. 154(b) by 231 days.

This patent is subject to a terminal disclaimer.

(21) Appl. No.: 12/605,271

(22) Filed: Oct. 23, 2009

(65) Prior Publication Data

US 2010/0266537 A1   Oct. 21, 2010

Related U.S. Application Data

(63) Continuation of application No. 11/478,337, filed on Jun. 28, 2006, now Pat. No. 7,608,592.

(60) Provisional application No. 60/695,767, filed on Jun. 30, 2005.

(51) Int. Cl.

| *A61K 38/05* | (2006.01) |
| *A61K 38/06* | (2006.01) |
| *C07K 5/06*  | (2006.01) |
| *C07K 5/08*  | (2006.01) |

(52) U.S. Cl.
USPC ........ 514/4.3; 514/21.9; 514/21.91; 530/331; 548/517; 548/518; 548/519; 548/525; 548/526; 548/527

(58) Field of Classification Search
None
See application file for complete search history.

(56) References Cited

U.S. PATENT DOCUMENTS

| 6,268,207 B1 | 7/2001 | Bailey |
| 6,404,397 B1 | 6/2002 | Grinberg et al. |
| 6,492,383 B1 | 12/2002 | Munchhof et al. |
| 6,608,027 B1 | 8/2003 | Tsantrizos et al. |
| 6,774,212 B2 | 8/2004 | Han |
| 6,846,806 B2 | 1/2005 | Priestly |
| 6,939,854 B2 | 9/2005 | Priestly |
| 7,399,749 B2 * | 7/2008 | Arasappan et al. .......... 424/85.4 |
| 7,608,592 B2 * | 10/2009 | Graupe et al. ................. 514/1.1 |
| 2003/0216325 A1 * | 11/2003 | Saksena et al. ................. 514/18 |
| 2005/0137139 A1 | 6/2005 | Perni et al. |
| 2005/0267043 A1 | 12/2005 | Bogen et al. |
| 2006/0142204 A1 | 6/2006 | Halfon et al. |
| 2009/0304631 A1 * | 12/2009 | Campbell et al. ............ 424/85.7 |

FOREIGN PATENT DOCUMENTS

| EP | 1 136 498 A1 | 9/2001 |
| EP | 1 437 362 A | 7/2004 |
| WO | WO 99/24440 A1 | 5/1999 |
| WO | WO 00/09543 A2 | 2/2000 |
| WO | WO 00/09543 A3 | 2/2000 |
| WO | WO 2000/009543 A2 | 2/2000 |
| WO | WO 00/59929 A1 | 10/2000 |
| WO | WO 02/18369 A2 | 3/2002 |
| WO | WO 02/18369 A3 | 3/2002 |
| WO | WO 2004/103996 A1 | 1/2004 |
| WO | WO 2004/093798 A | 11/2004 |
| WO | WO 2005/028501 A1 | 3/2005 |
| WO | WO 2005/035525 A2 | 4/2005 |
| WO | WO 2005/035525 A3 | 4/2005 |
| WO | WO 2005/070955 A | 9/2005 |
| WO | WO 2006/043145 A | 4/2006 |

OTHER PUBLICATIONS

Malancona et al. SAR and parmacokinetic studies on phenethylamide inhibitors . . . Bioorganic & Medicinal Chemistry Letters. 2004, vol. 14, pp. 4575-4579.*

Ronn et al. Exploration of acyl sulfonates as carboxylic acid replacements . . . Bioorganic & Medicinal Chemistry. 2006, vol. 14, pp. 544-559.*

U.S. Appl. No. 11/866,836, filed Oct. 3, 2007, Link, John, et al.
U.S. Appl. No. 11/968,475, filed Jan. 2, 2008, Green, et al.
Supplementary European Search Report mailed on Jun. 12, 2009, for EP Application No. 06774467.2, 6 pages.

* cited by examiner

*Primary Examiner* — Jeffrey E. Russel
(74) *Attorney, Agent, or Firm* — Kilpatrick Townsend & Stockton LLP

(57) ABSTRACT

The present invention is directed to compounds that are antiviral agents. Specifically the compounds of the present invention inhibit replication of HCV and are therefore useful in treating hepatitis C infections. The present invention is also directed to pharmaceutical compositions comprising these compounds and processes for preparing them.

28 Claims, No Drawings

HCV INHIBITORS

CROSS-REFERENCES TO RELATED APPLICATIONS

This application is a Continuation of U.S. patent application Ser. No. 11/478,337, filed Jun. 28, 2006 now U.S. Pat. No. 7,608,592, which claims the benefit of U.S. Provisional application Ser. No. 60/695,767 filed Jun. 30, 2005, the disclosures of both of which are incorporated herein by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

1. Field of the Invention

The present invention is directed to compounds that inhibit HCV replication and are therefore useful in treating hepatitis C. The present invention is also directed to pharmaceutical compositions comprising these compounds and processes for preparing them.

2. State of the Art

Hepatitis C virus (HCV) is a (+)-sense single-standed RNA virus that is a major cause of non-A, non-B hepatitis worldwide. A large percentage of people infected with HCV develop chronic liver disease. This chronic hepatitis C infection, in turn, makes them at high risk for developing serious liver diseases such as liver cirrhosis, hepatocellular carcinoma and terminal liver disease leading to death. Currently, hepatitits C infections are treated with either injectable interferon or with pegylated forms of interferon such as PEG-Intron® and Pegasys®, alone or in combination with Ribavirin. These therapies, however, induce severe side effects such as retinopathy, thyroiditis, acute pancreatitis, depression. Therefore, there is a need for safe, oral drug for the treatment of hepatitis C infections. The present invention fulfils this and related needs.

BRIEF SUMMARY OF THE INVENTION

In one aspect, this invention is directed to a compound of Formula (I):

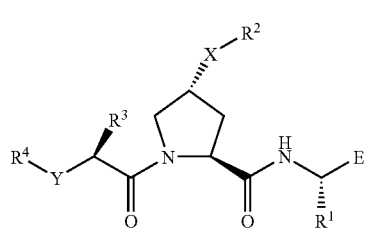

(I)

where:

E is —COCONR$^5$R$^6$, —COCF$_2$CONR$^5$R$^6$, —COCF$_2$C(O)OR$^5$, —COCOR$^7$, —COCF$_2$R$^8$, —COR$^9$, —COCOOR$^{10}$, —CONR$^{11}$R$^{12}$, or —B(OR$^{13}$)$_2$ where R$^5$, R$^6$, R$^7$, R$^9$, R$^{10}$, R$^{11}$, R$^{12}$ and each R$^{13}$ is independently selected from hydrogen, alkyl, alkenyl, alkynyl, cycloalkyl, cycloalkylalkyl, aryl, aralkyl, heteroaryl, heteroaralkyl, heterocyclyl, or heterocyclylalkyl and R$^8$ is halo, alkyl, alkenyl, alkynyl, cycloalkyl, cycloalkylalkyl, aryl, aralkyl, heteroaryl, heteroaralkyl, heterocyclyl, or heterocyclylalkyl wherein the aliphatic, alicyclic and aromatic groups in E are optionally substituted with one, two, or three R$^a$ independently selected from hydroxy, alkoxy, haloalkoxy, aryloxy, heteroaryloxy, alkylthio, arylthio, heteroarylthio, amino, monosubstituted amino, disubstituted amino, alkylsulfonyl, arylsulfonyl, carboxy, alkoxycarbonyl, alkenyloxycarbonyl, alkynyloxycarbonyl, alkenylaminocarbonyl, acylamino, aminocarbonyl, halo, or cyano and further wherein the aromatic or alicyclic ring in R$^a$ is optionally substituted with one, two, or three substituents independently selected from alkyl, alkoxy, halo, haloalkyl, haloalkoxy, carboxy, or carboxyalkyl; and optionally, R$^5$ and R$^6$, and R$^{11}$ and R$^{12}$ can be combined with the nitrogen to which they are attached to form a five- to seven-membered ring;

R$^1$ is alkyl, haloalkyl, alkenyl, alkynyl, cycloalkyl, cycloalkylalkyl, aryl, aralkyl, heteroaryl, heteroaralkyl, heterocyclyl or heterocyclylalkyl wherein the aliphatic, alicyclic and aromatic groups in R$^1$ are optionally substituted with one or two R$^b$ independently selected from hydroxy, alkoxy, aryloxy, heteroaryloxy, alkylthio, arylthio, heteroarylthio, amino, monosubstituted amino, disubstituted amino, alkylsulfonyl, arylsulfonyl, carboxy, alkoxycarbonyl, acylamino, aminocarbonyl, halo, or cyano and further wherein the aromatic or alicyclic ring in R$^b$ is optionally substituted with one, two, or three substituents independently selected from alkyl, alkoxy, halo, haloalkyl, haloalkoxy, cyano, carboxy, or carboxyalkyl;

X is —O—, —NR$^{14}$, —S—, —SO—, or —SO$_2$—;

R$^3$ is alkyl, haloalkyl, alkenyl, alkynyl, cycloalkyl, cycloalkylalkyl, aryl, aralkyl, heteroaryl, heteroaralkyl, heterocyclyl or heterocyclylalkyl wherein the aliphatic, alicyclic and aromatic groups in R$^3$ are optionally substituted with one or two R$^c$ independently selected from hydroxy, alkoxy, haloalkoxy, aryloxy, heteroaryloxy, alkylthio, arylthio, heteroarylthio, amino, monosubstituted amino, disubstituted amino, alkylsulfonyl, arylsulfonyl, carboxy, alkoxycarbonyl, acylamino, aminocarbonyl, halo, or cyano and further wherein the aromatic or alicyclic ring in R$^c$ is optionally substituted with one, two, or three substituents independently selected from alkyl, alkoxy, halo, haloalkyl, haloalkoxy, carboxy, or carboxyalkyl;

Y is —C(O)NH—, —OC(O)NH—, —NR$^{14}$C(O)NH—, or —NR$^{14}$C(O)O—. For each of X and Y, each R$^{14}$ when present is independently selected from hydrogen, alkyl optionally substituted with halo, hydroxy, alkoxy, amino, monosubstituted amino, disubstituted amino and aryl, heteroaryl or heterocyclyl, each of which is optionally substituted with halo and alkyl;

R$^2$ is heteroaryl or —CO-(fused heterocyclyl) ring wherein the heteroaryl and fused heterocyclyl rings are optionally substituted with one, two, three, or four R$^d$ independently selected from hydrogen, alkyl, cycloalkyl, alkenyl, alkynyl, alkylthio, hydroxy, alkoxy, halo, haloalkyl, haloalkoxy, carboxy, carboxyalkyl, hydroxyalkyl, alkoxyalkyl, aminoalkyl, alkylsulfonyl, alkylcarbonyl, aryl, aralkyl, arylsulfonyl, arylcarbonyl, aryloxycarbonyl, aminosulfonyl, aminocarbonyl, heteroaryl, heteroaralkyl, heteroarylsulfonyl, heteroarylcarbonyl, heteroaryloxycarbonyl, heterocyclyl, heterocyclylalkyl, heterocyclylsulfonyl, heterocyclylcarbonyl, heterocyclyloxycarbonyl, amino, monosubstituted amino, or disubstituted amino or when two $R^d$ are on adjacent carbon atoms they together with the carbon atoms to which they are attached form a four, five or six membered heterocyclyl ring containing one or two heteroatoms selected from nitrogen, oxygen, sulfur, or —$SO_2$— wherein the heterocyclyl ring is optionally substituted with one or two alkyl; and further wherein the aromatic or alicyclic ring in $R^d$ is optionally substituted with one, two, or three $R^e$ independently selected from alkyl, alkylcarbonylamino, alkoxycarbonylamino, cycloalkyl, cycloalkylalkyl, cycloalkoxycarbonylamino, cycloalkylalkyloxycarbonylamino, nitro, alkoxy, cycloalkyloxy, aryloxy, heteroaryloxy, halo, haloalkyl, haloalkoxy, hydroxyl, carboxy, alkoxycarbonyl, amino, monosubstituted amino, disubstituted amino, acylamino, or ureido wherein cycloalkyl and cycloalkylalkyl in $R^e$ are optionally substituted with one, two or three alkyl; and $R^4$ is:
(i) alkyl provided that Y is —OC(O)NH—, —$NR^{14}$—C(O)NH—, or —$NR^{14}$C(O)O— and when $R^2$ is heteroaryl then at least one of $R^d$ is not hydrogen;
(ii) cycloalkyl, cycloalkylalkyl, aryl, aralkyl, heteroaryl, heteroaralkyl, heterocyclyl, or heterocyclylalkyl provided that the heteroaryl and fused heterocyclyl ring in $R^2$ are substituted with at least a heteroaryl ring; or
(iii) alkyl provided that when Y is —C(O)NH— or —$SO_2$NH— then the heteroaryl and fused heterocyclyl rings in $R^2$ are substituted with at least a heteroaryl ring;

wherein the aromatic or alicyclic ring in $R^4$ is optionally substituted with one, two, or three $R^f$ independently selected from alkyl, alkoxy, halo, haloalkyl, haloalkoxy, cyano, carboxy, carboxyalkyl, hydroxyalkyl, alkoxyalkyl, aminoalkyl, alkylsulfonyl, alkylcarbonyl, aryl, aralkyl, arylsulfonyl, arylcarbonyl, aryloxycarbonyl, aminosulfonyl, aminocarbonyl, heteroaryl, heteroaralkyl, heteroarylsulfonyl, heteroarylcarbonyl, heteroaryloxycarbonyl, heterocyclyl, heterocyclylalkyl, heterocyclylsulfonyl, heterocyclylcarbonyl, heterocyclyloxycarbonyl, monosubstituted amino, or disubstituted amino wherein the aromatic or alicyclic ring in $R^f$ is optionally substituted with one, two, or three substituents independently selected from alkyl, alkoxy, halo, haloalkyl, haloalkoxy, hydroxy, carboxy, alkoxycarbonyl, monosubstituted amino, disubstituted amino, or acylamino; or a pharmaceutically acceptable salts thereof.

For the sake of clarity, it is pointed out that the point of attachment of the Y groups to the $R^4$ group as follows: $R^4$C(O)NH—, $R^4$OC(O)NH—, $R^4NR^{14}$—C(O)NH—, or $R^4NR^{14}$C(O)O—.

In a second aspect, this invention is directed to a pharmaceutical composition comprising a compound of Formula (I) or a pharmaceutically acceptable salt thereof in admixture with one or more pharmaceutically acceptable excipient.

In a third aspect, this invention is directed to a method for treating hepatitis C in an animal which method comprises administering to the animal a pharmaceutical composition comprising a therapeutically effective amount of a compound of Formula (I) or a pharmaceutically acceptable salt thereof in admixture with one or more pharmaceutically acceptable excipient.

In a fourth aspect, this invention is directed to processes for preparing compounds of Formula (I).

BRIEF DESCRIPTION OF THE DRAWINGS

Not applicable

DETAILED DESCRIPTION OF THE INVENTION

Definitions

Unless otherwise stated, the following terms used in the specification and claims are defined for the purposes of this Application and have the following meanings.

"Alicyclic" means a moiety characterized by arrangement of the carbon atoms in closed non-aromatic ring structures e.g., cycloalkyl and heterocyclyl rings as defined herein.

"Aliphatic" means alkyl, alkenyl, or alkynyl radicals as defined herein

"Alkyl" represented by itself means a straight or branched, saturated aliphatic radical containing one to eight carbon atoms, unless otherwise indicated e.g., alkyl includes methyl, ethyl, propyl, isopropyl, butyl, sec-butyl, isobutyl, tert-butyl, and the like.

"Alkylcarbonylamino" refers to a —NHC(O)R radical where R is an alkyl group as defined above e.g., methylcarbonylamino, ethylcarbonylamino, and the like.

"Alkylene", unless indicated otherwise, means a straight or branched, saturated aliphatic, divalent radical having the number of one to six carbon atoms, e.g., methylene (—$CH_2$—), ethylene (—$CH_2CH_2$—), trimethylene (—$CH_2CH_2CH_2$—), tetramethylene (—$CH_2CH_2CH_2CH_2$—) 2-methyltetramethylene (—$CH_2CH(CH_3)CH_2CH_2$—), pentamethylene (—$CH_2CH_2CH_2CH_2CH_2$—), and the like.

"Alkenyl" means a linear monovalent hydrocarbon radical of two to six carbon atoms or a branched monovalent hydrocarbon radical of three to six carbon atoms containing one or two double bonds e.g., ethenyl, propenyl (including all isomeric forms), 1-methylpropenyl, butenyl (including all isomeric forms), or pentenyl (including all isomeric forms), and the like.

"Alkenyloxycarbonyl" refers to a —C(O)OR radical where R is an alkenyl group as defined above e.g., 3-propen-1-yloxycarbonyl, and the like.

"Alkenylaminocarbonyl" refers to a —C(O)NHR radical where R is an alkenyl group as defined above e.g., 3-propen-1-ylaminocarbonyl, and the like.

"Alkynyl" means a linear monovalent hydrocarbon radical of two to six carbon atoms or a branched monovalent hydrocarbon radical of three to six carbon atoms containing one or two triple bonds e.g., ethynyl, propynyl (including all isomeric forms), 1-methylpropynyl, butynyl (including all isomeric forms), or pentynyl (including all isomeric forms), and the like.

"Alkynyloxycarbonyl" refers to a —C(O)OR radical where R is an alkynyl group as defined above e.g., 3-propyn-1-yloxycarbonyl, and the like.

"Alkylthio" means an —SR radical where R is alkyl as defined herein, e.g., methylthio, ethylthio, propylthio, or butylthio, and the like.

"Alkylsulfonyl" means —$SO_2$R radical where R is alkyl as defined herein e.g., methylsulfonyl, ethylsulfonyl, and the like.

"Alkoxy" refers to a —OR radical where R is an alkyl group as defined above e.g., methoxy, ethoxy, and the like.

"Alkoxycarbonylamino" refers to a —NHC(O)OR radical where R is an alkyl group as defined above e.g., methoxycarbonylamino, ethoxycarbonylamino, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxy-ethyl, 1-, 2-, or 3-methoxypropyl, 2-ethoxyethyl, and the like.

"Alkoxycarbonyl" refers to a —C(O)OR radical where R is an alkyl group as defined above e.g., methoxycarbonyl, ethoxycarbonyl, and the like.

"Amino" means a —NH$_2$ radical.

"Alkylamino" means a radical —NHR where R is alkyl as defined herein, e.g., methylamino, ethylamino, n-, iso-propylamino, n-, iso-, tert-butylamino, and the like.

"Aminoalkyl" means a linear monovalent hydrocarbon radical of one to six carbon atoms or a branched monovalent hydrocarbon radical of three to six carbons substituted with at least one, preferably one or two, —NRR' where R is hydrogen, alkyl, acyl, hydroxyalkyl, alkoxyalkyl, aryl, aralkyl, heteroaryl, heteroaralkyl or heterocyclylalkyl and R' is hydrogen, alkyl, hydroxyalkyl, alkoxyalkyl, aryl, aralkyl, heteroaryl, heteroaralkyl, heterocyclylalkyl, cycloalkyl, cycloalkylalkyl, aminocarbonyl, or aminosulfonyl as defined herein e.g., aminomethyl, methylaminoethyl, dimethylaminoethyl, 1,3-diaminopropyl, acetylaminopropyl, and the like.

"Acyl" refers to a —COR radical where R is hydrogen, alkyl, haloalkyl, cycloalkyl, aryl, aralkyl, heteroaryl, heteroaralkyl, or heterocyclyl as defined herein, e.g., formyl, acetyl, trifluoroacetyl, benzoyl, piperazin-1-ylcarbonyl, and the like. When R is alkyl it is referred to in this application as alkylcarbonyl. When R is aryl it is referred to in this application as arylcarbonyl. When R is heteroaryl it is referred to in this application as heteroarylcarbonyl. When R is heterocyclyl it is referred to in this application as heterocyclylcarbonyl.

"Acylamino" refers to a —NRCOR' radical where R is hydrogen or alkyl and R' is hydrogen, alkyl, halo alkyl, cycloalkyl, aryl, aralkyl, heteroaryl, heteroaralkyl, or heterocyclyl as defined herein, e.g., formyl, acetyl, trifluoroacetyl, benzoyl, piperazin-1-ylcarbonyl, and the like.

"Aminocarbonyl" means —CONRR' radical where R and R' are independently selected from hydrogen, alkyl, aryl, aralkyl, heteroaryl, heteroaralkyl, or heterocyclylalkyl or R and R' together with the nitrogen atom to which they are attached form heterocycloamino as defined herein.

"Aminosulfonyl" means —SO$_2$NRR' radical where R and R' are independently selected from hydrogen, alkyl, aryl, aralkyl, heteroaryl, heteroaralkyl, or heterocyclylalkyl or R and R' together with the nitrogen atom to which they are attached form heterocycloamino as defined herein.

"Animal" includes humans, non-human mammals (e.g., dogs, cats, rabbits, cattle, horses, sheep, goats, swine, deer, and the like) and non-mammals (e.g., birds, and the like).

"Aromatic" refers to a moiety wherein the constituent atoms make up an unsaturated ring system, all atoms in the ring system are sp$^2$ hybridized and the total number of pi electrons is equal to 4n+2.

"Aryl" refers to a monocyclic or fused bicyclic ring assembly containing 6 to 10 ring carbon atoms wherein each ring is aromatic e.g., phenyl or naphthyl.

"Aryloxy" refers to a —O—R radical where R is aryl as defined above e.g., phenoxy, napthyloxy, and the like.

"Aryloxycarbonyl" refers to a —C(O)OR radical where R is aryl as defined above e.g., phenyloxycarbonyl, naphthyloxycarbonyl, and the like.

"Aralkyl" refers to a -(alkylene)-R radical where R is aryl as defined above e.g., benzyl, phenethyl, and the like.

"Arylthio" means an —SR radical where R is aryl as defined herein, e.g., phenylthio or naphthylthio.

"Arylsulfonyl" means an —SO$_2$R radical where R is aryl as defined herein, e.g., phenylsulfonyl or naphthylsulfonyl.

"Carboxy" refers to —C(O)OH radical.

"Carboxyalkyl" means an alkyl radical, as defined herein, substituted with at least one, preferably one or two, —C(O)OH group(s), e.g., carboxymethyl, carboxyethyl, 1-, 2-, or 3-carboxypropyl, and the like.

"Cycloalkyl" refers to a monovalent saturated monocyclic ring containing three to eight ring carbon atoms e.g., cyclopropyl, cyclobutyl, cyclopentyl, cyclohexyl, and the like.

"Cycloalkylalkyl" refers to a -(alkylene)-R radical where R is cycloalkyl as defined above e.g., cyclopropylmethyl, cyclobutylethyl, cyclobutylmethyl, and the like.

"Cycloalkyloxy" refers to a —OR radical where R is cycloalkyl as defined above e.g., cyclopropyloxy, cyclopentyloxy, cyclohexyloxy, and the like.

"Cycloalkyloxycarbonylamino" refers to a —NHC(O)OR radical where R is cycloalkyl as defined above e.g., cyclopropyloxycarbonylamino, cyclopentyloxycarbonylamino, and the like.

"Cycloalkylalkyloxycarbonylamino" refers to a —NHC(O)OR radical where R is cycloalkylalkyl as defined above e.g., cyclopropylmethyloxycarbonylamino, cyclopentylmethyloxycarbonylamino, and the like.

"Disease" specifically includes any unhealthy condition of an animal or part thereof and includes an unhealthy condition that may be caused by, or incident to, medical or veterinary therapy applied to that animal, i.e., the "side effects" of such therapy.

"Dialkylamino" means a radical —NRR' where R and R' are independently alkyl as defined herein, e.g., dimethylamino, diethylamino, N,N-methylpropylamino or N,N-methylethylamino, and the like.

"Disubstituted amino" means a radical —NRR' where R and R' are independently selected from alkyl, cycloalkyl, cycloalkylalkyl, hydroxyalkyl, alkoxyalkyl, aminoalkyl, aryl, aralkyl, heteroaryl, or heteroaralkyl as defined herein, e.g., dimethylamino, diethylamino, N,N-methylpropylamino or N,N-methylethylamino, methylphenylamino, and the like. Dialkylamino is a subgroup of disubstituted amino.

"Fused heterocyclyl" means heterocyclyl radical as defined herein that is fused to an aryl or heteroaryl ring as defined herein e.g., 2,3-dihydroisoindol-1-yl, 1,2,3,4-tetrahydroisoquinolin-1-yl, and the like.

"Halo" refers to fluoro, chloro, bromo or iodo.

"Haloalkyl" refers to alkyl as defined above substituted by one or more, preferably one to seven, "halo" atoms, as such terms are defined in this Application. Haloalkyl includes monohaloalkyl, dihaloalkyl, trihaloalkyl, perhaloalkyl and the like e.g. chloromethyl, dichloromethyl, difluoromethyl, trifluoromethyl, 2,2,2-trifluoroethyl, perfluoroethyl, 2,2,2-trifluoro-1,1-dichloroethyl, and the like.

"Haloalkoxy" refers to a —OR radical where R is haloalkyl group as defined above e.g., trifluoromethoxy, 2,2,2-trifluoroethoxy, difluoromethoxy, and the like.

"Heteroaryl" as a group or part of a group denotes an aromatic monocyclic or bicyclic moiety of 5 to 10 ring atoms in which one or more, preferably one, two, or three, of the ring atom(s) is(are) selected from nitrogen, oxygen or sulfur, the remaining ring atoms being carbon. Representative heteroaryl rings include, but are not limited to, pyrrolyl, furanyl, thienyl, oxazolyl, isoxazolyl, thiazolyl, imidazolyl, triazolyl, tetrazolyl, pyridinyl, pyrimidinyl, pyrazinyl, pyridazinyl, indolyl, benzofuranyl, benzothiophenyl, benzimidazolyl, quinolinyl, isoquinolinyl, quinazolinyl, quinoxalinyl, pyrazolyl, and the like.

"Heteroaryloxy" refers to a —O—R radical where R is heteroaryl as defined above e.g., furanyloxy, pyridinyloxy, indolyloxy, and the like.

"Heteroaryloxycarbonyl" refers to a —C(O)O—R radical where R is heteroaryl as defined above e.g., pyridinyloxycarbonyl, pyrimidinyloxycarbonyl, and the like.

"Heteroaralkyl" refers to a -(alkylene)-R radical where R is heteroaryl as defined above e.g., pyridinylmethyl, 1- or 2-furanylethyl, imidazolylmethyl, and the like.

"Heteroaralkyloxycarbonyl" refers to a —C(O)O—R radical where R is heteroaralkyl as defined above e.g., pyridinylmethyloxycarbonyl, pyrimidinylmethyloxycarbonyl, and the like.

"Heteroarylthio" means an —SR radical where R is heteroaryl as defined herein, e.g., pyridinylthio, furanylthio, thienylthio, and the like.

"Heteroarysulfonyl" means an —SO$_2$R radical where R is heteroaryl as defined herein, e.g., pyridinylsulfonyl, thienylsulfonyl, and the like.

"Heterocyclyl" refers to a saturated or partially unsaturated, mono or bicyclic radical of 4, 5, 6, or 7 carbon ring atoms wherein one or more, preferably one, two, or three of the ring carbon atoms are replaced by a heteroatom selected from —N=, —N—, —O—, —S—, —SO—, or —S(O)$_2$— and further wherein one or two ring carbon atoms are optionally replaced by a keto (—CO—) group. The heterocyclyl ring is optionally fused to cycloalkyl, aryl or heteroaryl ring as defined herein. Representative examples include, but are not limited to, imidazolidinyl, morpholinyl, thiomorpholinyl, thiomorpholino-1-oxide, thiomorpholino-1,1-dioxide, tetrahydropyranyl, tetrahydropyranyl, tetrahydrothiopyranyl, 1-oxo-tetrahydrothiopyranyl, 1,1-dioxotetrathio-pyranyl, indolinyl, piperazinyl, piperidyl, pyrrolidinyl, pyrrolinyl, quinuclidiny-1,3,4-dihydroisoquinolinyl, dihydroindolyl, and the like. When the heterocyclyl group contains at least one nitrogen ring atom it is referred to herein as "heterocycloamino" and is a subset of the heterocyclyl group as defined above.

"Heterocyclylalkyl" refers to a -(alkylene)-R radical where R is heterocyclyl as defined above e.g., pyrrolidinylmethyl, tetrahydrofuranylethyl, pyridinylmethylpiperidinylmethyl, and the like.

"Heterocyclyloxycarbonyl" refers to a —C(O)OR radical where R is heterocyclyl as defined above e.g., piperidinyloxycarbonyl, tetrahydrofuranoxycarbonyl, and the like.

"Heterocyclylsulfonyl" means an —SO$_2$R radical where R is heterocyclyl as defined herein, e.g., piperidin-1-ylsulfonyl, pyrrolidin-1-ylsulfonyl, and the like.

"Hydroxy" means —OH radical.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Isomers" mean compounds of Formula (I) having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center that has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this Application to describe compounds of Formula (I) are meant to encompass all possible stereoisomers.

"Monosubstituted amino" means a radical —NHR where R is selected from alkyl, cycloalkyl, cycloalkylalkyl, hydroxyalkyl, alkoxyalkyl, aminoalkyl, aryl, aralkyl, heteroaryl, or heteroaralkyl as defined herein, e.g., methylamino, ethylamino, propylamino, phenylamino, benzylamino, and the like.

"Optional" or "optionally" or "may be" means that the subsequently described event or circumstance may or may not occur, and that the description includes instances where the event or circumstance occurs and instances in which it does not. For example, the phrase "wherein the aromatic ring in $R^a$ is optionally substituted with one or two substituents independently selected from alkyl" means that the aromatic ring may or may not be substituted with alkyl in order to fall within the scope of the invention.

The present invention also includes N-oxide derivatives of a compound of Formula (I). N-oxide derivative mean a compound of Formula (I) in which a nitrogen atom is in an oxidized state (i.e., N→O) e.g., pyridine N-oxide, and which possess the desired pharmacological activity.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula (I) which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methylsulfonic acid, ethanesulfonic acid, 1,2-ethanedisulfonic acid, 2-hydroxy-ethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'- methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

The present invention also includes prodrugs of a compound of Formula (I). Prodrug means a compound that is convertible in vivo by metabolic means (e.g. by hydrolysis) to a compound of Formula (I). For example, an ester of a compound of Formula (I) containing a hydroxy group may be convertible by hydrolysis in vivo to the parent molecule. Alternatively an ester of a compound of Formula (I) containing a carboxy group may be convertible by hydrolysis in vivo to the parent molecule. Suitable esters of compounds of Formula (I) containing a hydroxy group, are for example acetates, citrates, lactates, tartrates, malonates, oxalates, salicylates, propionates, succinates, fumarates, maleates, methylene-bis-βb-hydroxynaphthoates, gentisates, isethionates, di-p-toluoyltartrates, methylsulphonates, ethanesulphonates, benzenesulphonates, p-toluenesulphonates, cyclohexylsulphamates and quinates. Suitable esters of compounds of Formula (I) containing a carboxy group, are for example those described by Leinweber, F. J. *Drug Metab. Res.*, 1987, 18, page 379. An especially useful class of esters of compounds of Formula (I) containing a hydroxy group, may be formed from acid moieties selected from those described by Bundgaard et al., *J. Med. Chem.*, 1989, 32, pp 2503-2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl) benzoates, e.g. 3- or 4-(morpholinomethyl)-benzoates, and (4-alkylpiperazin-1-yl)benzoates, e.g. 3- or 4-(4-alkylpiperazin-1-yl)benzoates. It is understood that the names and illustration used in this Application to describe compounds of Formula (I) are meant to be encompassed all possible prodrugs thereof.

"Protected derivatives" means derivatives of compounds of Formula (I) in which a reactive site or sites are blocked with protecting groups. Protected derivatives of compounds of Formula (I) are useful in the preparation of compounds of Formula (I) or in themselves may be active cathepsin S inhibitors. A comprehensive list of suitable protecting groups can be found in T. W. Greene, *Protective Groups in Organic Synthesis*, 3rd edition, John Wiley & Sons, Inc. 1999. It is understood that the names and illustration used in this Application to describe compounds of Formula (I) are meant to be encompassed all possible protected derivatives thereof.

"Therapeutically effective amount" means that amount which, when administered to an animal for treating a disease, is sufficient to effect such treatment for the disease.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

"Ureido" means a radical —NHCONRR' where R is hydrogen or alkyl and R' is hydrogen, alkyl, cycloalkyl, or cycloalkylalkyl.

Preferred Embodiments

Certain compounds of Formula (I) within the broadest scope set forth in the Summary of the Invention are preferred. For example:

A. A preferred group of compounds of Formula (I) is that wherein:

E is —COCONHR$^6$ where R$^6$ is hydrogen, alkyl, cycloalkyl, aralkyl, or heteroaralkyl wherein the aromatic ring is optionally substituted with one or two halo, preferably, R$^6$ is cyclopropyl, —CH(CH$_3$)R where R is phenyl, 4-chlorophenyl, 2,4-dichlorophenyl, 2,4-difluorophenyl, 3,4-dichlorophenyl, 3,4-difluorophenyl, or pyridin-4-yl. Preferably, R$^6$ is cyclopropyl.

B. Another preferred group of compounds of Formula (I) is that wherein:

E is —COCOOR$^{10}$ where R$^{10}$ is as defined in the Summary of the Invention. Preferably, R$^{10}$ is —CH$_2$C≡CH, —CH$_2$CH=CH$_2$, n-propyl, 2,2-dimethylpropyl, carboxymethyl, methoxycarbonylmethyl, tert-butoxycarbonylmethyl, —CH$_2$C(O)OCH$_2$C≡CH, —CH$_2$C(O)OCH$_2$CH=CH$_2$, —CH$_2$C(O)O(CH$_2$)$_2$CH$_3$, —CH$_2$C(O)NH$_2$, —CH$_2$C(O)NHCH$_3$, —CH$_2$C(O)N(CH$_3$)$_2$, —CH$_2$C(O)NHCH$_2$CH=CH$_2$, or 2-phenethyl.

(a) Within the above preferred groups A and B and more preferred groups contained therein, a more preferred group of compounds is that wherein:

X is —O—;

R$^1$ is alkyl optionally substituted with alkoxy, alkylthio or alkylsulfonyl, alkenyl, alkynyl, cycloalkyl, or cycloalkylalkyl, preferably methyl, ethyl, n-propyl, n-butyl, n-pentyl, prop-2-enyl, propyn-2-yl, 1-methylethyl, 1-methylpropyl, 2-methylpropyl, 3-methylbutyl, cyclopropyl, methoxymethyl, 2-methoxyethyl, methylthiomethyl, methylsulfonylmethyl, or cyclobutylmethyl. More preferably, cyclobutylmethyl, ethyl, n-propyl or n-butyl; and R$^3$ is alkyl, cycloalkyl, or aryl, more preferably, 1-methylethyl, 1-methylpropyl, tert-butyl, cyclopropyl, phenyl, or cyclohexyl. Preferably, R$^3$ is tert-butyl or cyclohexyl.

(1) Within the groups (A), (B), A(a), and B(a) and more preferred groups contained therein, a more preferred group of compounds is that wherein:

Y is —OC(O)NH—; R$^2$ is heteroaryl optionally substituted with one, two, three, or four R$^d$ independently selected from hydrogen, alkyl, cycloalkyl, alkynyl, alkylthio, hydroxy, alkoxy, halo, haloalkyl, haloalkoxy, carboxy, carboxyalkyl, hydroxyalkyl, alkoxyalkyl, aminoalkyl, alkylsulfonyl, alkylcarbonyl, aryl, aralkyl, arylsulfonyl, arylcarbonyl, aryloxycarbonyl, aminosulfonyl, aminocarbonyl, heteroaryl, heteroaralkyl, heteroarylsulfonyl, heteroarylcarbonyl, heteroaryloxycarbonyl, heterocyclyl, heterocyclylalkyl, heterocyclylsulfonyl, heterocyclylcarbonyl, heterocyclyloxycarbonyl, amino, monosubstituted amino, or disubstituted amino or when two R$^d$ are on adjacent carbon atoms they, together with the carbon atoms to which they are attached, form a four, five or six membered heterocyclyl ring containing one or two heteroatoms selected from nitrogen, oxygen, sulfur, or —SO$_2$— wherein the heterocyclyl ring is optionally substituted with one or two alkyl; and further wherein the aromatic or alicyclic ring in R$^d$ is optionally substituted with one, two, or three R$^e$ independently selected from alkyl, alkoxycarbonylamino, cycloalkyl, cycloalkylalkyl, cycloalkoxycarbonylamino, cycloalkylalkyloxycarbonylamino, nitro, alkoxy, cycloalkyloxy, aryloxy, heteroaryloxy, halo, haloalkyl, haloalkoxy, hydroxyl, carboxy, alkoxycarbonyl, monosubstituted amino, disubstituted amino, acylamino, or ureido wherein the cycloalkyl and cycloalkylalkyl in R$^e$ are optionally substituted with one, two or three alkyl; and R$^4$ is alkyl, preferably tert-butylmethyl provided that at least one of R$^d$ is not hydrogen.

(i) Preferably, R$^2$ is a group of formula (a):

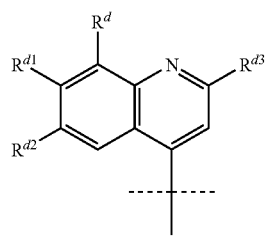

(a)

where:
R$^{d1}$ is hydrogen, hydroxy, alkoxy, amino, alkylamino, dialkylamino, haloalkoxy or alkylsulfonyl;
R$^d$ and R$^{d2}$ are independently hydrogen, alkyl, halo, alkoxy, alkylthio, or alkylsulfonyl; or
R$^{d1}$ and R$^d$ or R$^{d1}$ and R$^{d2}$ together with the carbon atoms to which they are attached form 4, 5, or 6-atom heterocyclyl ring wherein one or two ring atoms are replaced by oxygen or —N— where the heterocyclyl ring is optionally substituted with one or two alkyl;
R$^{d3}$ is aryl, heteroaryl, cycloalkyl or heterocyclyl optionally substituted with halo, alkyl, cycloalkyl, cycloalkylalkyl, alkoxy, cycloalkoxy, nitro, alkylcarbonylamino, cycloalkylcarbonylamino, cycloalkylalkylcarbonylamino, alkoxycarbonylamino, amino, alkylamino, dialkylamino, cycloalkylamino, cycloalkylalkylamino, or —NHCONRR' where R is hydrogen or alkyl and R' is hydrogen, alkyl, cycloalkyl, or cycloalkylalkyl wherein cycloalkyl and cycloalkylalkyl in R$^{d3}$ are optionally substituted with one, two or three alkyl.

Preferably,
R$^{d1}$ is hydrogen, hydroxy, alkoxy, amino, alkylamino or dialkylamino;
R$^d$ and R$^{d2}$ are independently hydrogen, alkyl, halo, alkoxy, alkylthio, or alkylsulfonyl; and
R$^{d3}$ is a group of formula:

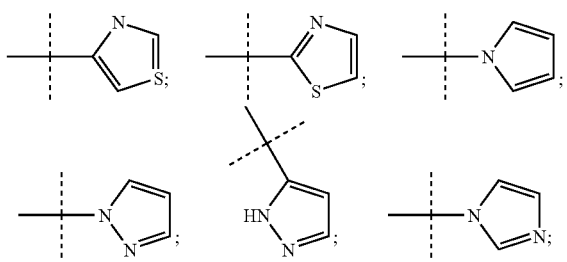

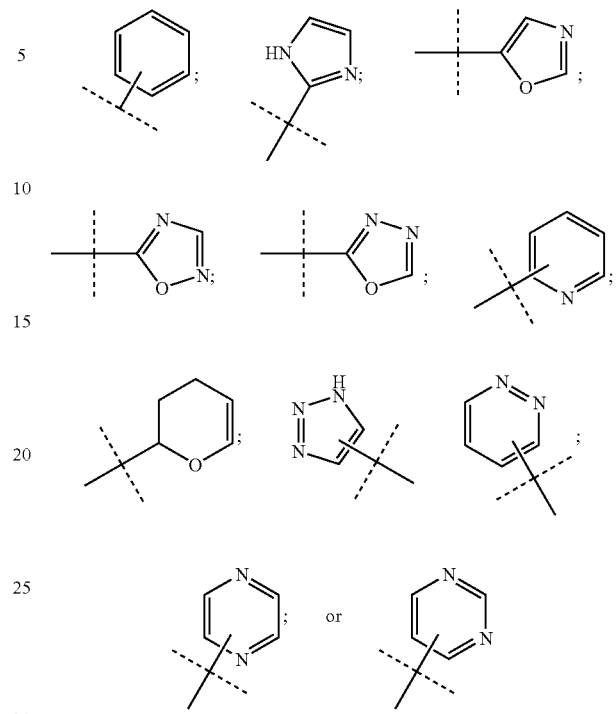

optionally substituted with halo, alkyl, cycloalkyl, cycloalkylalkyl, alkoxy, cycloalkoxy, nitro, alkylcarbonylamino, cycloalkylcarbonylamino, cycloalkylalkylcarbonylamino, alkyloxycarbonylamino, amino, alkylamino, dialkylamino, cycloalkylamino, cycloalkylalkylamino, or —NHCONRR' where R is hydrogen or alkyl and R' is hydrogen, alkyl, cycloalkyl, or cycloalkylalkyl wherein cycloalkyl and cycloalkylalkyl are optionally substituted with one, two or three alkyl.

More preferably, R$^{d3}$ is a group of formula:

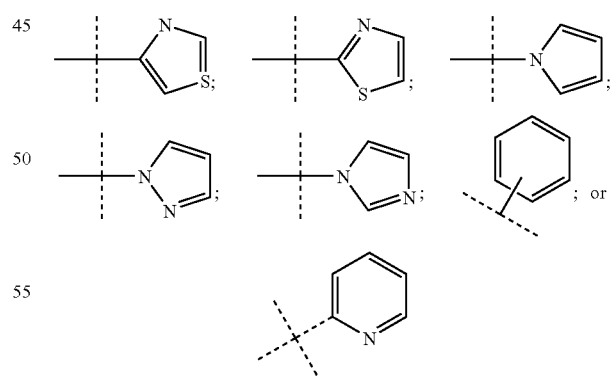

optionally substituted with halo, alkyl, cycloalkyl, cycloalkylalkyl, alkoxy, cycloalkoxy, nitro, alkylcarbonylamino, cycloalkylcarbonylamino, cycloalkylalkylcarbonylamino, alkyloxycarbonylamino, amino, alkylamino, dialkylamino, cycloalkylamino, cycloalkylalkylamino, or —NHCONRR' where R is hydrogen or alkyl and R' is hydrogen, alkyl, cycloalkyl, or cycloalkylalkyl wherein cycloalkyl and cycloalkylalkyl are optionally substituted with one, two or three alkyl.

Even more preferably, $R^{d3}$.

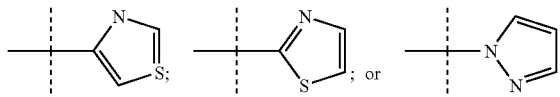

optionally substituted with halo, alkyl, cycloalkyl, cycloalkylalkyl, alkoxy, cycloalkoxy, nitro, alkylcarbonylamino, cycloalkylcarbonylamino, cycloalkylalkylcarbonylamino, alkyloxycarbonylamino, amino, alkylamino, dialkylamino, cycloalkylamino, cycloalkylalkylamino, or —NHCONRR' where R is hydrogen or alkyl and R' is hydrogen, alkyl, cycloalkyl, or cycloalkylalkyl wherein cycloalkyl and cycloalkylalkyl are optionally substituted with one, two or three alkyl.

In still other preferred embodiments of subgroup (i), $R^{d3}$ is cycloalkyl, more preferably cyclopropyl, cyclobutyl or cyclopentyl, still more preferably, cyclopropyl. The remaining groups, $R^d$, $R^{d1}$ and $R^{d2}$ have the meanings provided for formula (a).

Within the above preferred groups, a more preferred group of compounds is that wherein:

$R^{d1}$ is hydrogen, hydroxy, methoxy, ethoxy, n-propoxy, isopropoxy, methylamino, ethylamino, n-propylamino, isopropylamino, dimethylamino, methylethylamino, methyl(n-propyl)amino and methyl(isopropyl)amino; more preferably, hydrogen hydroxyl; methoxy or dimethylamino, even more preferably methoxy. Alternatively, even more preferably hydrogen;

$R^d$ and $R^{d2}$ are independently, hydrogen, fluoro, chloro, methyl, ethynyl, methoxy, ethoxy, methylthio or methylsulfonyl. More preferably, $R^d$ is hydrogen, ethynyl, fluoro, chloro, methyl, methoxy, methylthio or methylsulfonyl and $R^{d2}$ is hydrogen.

Most preferably, $R^{d1}$ is methoxy, $R^d$ is hydrogen or methyl, fluoro, chloro, or methoxy and $R^{d2}$ is hydrogen.

(ii) Preferably, $R^2$ is a group of formula:

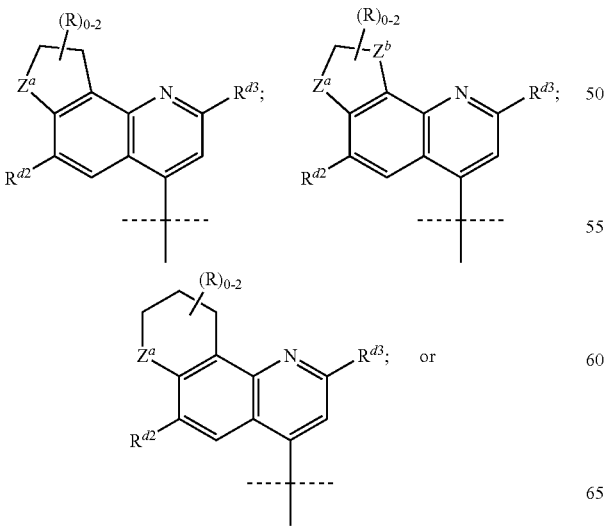

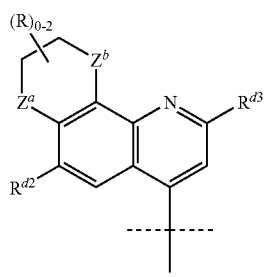

where:

$Z^a$ and $Z^b$ are independently —O— or —NH— where H can be replaced by R, preferably $Z^a$ and $Z^b$ are —O—;

R is alkyl, preferably methyl;

$R^{d2}$ is hydrogen or methyl, preferably hydrogen; and $R^{d3}$ is as defined for subgroup (i) immediately above.

(iii) Preferably, $R^2$ is a group of formula:

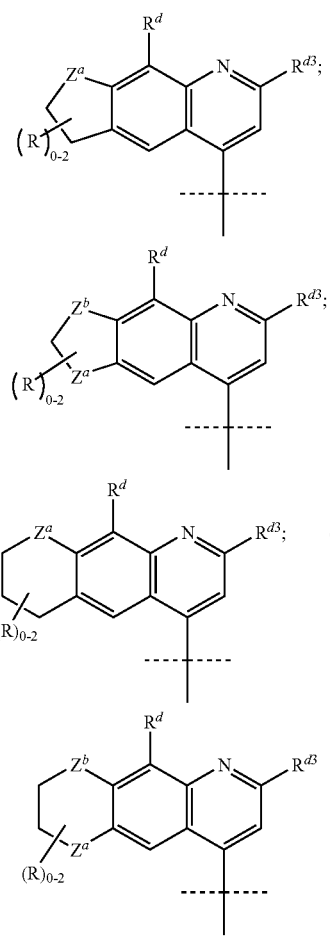

$Z^a$ and $Z^b$ are independently —O— or —NH— where H can be replaced by R, preferably $Z^a$ and $Z^b$ are —O—;

R is alkyl, preferably methyl;

$R^d$ is hydrogen or methyl, preferably hydrogen; and $R^{d3}$ is as defined for subgroup (i) immediately above.

(iv) Preferably, R² is a group of formula (b):

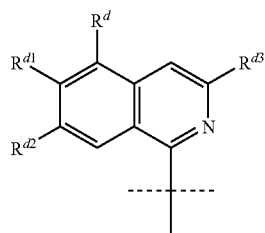

where:
$R^{d1}$ is hydrogen, hydroxy, alkoxy, amino, alkylamino, dialkylamino, haloalkoxy or alkylsulfonyl;
$R^d$ and $R^{d2}$ are independently hydrogen, alkyl, halo, alkoxy, alkylthio, or alkylsulfonyl; or
$R^{d1}$ and $R^d$ or $R^{d1}$ and $R^{d2}$ together with the carbon atoms to which they are attached form 4, 5, or 6-atom heterocyclyl ring wherein one or two ring atoms are replaced by oxygen or —N— where the heterocyclyl ring is optionally substituted with one or two alkyl;
$R^{d3}$ is hydrogen, alkyl, cycloalkyl or cycloalkylalkyl.
Preferably,
$R^{d1}$ is hydrogen, hydroxy, alkoxy, amino, alkylamino or dialkylamino;
$R^d$ and $R^{d2}$ are independently hydrogen, alkyl, halo, alkoxy, alkylthio, or alkylsulfonyl; and
$R^{d3}$ is hydrogen, alkyl or cycloalkyl.
Within the above preferred groups, a more preferred group of compounds is that wherein:
$R^{d1}$ is hydrogen, hydroxy, methoxy, ethoxy, n-propoxy, isopropoxy, methylamino, ethylamino, n-propylamino, isopropylamino, dimethylamino, methylethylamino, methyl(n-propyl)amino and methyl(isopropyl)amino; more preferably, hydrogen, hydroxyl, methoxy, ethoxy or dimethylamino, even more preferably methoxy or ethoxy; and
$R^d$ and $R^{d2}$ are independently, hydrogen, fluoro, chloro, methyl, ethynyl, methoxy, ethoxy, methylthio or methylsulfonyl; more preferably, $R^d$ is hydrogen, ethynyl, fluoro, chloro, methyl, methoxy, methylthio or methylsulfonyl and $R^{d2}$ is hydrogen.
Most preferably, $R^{d1}$ is methoxy or ethoxy, $R^d$ is hydrogen or methyl, fluoro, chloro, or methoxy and $R^{d2}$ is hydrogen.
Within the above groups (i)-(iii), and more preferred groups contained therein, a more preferred group of compounds is that wherein the $R^{d3}$ rings are optionally substituted with methyl, ethyl, n-propyl, i-propyl, n-butyl, 1-methylpropyl, 2-methylpropyl, tert-butyl, 2,2,dimethylpropyl, 1,2-dimethylpropyl, 1,2,2-trimethylpropyl, cyclopropyl, cyclobutyl, cyclopentyl, cyclohexyl, cyclopropylmethyl, cyclobutylmethyl, cyclopentylmethyl and cyclohexylmethyl each of said cycloalkyl and cycloalkylalkyl rings being optionally substituted with one to three substitutents independently selected from methyl or ethyl, preferably methyl.
Within the above groups (i)-(iii), and more preferred groups contained therein, a more preferred group of compounds is that wherein the $R^{d3}$ rings are optionally substituted with amino, methylamino, ethylamino, propylamino, 1-methylethylamino, 1,1-dimethylethylamino, 2-methylpropylamino, 1-methylpropylamino, 2,2-dimethylpropylamino, 1,2-dimethylpropylamino, 1,1-dimethylpropylamino, cyclopropylamino, cyclobutylamino, cyclopentylamino, cyclohexylamino, cyclopropylmethylamino, cyclobutylmethylamino, cyclopentylmethylamino, cyclohexylmethylamino, methylcarbonylamino, ethylcarbonylamino, propylcarbonylamino, 1-methylethylcarbonylamino, 1,1-dimethylethylcarbonylamino, 2-methylpropylcarbonylamino, 1-methylpropylcarbonylamino, 2,2-dimethylpropylcarbonylamino, 1,2-dimethylpropylcarbonylamino, 1,1-dimethylpropylcarbonylamino, cyclopropylcarbonylamino, cyclobutylcarbonylamino, cyclopentylcarbonylamino, cyclohexylcarbonylamino, cyclopropylmethylcarbonylamino, cyclobutylmethylcarbonylamino, cyclopentylmethylcarbonylamino, cyclohexylmethylcarbonylamino, methoxycarbonylamino, ethoxycarbonylamino, propoxycarbonylamino, 1-methylethoxycarbonylamino, 1,1-dimethyl-ethoxycarbonylamino, 2-methylpropoxycarbonylamino, 1-methylpropoxycarbonylamino, 2,2-dimethylpropoxycarbonylamino, 1,2-dimethylpropoxylcarbonylamino, or 1,1-dimethylpropoxy-carbonylamino.

(2) Within the groups (A), (B), A(a), and B(a) and more preferred groups contained therein, a more preferred group of compounds is that wherein:
Y is —NHC(O)NH—, R² is as defined in preferred embodiment (1) above, including the preferred subgroups thereof, and R⁴ is alkyl, preferably tert-butyl.

(3) Within the groups (A), (B), A(a), and B(a) and more preferred groups contained therein, a more preferred group of compounds is that wherein:
Y is —C(O)NH—, R² is as defined in preferred embodiment (1) above, including the preferred subgroups thereof provided that $R^{d3}$ is a heteroaryl ring, and R⁴ is as defined in the Summary of the Invention, preferably alkyl, more preferably tert-butyl.

(4) Within the groups (A), (B), A(a), and B(a) and more preferred groups contained therein, a more preferred group of compounds is that wherein:
Y is —OC(O)NH—, R² is —CO-(fused heterocyclyl) wherein the fused heterocyclyl is optionally substituted with one, two, or three $R^d$ independently selected from alkyl, alkoxy, halo, haloalkyl, haloalkoxy, carboxy, carboxyalkyl, hydroxyalkyl, alkoxyalkyl, aminoalkyl, alkylsulfonyl, alkylcarbonyl, aryl, aralkyl, arylsulfonyl, arylcarbonyl, aryloxycarbonyl, aminosulfonyl, aminocarbonyl, heteroaryl, heteroaralkyl, heteroarylsulfonyl, heteroarylcarbonyl, heteroaryloxycarbonyl, heterocyclyl, heterocyclylalkyl, heterocyclylsulfonyl, heterocyclylcarbonyl, heterocyclyloxycarbonyl, monosubstituted amino, or disubstituted amino wherein the aromatic or alicyclic ring in $R^d$ is optionally substituted with one, two, or three $R^e$ independently selected from alkyl, alkoxy, halo, haloalkyl, haloalkoxy, hydroxyl, carboxy, alkoxycarbonyl, monosubstituted amino, disubstituted amino, or acylamino; and R⁴ is alkyl. Preferably, R² is 2,3-dihydroisoindol-1-yl, 1,2,3,4-tetrahydroisoquinolin-1-yl substituted with one, two, or three $R^d$ listed immediately above.

(5) Within the groups (A), (B), A(a), and B(a) and more preferred groups contained therein, a more preferred group of compounds is that wherein:
Y is —NHC(O)NH—, R² is —CO-(fused heterocyclyl) wherein the fused heterocyclyl is substituted with one, two, or three $R^d$ independently selected from alkyl, alkoxy, halo, haloalkyl, haloalkoxy, carboxy, carboxyalkyl, hydroxyalkyl, alkoxyalkyl, aminoalkyl, alkylsulfonyl, alkylcarbonyl, aryl, aralkyl, arylsulfonyl, arylcarbonyl, aryloxycarbonyl, aminosulfonyl, aminocarbonyl, heteroaryl, heteroaralkyl, heteroarylsulfonyl, heteroarylcarbonyl, heteroaryloxycarbonyl, heterocyclyl, heterocyclylalkyl, heterocyclylsulfonyl, heterocyclylcarbonyl, heterocyclyloxycarbonyl, monosubstituted amino, or disubstituted amino wherein the aromatic or alicyclic ring in $R^d$ is optionally substituted with one, two, or three R$^e$ independently selected from alkyl, alkoxy, halo, haloalkyl, haloalkoxy, hydroxyl, carboxy, alkoxycarbonyl, monosubstituted amino, disubstituted amino, or acylamino; and R$^4$ is alkyl. Preferably, R$^2$ is 2,3-dihydroisoindol-1-yl, 1,2,3,4-tetrahydroisoquinolin-1-yl optionally substituted with one, two, or three R$^d$ listed immediately above.

(C) Yet another preferred group of compounds of Formula (I) is that wherein R$^2$ is a group of formula (a):

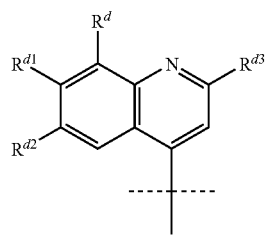

(a)

where:
R$^{d1}$ is hydrogen, hydroxy, alkoxy, amino, alkylamino, dialkylamino, haloalkoxy or alkylsulfonyl;
R$^d$ and R$^{d2}$ are independently hydrogen, alkyl, halo, alkoxy, alkylthio, or alkylsulfonyl; or
R$^{d1}$ and R$^d$ or R$^{d1}$ and R$^{d2}$ together with the carbon atoms to which they are attached form 4, 5, or 6-atom heterocyclyl ring wherein one or two ring atoms are replaced by oxygen or —N— where the heterocyclyl ring is optionally substituted with one or two alkyl;
R$^{d3}$ is aryl, heteroaryl, cycloalkyl or heterocyclyl optionally substituted with halo, alkyl, cycloalkyl, cycloalkylalkyl, alkoxy, cycloalkoxy, nitro, alkylcarbonylamino, cycloalkylcarbonylamino, cycloalkylalkylcarbonylamino, alkyloxycarbonylamino, amino, alkylamino, dialkylamino, or —NHCONRR' where R is hydrogen or alkyl and R' is hydrogen, alkyl, cycloalkyl, or cycloalkylalkyl wherein cycloalkyl and cycloalkylalkyl are optionally substituted with one, two or three alkyl.

(i) Preferably,
R$^{d1}$ is hydrogen, hydroxy, alkoxy, amino, alkylamino or dialkylamino;
R$^d$ and R$^{d2}$ are independently hydrogen, alkyl, halo, alkoxy, alkylthio, or alkylsulfonyl; and
R$^{d3}$ is a group of formula:

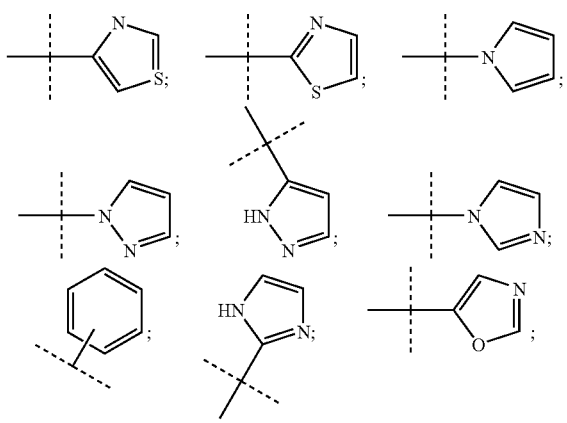

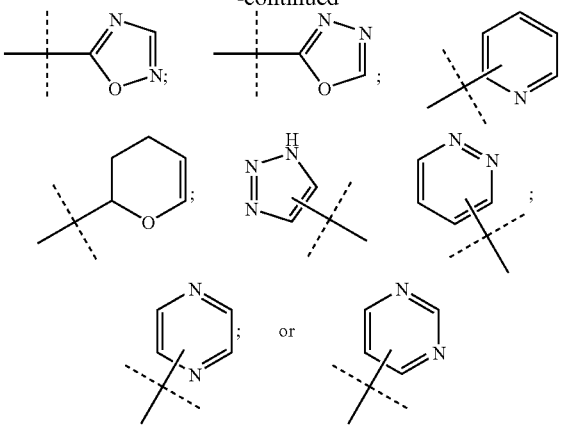

optionally substituted with halo, alkyl, cycloalkyl, cycloalkylalkyl, alkoxy, cycloalkoxy, nitro, amkylcarbonylamino, cycloalkylcarbonylamino, cycloalkylalkylcarbonylamino, alkyloxycarbonylamino, amino, alkylamino, dialkylamino, or —NHCONRR' where R is hydrogen or alkyl and R' is hydrogen, alkyl, cycloalkyl, or cycloalkylalkyl wherein cycloalkyl and cycloalkylalkyl are optionally substituted with one, two or three alkyl.

More preferably, R$^{d3}$ is a group of formula:

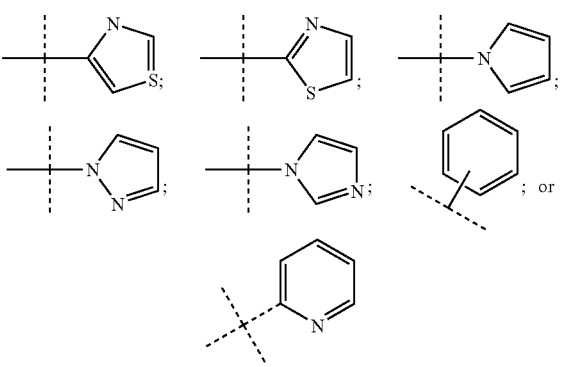

optionally substituted with halo, alkyl, cycloalkyl, cycloalkylalkyl, alkoxy, cycloalkoxy, nitro, alkylcarbonylamino, cycloalkylcarbonylamino, cycloalkylalkylcarbonylamino, alkyoxycarbonylamino, amino, alkylamino, dialkylamino, or —NHCONRR' where R is hydrogen or alkyl and R' is hydrogen, alkyl, cycloalkyl, or cycloalkylalkyl wherein cycloalkyl and cycloalkylalkyl are optionally substituted with one, two or three alkyl.

Even more preferably, R$^{d3}$ is:

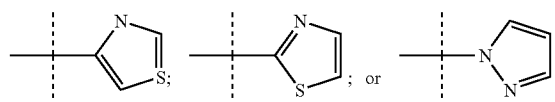

optionally substituted with halo, alkyl, cycloalkyl, cycloalkylalkyl, alkoxy, cycloalkoxy, nitro, amkylcarbonylamino, cycloalkylcarbonylamino, cycloalkylalkylcarbonylamino, alkyloxycarbonylamino, amino, alkylamino, dialkylamino, or —NHCONRR' where R is hydrogen or alkyl and R' is hydrogen, alkyl, cycloalkyl, or cycloalkylalkyl wherein cycloalkyl and cycloalkylalkyl are optionally substituted with one, two or three alkyl.

Within the above preferred groups, a more preferred group of compounds is that wherein:

$R^{d1}$ is hydrogen, hydroxy, methoxy, ethoxy, n-propoxy, isopropoxy, methylamino, ethylamino, n-propylamino, isopropylamino, dimethylamino, methylethylamino, methyl(n-propyl)amino and methyl(isopropyl)amino; more preferably, hydrogen hydroxyl; methoxy or dimethylamino, even more preferably methoxy. Alternatively, even more preferably hydrogen;

$R^d$ and $R^{d2}$ are independently, fluoro, chloro, methyl, ethynyl, methoxy, ethoxy, thiomethyl or methylsulfonyl. More preferably, $R^d$ is hydrogen, ethynyl, fluoro, chloro, methyl, methoxy, methylthio or methylsulfonyl and $R^{d2}$ is hydrogen.

Most preferably, $R^{d1}$ is methoxy, $R^d$ is hydrogen or methyl, fluoro, chloro, or methoxy and $R^{d2}$ is hydrogen.

(ii) Preferably, $R^2$ is a group of formula:

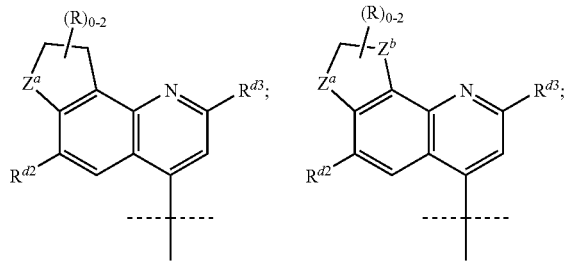

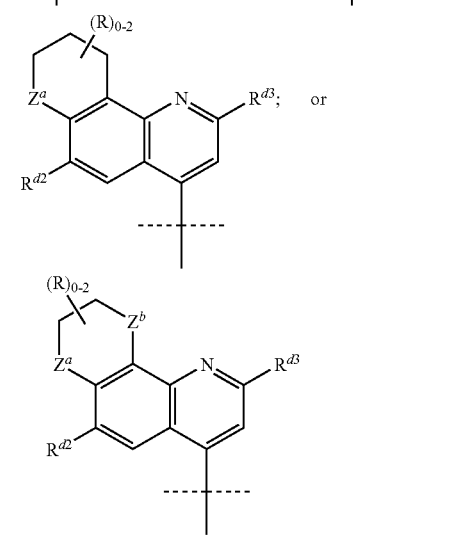

where:
$Z^a$ and $Z^b$ are independently —O— or —NH— where the H can be replaced by R, preferably —O—;
R is alkyl, preferably methyl;
$R^{d2}$ is hydrogen or methyl, preferably hydrogen; and
$R^{d3}$ is as defined for subgroup (i) immediately above.

(iii) Preferably, $R^2$ is a group of formula:

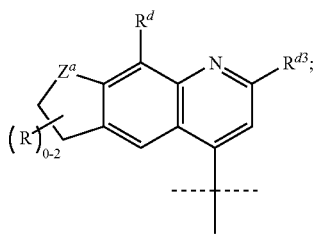

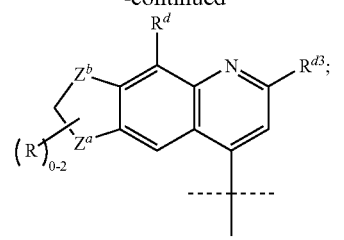

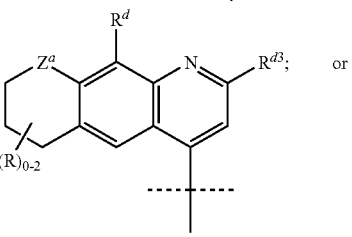

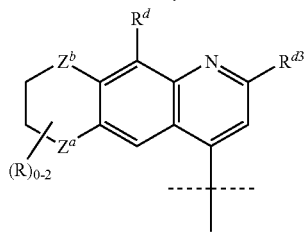

$Z^a$ and $Z^b$ are independently —O— or —NH—H can be replaced by R, preferably —O—;
R is alkyl, preferably methyl;
$R^d$ is hydrogen or methyl, preferably hydrogen; and
$R^{d3}$ is as defined for subgroup (i) above.

Within the above groups (i)-(iii), and more preferred groups contained therein, a more preferred group of compounds is that wherein the $R^{d3}$ rings are optionally substituted with methyl, ethyl, n-propyl, i-propyl, n-butyl, 1-methylpropyl, 2-methylpropyl, tert-butyl, 2,2,dimethylpropyl, 1,2-dimethylpropyl, 1,2,2-trimethylpropyl, cyclopropyl, cyclobutyl, cyclopentyl, cyclohexyl, cyclopropylmethyl, cyclobutylmethyl, cyclopentylmethyl and cyclohexylmethyl each of said cycloalkyl and cycloalkylalkyl rings being optionally substituted with one to three substituents independently selected from methyl or ethyl, preferably methyl.

Within the above groups (i)-(iii), and more preferred groups contained therein, a more preferred group of compounds is that wherein the $R^{d3}$ rings are optionally substituted with amino, methylamino, ethylamino, propylamino, 1-methylethylamino, 1,1-dimethylethylamino, 2-methylpropylamino, 1-methylpropylamino, 2,2-dimethylpropylamino, 1,2-dimethylpropylamino, 1,1-dimethylpropylamino, cyclopropylamino, cyclobutylamino, cyclopentylamino, cyclohexylamino, cyclopropylmethylamino, cyclobutylmethylamino, cyclopentylmethylamino, cyclohexylmethylamino, methylcarbonylamino, ethylcarbonylamino, propylcarbonylamino, 1-methylethylcarbonylamino, 1,1-dimethylethylcarbonylamino, 2-methylpropylcarbonylamino, 1-methylpropylcarbonylamino, 2,2-dimethylpropylcarbonylamino, 1,2-dimethylpropylcarbonylamino, 1,1-dimethylpropylcarbonylamino, cyclopropylcarbonylamino, cyclobutylcarbonylamino, cyclopentylcarbonylamino, cyclohexylcarbonylamino, cyclopropylmethylcarbonylamino, cyclobutylmethylcarbonylamino, cyclopentylmethylcarbonylamino, cyclohexylmethylcarbonylamino, methoxycarbonylamino, ethoxycarbonylamino, propoxycarbonylamino, 1-methylethoxycarbonylamino, 1,1-dimethyl-ethoxycarbonylamino, 2-methylpropoxycarbonylamino, 1-methylpropoxycarbonylamino, 2,2-dimethylpropoxycarbonylamino, 1,2-dimethylpropoxylcarbonylamino, or 1,1-dimethylpropoxy-carbonylamino.

(1) Within the above preferred group (C) and more preferred groups contained therein, an even more preferred group of compounds is that wherein:

X is —O—;
$R^1$ is alkyl optionally substituted with alkoxy, alkylthio, or alkylsulfonyl, alkenyl, alkynyl, or cycloalkylalkyl, preferably alkyl or cycloalkylalkyl, preferably methyl, ethyl, n-propyl, n-butyl, n-pentyl, prop-2-enyl, propyn-2-yl, 1-methylethyl, 1-methylpropyl, 2-methylpropyl, 3-methylbutyl, cyclopropyl, methoxymethyl, 2-methoxyethyl, methylthiomethyl, methylsulfonylmethyl, or cyclobutylmethyl. More preferably cyclobutylmethyl, ethyl, or n-propyl; and
$R^3$ is alkyl, aryl or cycloalkyl, preferably, 1-methylethyl, 1-methylpropyl, tent-butyl, cyclopropyl, phenyl, or cyclohexyl. Preferably $R^3$ is tert-butyl or cyclohexyl.

(a) Within this group C and C(1) and more preferred groups contained therein a preferred group of compounds is that wherein:
E is —COCONHR$^6$ where $R^6$ is hydrogen, alkyl, cycloalkyl, aralkyl, or heteroaralkyl wherein the aromatic ring is optionally substituted with one or two halo, preferably, $R^6$ is cyclopropyl, —CH(CH$_3$)R where R is phenyl, 4-chlorophenyl, 2,4-dichlorophenyl, 2,4-difluorophenyl, 3,4-dichlorophenyl, 3,4-difluorophenyl, or pyridin-4-yl. Preferably, $R^6$ is cyclopropyl.

(b) Within this group C and C(1) and more preferred groups contained therein a preferred group of compounds is that wherein:
E is —COCOOR$^{10}$ where $R^{10}$ is as defined in the Summary of the Invention. Preferably, $R^{10}$ is —CH$_2$C≡CH, —CH$_2$CH═CH$_2$, n-propyl, 2,2-dimethylpropyl, carboxymethyl, methoxycarbonylmethyl, tert-butoxycarbonylmethyl, —CH$_2$C(O)OCH$_2$C≡CH, —CH$_2$C(O)OCH$_2$CH═CH$_2$, —CH$_2$C(O)O(CH$_2$)$_2$CH$_3$, —CH$_2$C(O)NH$_2$, —CH$_2$C(O)NHCH$_3$, —CH$_2$C(O)N(CH$_3$)$_2$, —CH$_2$C(O)NHCH$_2$CH═CH$_2$, or 2-phenethyl.

(D) Yet another preferred group of compounds of Formula (I) is that wherein $R^2$ is a group of formula (b):

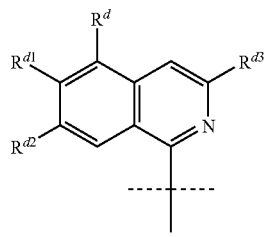

(b)

where:
$R^{d1}$ is hydrogen, hydroxy, alkoxy, amino, alkylamino, dialkylamino, haloalkoxy or alkylsulfonyl;
$R^d$ and $R^{d2}$ are independently hydrogen, alkyl, halo, alkoxy, alkylthio, or alkylsulfonyl; or
$R^{d1}$ and $R^d$ or $R^{d1}$ and $R^{d2}$ together with the carbon atoms to which they are attached form 4, 5, or 6-atom heterocyclyl ring wherein one or two ring atoms are replaced by oxygen or —N— where the heterocyclyl ring is optionally substituted with one or two alkyl;
$R^{d3}$ is hydrogen, alkyl, cycloalkyl or cycloalkylalkyl.

(i) Preferably,
$R^{d1}$ is hydrogen, hydroxy, alkoxy, amino, alkylamino or dialkylamino;
$R^d$ and $R^{d2}$ are independently hydrogen, alkyl, halo, alkoxy, alkylthio, or alkylsulfonyl; and
$R^{d3}$ is a hydrogen, alkyl or cycloalkyl.

Within the above preferred groups, a more preferred group of compounds is that wherein:
$R^{d1}$ is hydrogen, hydroxy, methoxy, ethoxy, n-propoxy, isopropoxy, methylamino, ethylamino, n-propylamino, isopropylamino, dimethylamino, methylethylamino, methyl(n-propyl)amino and methyl(isopropyl)amino; more preferably, hydrogen hydroxyl; methoxy or dimethylamino, even more preferably methoxy. Alternatively, even more preferably hydrogen;
$R^d$ and $R^{d2}$ are independently, fluoro, chloro, methyl, ethynyl, methoxy, ethoxy, thiomethyl or methylsulfonyl. More preferably, $R^d$ is hydrogen, ethynyl, fluoro, chloro, methyl, methoxy, methylthio or methylsulfonyl and $R^{d2}$ is hydrogen.

Most preferably, $R^{d1}$ is methoxy, $R^d$ is hydrogen or methyl, fluoro, chloro, or methoxy and $R^{d2}$ is hydrogen.

(1) Within the above preferred group (D) and more preferred groups contained therein, an even more preferred group of compounds is that wherein:

X is —O—;
$R^1$ is alkyl optionally substituted with alkoxy, alkylthio, or alkylsulfonyl, alkenyl, alkynyl, or cycloalkylalkyl, preferably alkyl or cycloalkylalkyl, preferably methyl, ethyl, n-propyl, n-butyl, n-pentyl, prop-2-enyl, propyn-2-yl, 1-methylethyl, 1-methylpropyl, 2-methylpropyl, 3-methylbutyl, cyclopropyl, methoxymethyl, 2-methoxyethyl, methylthiomethyl, methylsulfonylmethyl, or cyclobutylmethyl. More preferably cyclobutylmethyl, ethyl, or n-propyl; and
$R^3$ is alkyl, aryl or cycloalkyl, preferably, 1-methylethyl, 1-methylpropyl, tent-butyl, cyclopropyl, phenyl, or cyclohexyl. Preferably $R^3$ is tert-butyl or cyclohexyl.

(a) Within this group D and D(1) and more preferred groups contained therein a preferred group of compounds is that wherein:
E is —COCONHR$^6$ where $R^6$ is hydrogen, alkyl, cycloalkyl, aralkyl, or heteroaralkyl wherein the aromatic ring is optionally substituted with one or two halo, preferably, $R^6$ is cyclopropyl, —CH(CH$_3$)R where R is phenyl, 4-chlorophenyl, 2,4-dichlorophenyl, 2,4-difluorophenyl, 3,4-dichlorophenyl, 3,4-difluorophenyl, or pyridin-4-yl. Preferably, $R^6$ is cyclopropyl.

(b) Within this group D and D(1) and more preferred groups contained therein a preferred group of compounds is that wherein:
E is —COCOOR$^{10}$ where $R^{10}$ is as defined in the Summary of the Invention. Preferably, $R^{10}$ is —CH$_2$CH═CH$_2$, n-propyl, 2,2-dimethylpropyl, carboxymethyl, methoxycarbonylmethyl, tert-butoxycarbonylmethyl, —CH$_2$C(O)OCH$_2$C≡CH, —CH$_2$C(O)OCH$_2$CH═CH$_2$, —CH$_2$C(O)O(CH$_2$)$_2$CH$_3$, —CH$_2$C(O)NH$_2$, —CH$_2$C(O)NHCH$_3$, —CH$_2$C(O)N(CH$_3$)$_2$, —CH$_2$C(O)NHCH$_2$CH═CH$_2$, or 2-phenethyl.

It should be noted that reference to the preferred embodiments set forth above includes all combinations of particular and preferred groups unless stated otherwise.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1999.

Compounds of Formula (I) where Y is —OC(O)NH—, E is —COCONR$^5$R$^6$ and X, R$^1$, R$^2$, R$^3$, and R$^4$ are as defined in the Summary of the Invention can be prepared by proceeding as in the following Reaction Scheme 1 below.

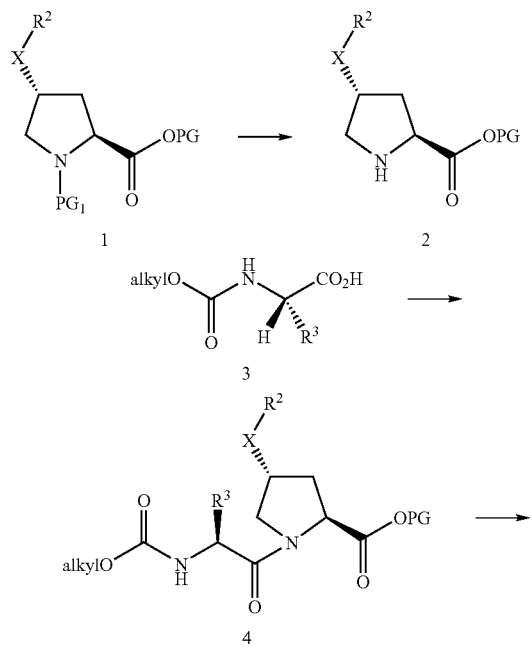

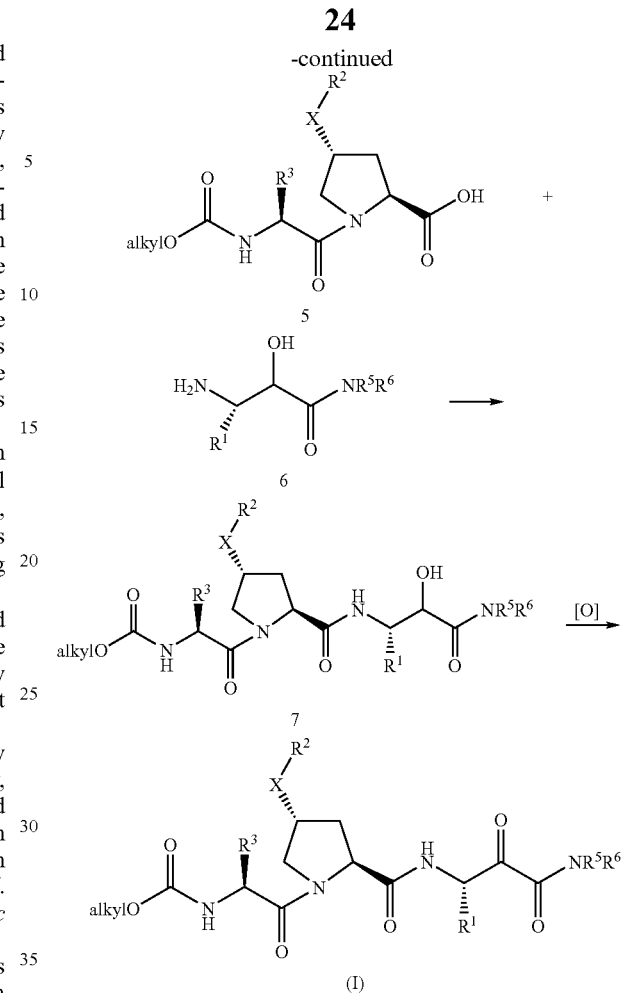

Deprotection of the amino protecting group PG$_1$ such as tert-butoxycarbonyl, benzyloxycarbonyl, and the like, in a pyrrolidine compound of formula 1 where PG is a suitable carboxy protecting group, preferably alkyl, and X and R$^2$ are as defined in the Summary of the Invention provides a compound of formula 2. The reaction conditions employed for the amino protecting group depends on the nature of the protecting group. For example, if PG$_1$ is tert-butoxycarbonyl, it is removed by treatment of 1 with an acid such as hydrochloric acid in an organic solvent such as dioxane, tetrahydrofuran, and the like. Other suitable nitrogen protecting groups with reaction conditions for putting them on and removing them can be found in Greene, T. W.; and Wuts, P. G. M.; Protecting Groups in Organic Synthesis; John Wiley & Sons, Inc. 1999. Compounds of formula 1 can be prepared by methods well known in the art. Some such methods are described in US 2003191067, U.S. Pat. No. 6,608,027, U.S. Pat. No. 6,268,207, U.S. Pat. No. 6,404,397, U.S. Pat. No. 6,268,207, and WO 2005/028501, the disclosures of which are incorporated herein by reference in their entirety.

Treatment of compound 2 with an amino acid of formula 3 where R$^3$ is as defined in the Summary of the Invention under peptidic coupling reaction conditions provides a compound of formula 4 where Y is —O—C(O)NH— and R$^4$ is alkyl. The reaction is typically carried out in the presence of a suitable coupling agent e.g., benzotriazole-1-yloxytrispyrrolidinophosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), or 1,3-dicyclohexyl-carbodiimide (DCC), optionally in the presence of 1-hydroxy-benzotriazole (HOBT), and a base such as N,N-diisopropylethylamine, triethylamine, N-methylmorpholine, and the like. The reaction is typically carried out at 20 to 30° C., preferably at about 25° C. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like or mixtures thereof. Amino acids of formula 3 are either commercially available or they can be prepared by methods well known in the art.

Hydrolysis of the ester group in compound 4 (PG=alkyl) under aqueous basic hydrolysis reaction conditions provides a compound of formula 5. The reaction is typically carried out with cesium carbonate, lithium hydroxide, sodium hydroxide, and the like in an aqueous alcohol such as methanol, ethanol, and the like.

Treatment of compound 5 with an α-hydroxyaminocarboxamide of formula 6 under peptidic coupling reaction conditions as described above provides a compound of formula 7. Compounds of formula 6 can be prepared by methods well known in the art some of which are described in details in working examples, References A and B below. Compound 6 can also be prepared from compound 17 (whose synthesis is described in Scheme 3 below). Briefly, after suitable protection of the amino group (for example as the t-Boc carbamate), the ester group of compound 17 is removed under basic hydrolysis reaction conditions to form the corresponding α-hydroxy acid. Treatment of the acid with an amine of formula NHR$^5$R$^6$ under coupling reaction conditions followed by acid catalyzed hydrolysis of the amine protecting group provides a compound of formula 6.

Alternatively, the above coupling step can be carried out by first converting 5 into an active acid derivative such as acid halide, succinimide ester, and the like, and then reacting it with an α-hydroxyketoamide of formula 6. The conditions utilized in this reaction depend on the nature of the active acid derivative. For example, if it is an acid chloride derivative of 5, the reaction is carried out in the presence of a suitable base (e.g. triethylamine, diisopropylethylamine, pyridine, and the like). Suitable reaction solvents are polar organic solvents such as acetonitrile, N,N-dimethylformamide, dichloromethane, or any suitable mixtures thereof. Oxidation of the hydroxy group in compound 8 with a suitable oxidizing agent such as Dess Martin Periodinane provides a compound of Formula (I).

Compounds of Formula (I) where Y is —NHC(O)NH—, E is —COCONR$^5$R$^6$ and X, R$^1$, R$^2$, R$^3$, and R$^4$ are as defined in the Summary of the Invention can be prepared by proceeding as in the following Reaction Scheme 2 below.

Reaction Scheme 2

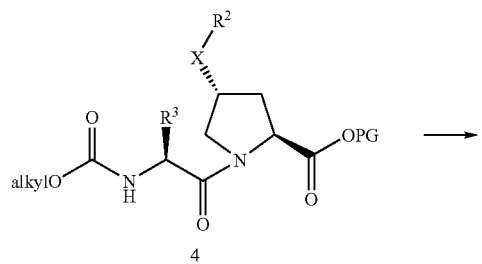

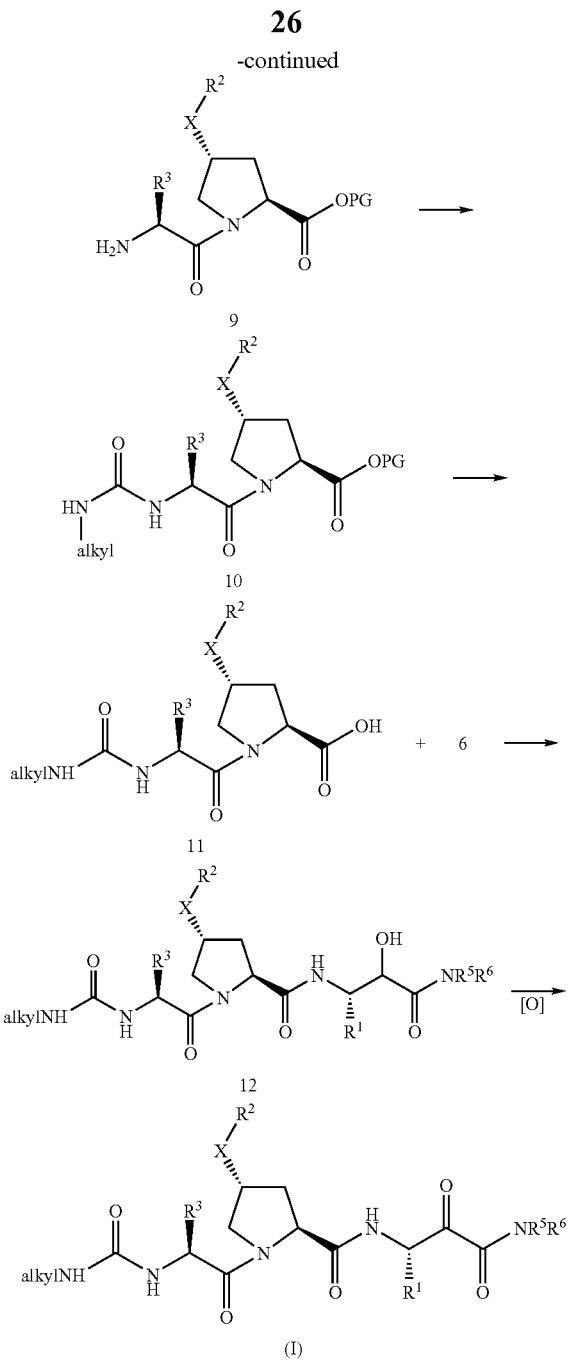

Removal of the Boc group in compound 4 under acid hydrolysis reaction conditions provides an amino compound of formula 9 which upon reaction with an alkyl isocyanate provides a ureido compound of formula 10. The reaction is carried out in the presence of an organic base such triethylamine, pyridine, and the like and in a suitable organic solvent such as dichloromethane, and the like. The ureido compounds can also be prepared by other methods well known in the art such as reaction of compound 9 with carbamoyl halides. Compound 10 is then converted to a compound of Formula (I) by proceeding as described in Scheme 1 above. Similarly compounds of Formula (I) where R$^4$ is other than alkyl can be prepared by substituting alkyl isocyanate with aryl-, heteroaryl-, or aralkyl-isocyanates or carbamyl halides.

Similarly, compound of Formula (I) where Y is —CONH— or —SO$_2$NH— can be prepared by reacting compound 9 with an acylating agent or formula R⁴COL respectively under conditions well known in the art.

Alternatively, compounds of Formula (I) can be prepared from compound 4 by deprotecting the acid protecting group to give the corresponding acid. The acid is reacted with the α-hydroxyaminocarboxamide 6 followed by removal of the Boc [alkylOC(O)-] group in the resulting product to give the free amino compound. Reaction of the amino compound with alkyl isocyanates or carbamyl halide gives compound 12 which is then converted to compound of Formula (I) upon oxidation of the hydroxyl group as described above.

Compounds of Formula (I) where E is —COCOOR¹⁰ and X, Y, R¹, R², R³, R⁴, and R¹⁰ are as defined in the Summary of the Invention can be prepared by proceeding as in the following Reaction Scheme 3 below.

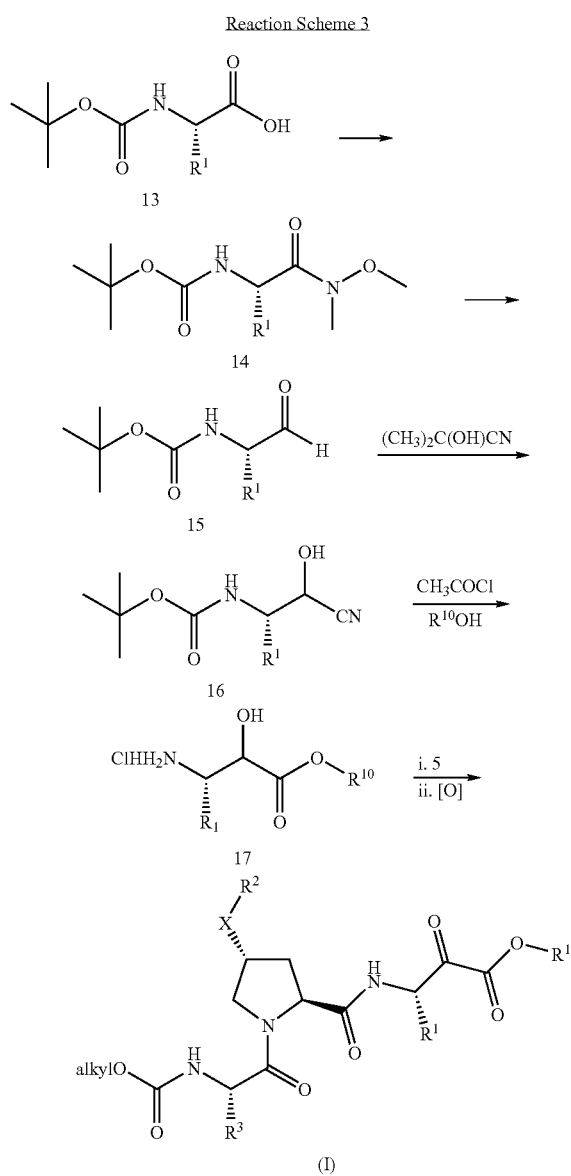

Treatment of a N-Boc-protected amino acid compound of formula 13 with N,O-dimethylamine under conditions well known in the art provides the Weinreb amide compound of formula 14. Compounds of formula 13 can be prepared from commercially available amino acids with tert-butoxycarbonyl anhydride under conditions well known in the art. Other suitable amino protecting groups can be utilized as well. Treatment of compound 14 with a suitable reducing agent such as lithium aluminium hydride in a suitable organic solvent such as tetrahydrofuran, and the like provides the corresponding aldehyde of formula 15. Treatment of compound 15 with acetone cyanohydrin provides compound 16 which is then reacted with acid halide in a hydroxyl compound of formula R¹⁰OH where R¹⁰ is as defined in the Summary of the Invention to give the alpha hydroxyl ester compound of formula 17.

Treatment of compound 17 with a compound of formula 5, under peptide coupling conditions as described earlier, followed by oxidation of the hydroxyl group in the resulting product provides a compound of Formula (I) where Y is —OC(O)NH— and R⁴ is alkyl. Compound of Formula (I) where Y is —OC(O)NH— and R⁴ is alkyl can be converted to other compounds of Formula (I) where Y and R⁴ are as defined in the Summary of the Invention as described above.

Compounds of Formula (I) where E is —CONR¹¹R¹² and X, Y, R¹, R², R³, R⁴, R¹¹, and R¹² are as defined in the Summary of the Invention can be prepared by proceeding as in the following Reaction Scheme 4 below.

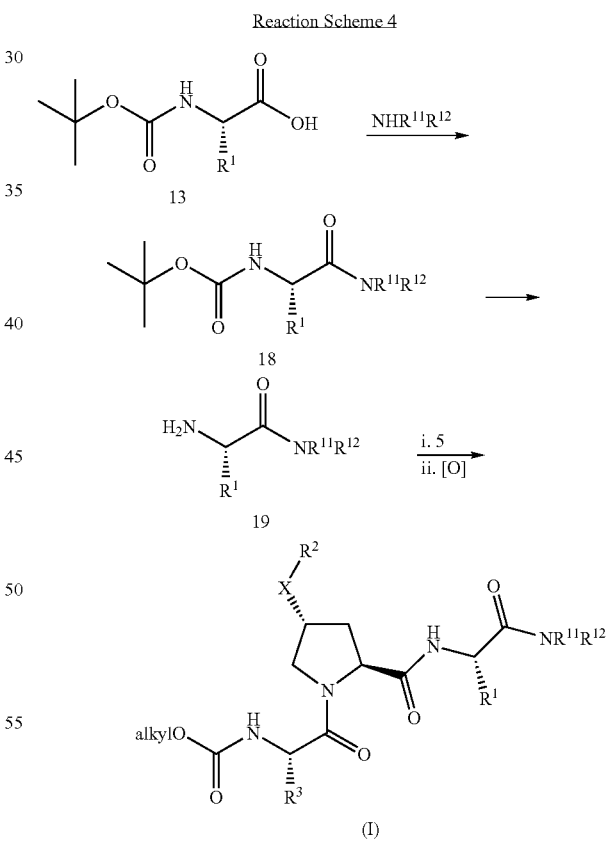

Treatment of compound 13 with an amine of formula NHR¹¹R¹² under coupling reaction conditions described above provides a compound of formula 18. Removal of the Boc group under acidic hydrolysis reaction conditions provides compound 19 which is then converted to compound of Formula (I) as described above.

Compounds of Formula (I) where E is —COR⁹ and X, Y, $R^1$, $R^2$, $R^3$, $R^4$, and $R^9$ are as defined in the Summary of the Invention can be prepared by proceeding as in the following Reaction Scheme 5 below.

Reaction Scheme 5

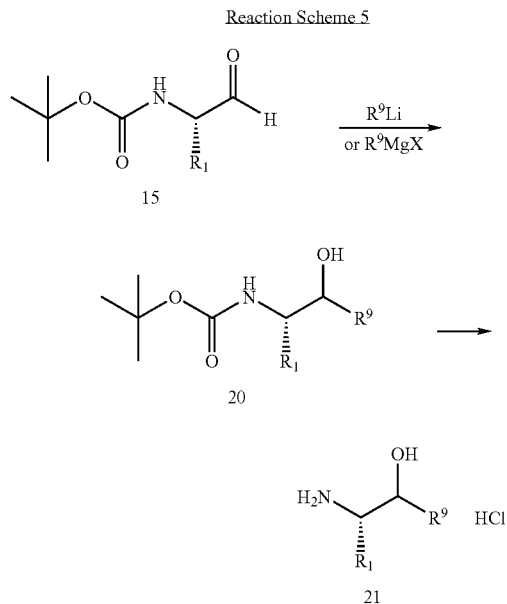

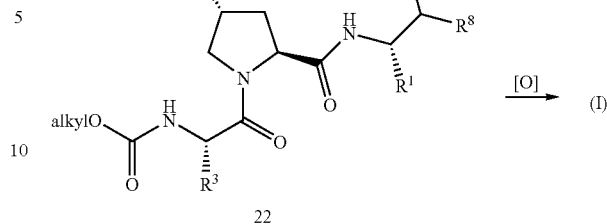

Treatment of a compound of formula 15 with an organolithium or Grignard reagent of formula $R^9Li$ or $R^9MgX$ respectively where $R^9$ is as defined in the Summary of the Invention provides a compound of formula 20. The reaction is typically carried out at low reaction temperatures such as −78° C. and in an organic solvent such as tetrahydrofuran, and the like. Removal of the Boc group provides compound 21 with upon reaction with compound 5 under coupling reaction conditions described above provides a compound of formula 22. Oxidation of the hydroxyl group then provides a compound of Formula (I) where Y is —OC(O)NH— and $R^4$ is alkyl. Compounds of Formula (I) where Y and $R^4$ are other groups as defined in the Summary of the Invention can be prepared as described above.

Compounds of Formula (I) where E is —CHO and X, Y, $R^1$, $R^2$, $R^3$, $R^4$, and $R^8$ are as defined in the Summary of the Invention can be prepared by proceeding as in the following Reaction Scheme 6 below.

Reaction Scheme 6

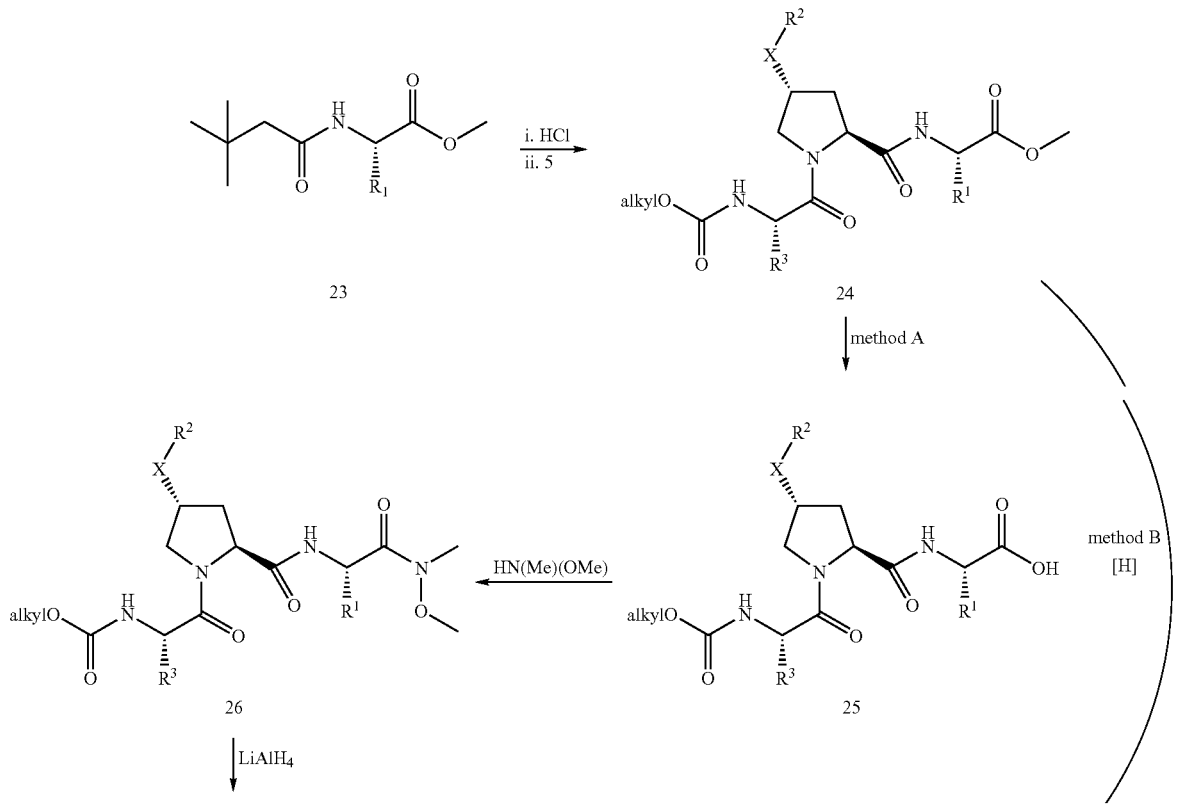

-continued

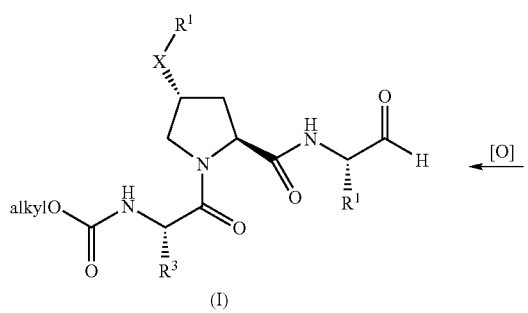
(I)

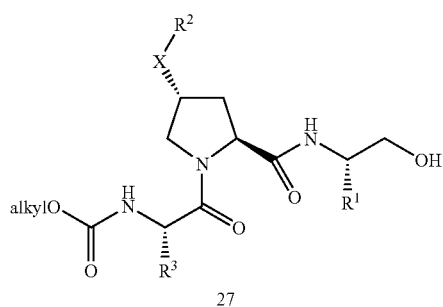
27

Removal of the amino protecting group in compound 23 under acidic hydrolysis reaction conditions, followed by coupling of the resulting amino compound with a compound of formula 5 provides a compound of formula 24. Compound 24 is then converted to a compound of Formula (I) where E is —CHO by proceeding as shown in method A or B above.

In method A, hydrolysis of the ester group under basic hydrolysis reaction conditions provides a compound of formula 25 which is converted to a Weinreb amide of formula 26. Reduction of the amido group in 26 with a suitable reducing agent such as lithium aluminum hydride then provides a compound of Formula (I) where E is —CHO and Y is —OC(O)NH—.

Alternatively, the ester group in compound 24 can be reduced with a suitable reducing agent such as lithium aluminum hydride to provide the corresponding alcohol of formula 27 which upon treatment with an oxidizing agent provides a compound of Formula (I) where E is —CHO and Y is —OC(O)NH—. Compounds of Formula (I) where Y is other groups can be prepared as described above.

A compound of Formula (I) can be converted to other compounds of Formula (I). For example:

A compound of Formula (I) containing a hydroxy group may be prepared by de-alkylation/benzylation of an alkoxy/benzyloxy substituent; those containing an acid group, by hydrolysis of an ester group; and those containing a cyano, by displacement of a bromine atom on the corresponding compounds of Formula (I). A compound of Formula (I) containing a cyano group can be converted to a corresponding carboxy containing compound by hydrolysis of the cyano group. The carboxy group, in turn, can be converted to an ester group.

A compound of Formula (I) can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula (I) can be prepared by reacting the free acid form of the compound with a pharmaceutically acceptable inorganic or organic base. Inorganic and organic acids and bases suitable for the preparation of the pharmaceutically acceptable salts of compounds of Formula (I) are set forth in the definitions section of this Application. Alternatively, the salt forms of the compounds of Formula (I) can be prepared using salts of the starting materials or intermediates.

The free acid or free base forms of the compounds of Formula (I) can be prepared from the corresponding base addition salt or acid addition salt form. For example, a compound of Formula (I) in an acid addition salt form can be converted to the corresponding free base by treating with a suitable base (e.g., ammonium hydroxide solution, sodium hydroxide, and the like). A compound of Formula (I) in a base addition salt form can be converted to the corresponding free acid by treating with a suitable acid (e.g., hydrochloric acid, etc).

The N-oxides of compounds of Formula (I) can be prepared by methods known to those of ordinary skill in the art. For example, N-oxides can be prepared by treating an unoxidized form of the compound of Formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of Formula (I) can be prepared from the N-oxide of an appropriate starting material.

Compounds of Formula (I) in unoxidized form can be prepared from N-oxides of compounds of Formula (I) by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g., acetonitrile, ethanol, aqueous dioxane, or the like) at 0 to 80° C.

Prodrug derivatives of the compounds of Formula (I) can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound of Formula (I) with a suitable carbamylating agent (e.g., 1,1-acyloxyalkylcarbonochloridate, para-nitrophenyl carbonate, or the like).

Protected derivatives of the compounds of Formula (I) can be made by means known to those of ordinary skill in the art. A detailed description of the techniques applicable to the creation of protecting groups and their removal can be found in T. W. Greene, *Protecting Groups in Organic Synthesis*, 3$^{rd}$ edition, John Wiley & Sons, Inc. 1999.

Compounds of the present invention may be conveniently prepared or formed during the process of the invention, as solvates (e.g. hydrates). Hydrates of compounds of the present invention may be conveniently prepared by recrystallisation from an aqueous/organic solvent mixture, using organic solvents such as dioxin, tetrahydrofuran or methanol.

Compounds of Formula (I) can be prepared as diastereomers that have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure isomer is then recovered by any practical means that would not result in racemization of its chiral centers. A more detailed description of the techniques applicable to the resolution of stereoisomers of compounds from their racemic mixture can be found in Jean Jacques Andre Collet, Samuel H. Wilen, *Enantiomers, Racemates and Resolutions*, John Wiley & Sons, Inc. (1981).

Pharmacology and Utility

The compounds of the present invention are inhibitors of hepatitis C virus (HCV) replication and are therefore useful in treating hepatitis C infections. The inhibitory activities of the compounds of Formula (I) can be determined by methods known to those of ordinary skill in the art. A suitable in vitro assay for measuring the ability of compounds of this invention to inhibit HCV replication is set forth in Biological Example 1 infra.

Administration and Pharmaceutical Compositions

In general, compounds of Formula (I) will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula (I) may range from about 10 micrograms per kilogram body weight (μg/kg) per day to about 100 milligram per kilogram body weight (mg/kg) per day, typically from about 100 μg/kg/day to about 10 mg/kg/day. Therefore, a therapeutically effective amount for an 80 kg human patient may range from about 1 mg/day to about 8 g/day, typically from about 1 mg/day to about 800 mg/day. In general, one of ordinary skill in the art, acting in reliance upon personal knowledge and the disclosure of this Application, will be able to ascertain a therapeutically effective amount of a compound of Formula (I) for treating a given disease.

The compounds of Formula (I) can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula (I) in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of Formula (I) in the composition may vary widely depending upon the type of formulation, size of a unit dosage, kind of excipients and other factors known to those of skill in the art of pharmaceutical sciences. In general, a composition of a compound of Formula (I) for treating a given disease will comprise from 0.01% w to 90% w, preferably 5% w to 50% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula (I) are described below.

In some embodiments, the compounds of Formula (I) can be administered to a patient in need of treatement with a second antiviral agent. Examples of suitable antiviral agents are interferons, such as Intron A, Roferon A and pegylated interferons such as PEG-intron, Pegasys; Ribavirin, Viramidine, Levovirin; HCV polymerase inhibitors such as Valopicitabine, R 1626 (Roche), HCV-796 (Viropharma/Wyeth); and toll receptor agonists such as ANA-975 (Anadys). The compounds of Formula (I) can be administered in a combination with the above agents or separately. Additionally, the compounds of Formula (I) can be administered either prior to, or following, the administration of a second antiviral agent, according to a physician prescribed regimen.

EXAMPLES

The present invention is further exemplified, but not limited by, the following examples that illustrate the preparation of compounds of Formula (I) according to the invention.

Reference A

Synthesis of [1S-(cyclopropylcarbamoylhydroxymethyl)butyl]carbamic acid tert-butyl ester

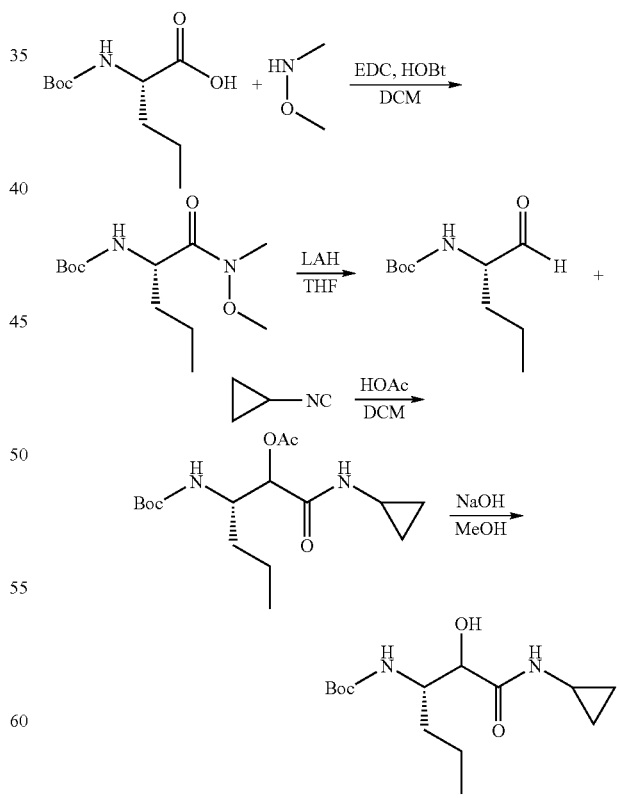

Step 1

To the mixture of Boc-NVa-OH (25 g, 0.115 mol), N,O-dimethylhydroxyamine hydrochloride (12.34 g, 0.127 mol), EDC (33.07 g, 0.173 mol), HOBt (22.9 g, 0.15 mol) in dichloromethane (300 mL), was slowly added NMM (34.9 g, 0.35 mol) under stirring in 30 min. The reaction was left at room temperature for 2 h, then diluted with 2000 mL EtOAc, washed with NaHCO₃, H₂O, and brine, and dried over MgSO₄. The solvent was removed on rotovap to give [1S-(methoxymethylcarbamoyl)butyl]carbamic acid tert-butyl ester (20 g) as colorless oil.

Step 2

To the solution of [1S-(methoxymethylcarbamoyl)butyl] carbamic acid tent-butyl ester (7.2 g, 27.7 mmol) in anhydrous THF (100 mL) under argon at −78° C., was slowly added LAH (1M in THF, 27.7 mL). After 2 h, the reaction mixture was quenched by slowly adding 1N HCl (20 mL) and then allowed to warm up to room temperature. The reaction mixture was diluted with EtOAc (600 mL), washed with 1N HCl, H₂O, and brine and dried over MgSO₄. Removal of the solvents gave (1S-formylbutyl)carbamic acid tert-butyl ester (4.8 g) as an oil.

Step 3

To a solution of cyclopropylisonitrile (1.91 g, 28.5 mmol), (1S-formylbutypcarbamic acid tert-butyl ester (3.8 g, 19 mmol) in methylene chloride (100 mL) was added acetic acid (2.28 g, 38 mmol) at 0° C. After the addition was complete the reaction mixture was allowed to warm to 25° C. and stirred for 6 h. The reaction mixture was diluted with EtOAc (200 mL), then washed with satured solution of NaHCO₃ and brine (30 mL) and dried over MgSO₄. The solvent was removed and the crude product was crystallized from 50 mL of ethyl acetate and hexane (v/v=1/1) to give acetic acid 2-tert-butoxycarbonylamino-1-cyclopropylcarbamoylpentyl ester (4.8 g) as a white solid.

Step 4

Into the solution of acetic acid 2-tert-butoxycarbonylamino-1-cyclopropylcarbamoyl-pentyl ester (4.8 g, 14.6 mmol) in methanol (50 mL) was added NaOH aqueous solution (1N, 22 mL) at room temperature. After 2 h, methanol was removed and the concentrate was extracted with ethyl acetate (300 mL). The ethyl acetate layer was washed with brine and dried over MgSO₄. After removal of the solvent, the crude product was crystallized from 100 mL of ethyl acetate and hexane (v/v=3/1) to give the title compound (3.5 g) as a white solid.

Reference B

Synthesis of (1S-cyclobutylmethyl-2-cyclopropylcarbamoyl-2-hydroxyethyl)-carbamic acid tert-butyl ester

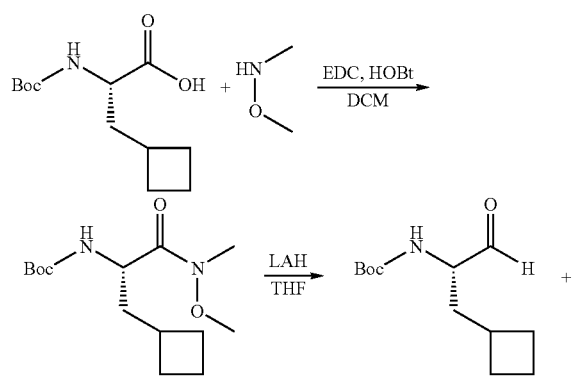

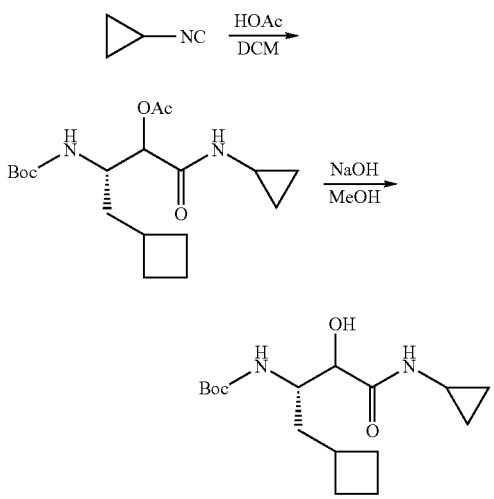

Step 1

To the mixture of Boc-L-cyclobutylalanine.DIPA (10.33 g, 30 mmol), N,O-dimethylhydroxyaminehydrochloride (3.22 g, 33 mmol), EDC (8.63 g, 45 mmol), HOBt (5.52 g, 36 mmol) in dichloromethane (200 mL), was slowly added NMM (9.11 g, 90 mmol) with stirring over 30 min. After 2 h, the reaction mixture was diluted with EtOAc (1000 mL), washed with NaHCO₃, H₂O, and brine and dried over MgSO₄. Removal of the solvent gave [2-cyclobutyl-1S-(methoxymethylcarbamoyl)ethyl]-carbamic acid tert-butyl ester (7.1 g) as a colorless oil.

Step 2

To the solution of [2-cyclobutyl-1S-(methoxymethylcarbamoypethyl]-carbamic acid tert-butyl ester (4.3 g, 15 mmol) in anhydrous THF (100 mL) under argon at −78° C., was slowly added LAH (1M in THF, 15 mL, 15 mmol). After 2 h, the reaction mixture was quenched by slowly adding 1N HCl (15 mL) and the reaction mixture was warmed up to room temperature after the addition was complete. The reaction mixture was diluted with EtOAc (500 mL), washed with 1N HCl, H₂O, and brine and dried over MgSO₄. Removal of the solvents gave (2-cyclobutyl-1S-formylethyl)carbamic acid tert-butyl ester (2.95 g) as an oil.

Step 3

To a solution of cyclopropylisonitrile (1.21 g, 18 mmol), (2-cyclobutyl-1S-formylethyl)carbamic acid tert-butyl ester (2.95 g, 13 mmol) in methylene chloride (20 mL), was added acetic acid (1.56 g, 26 mmol) at 0° C. After the addition was complete, the reaction mixture was allowed to warm to 25° C. and stirred for another 4 h. The reaction mixture was diluted with 200 mL EtOAc and washed with saturated solution of NaHCO₃ and brine and dried over MgSO₄. The solvent was removed and the crude product was crystallized from 50 mL of ethyl acetate and hexane (v/v=1/1) to give acetic acid 2S-tert-butoxycarbonylamino-3-cyclobutyl-1-cyclopropylcarbamoylpropyl ester (3.8 g) as a white solid.

Step 4

To a solution of acetic acid 2S-tert-butoxycarbonylamino-3-cyclobutyl-1-cyclopropylcarbamoylpropyl ester (3.8 g, 10.7 mmol) in methanol (50 mL) was added NaOH aqueous solution (1N, 15 mL) at room temperature. After 2 h, methanol was removed and the concentrate was extracted with ethyl acetate. The ethyl acetate was washed with brine and dried over $MgSO_4$. The solvent was removed and the residue was crystallized from 100 mL of ethyl acetate and hexane (v/v=3/1) to give the title compound (2.9 g) as a white solid.

Example 1

Synthesis of 1-[2S-(3-tert-butylureido)-3,3-dimethyl-butyryl]-4R-(7-methoxy-2-pyrazol-1-yl-quinolin-4-yloxy)-pyrrolidine-2S-carboxylic acid (1S-cyclopropylaminooxalylbutypamide (7)

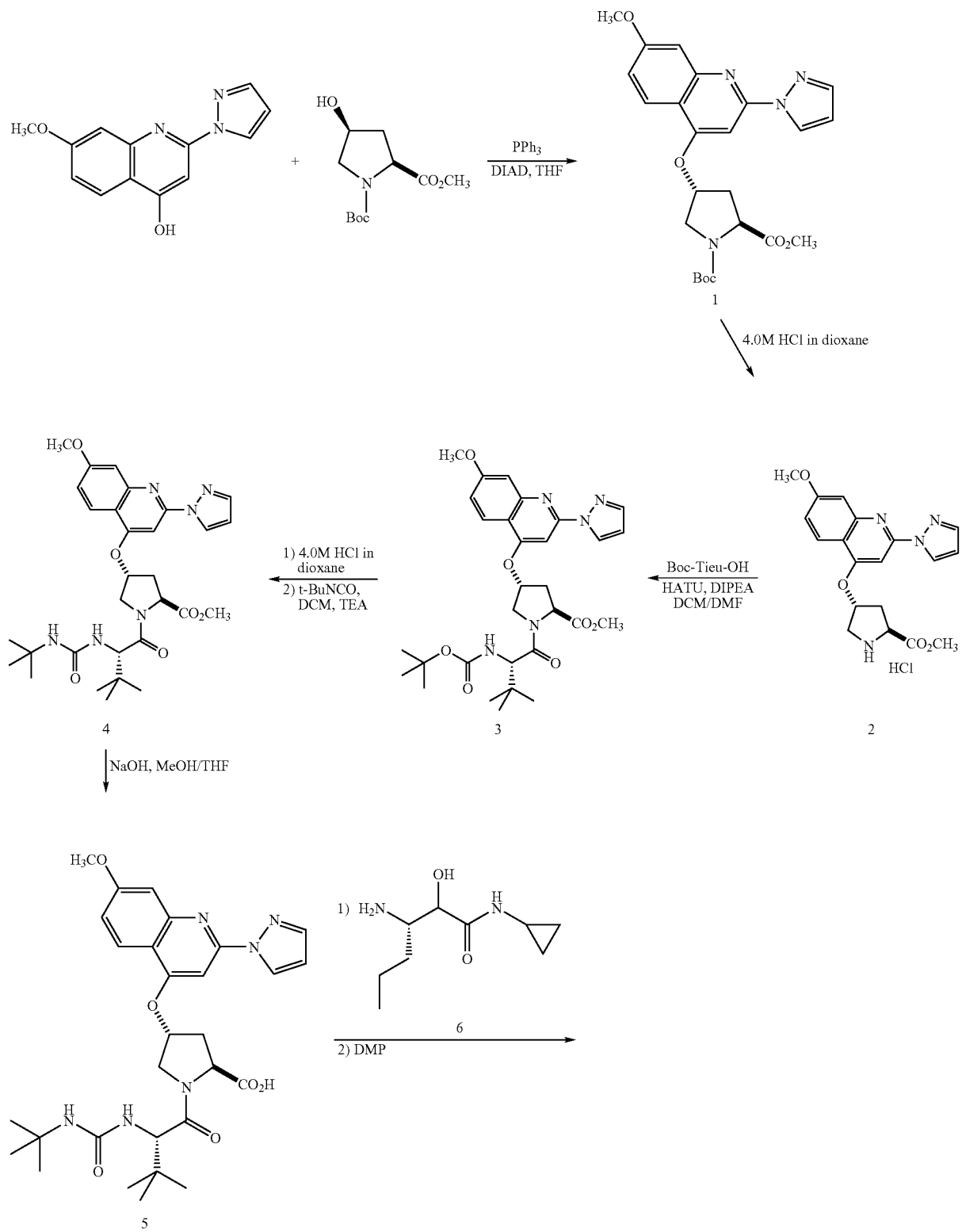

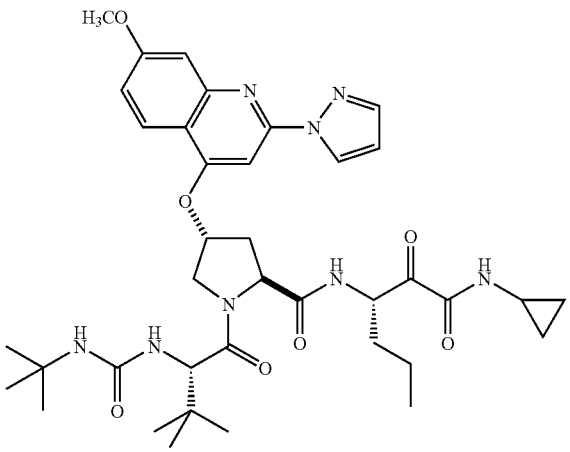

7

Step 1

To a solution of commercially available N-tert-Boc-cis-4S-hydroxy-L-proline methyl ester (370 mg, 1.51 mmol) and 7-methoxy-2-pyrazol-1-yl-quinolin-4-ol (PCT application publication No. WO 2000059929) (400 mg, 1.66 mmol) in dry THF (15 mL) at 0° C. was added triphenylphosphine (594 mg, 2.27 mmol), followed by a slow addition of DIAD (0.36 mL, 1.81 mmol) under $N_2$. The reaction mixture was slowly allowed to warm to room temperature and stirred for 18 h. The crude reaction mixture was then concentrated and purified by flash chromatography to give the 4R-(7-methoxy-2-pyrazol-1-yl-quinolin-4-yloxy)-pyrrolidine-1,2-dicarboxylic acid 1-tent-butyl ester-2S-methyl ester (1) in 69% yield.

Step 2

To a solution of 4R-(7-methoxy-2-pyrazol-1-yl-quinolin-4-yloxy)-pyrrolidine-1,2-dicarboxylic acid 1-tert-butyl ester-2S-methyl ester (200 mg, 0.43 mmol) in dichloromethane (1 mL) was added 4.0 M HCl in dioxane (3.0 mL). After 1 h, the reaction mixture was concentrated and dried to give 4R-(7-methoxy-2-pyrazol-1-yl-quinolin-4-yloxy)-pyrrolidine-2S-carboxylic acid methyl ester hydrochloride (2) as a white solid.

Step 3

To a solution of 4R-(7-methoxy-2-pyrazol-1-yl-quinolin-4-yloxy)-pyrrolidine 2S-carboxylic acid methyl ester hydrochloride (67 mg, 0.165 mmol) in dichloromethane/DMF (2.0 mL, 1:1) was added Boc-L-tert-Leu-OH (38.1 mg, 0.165 mmol), HATU (69 mg, 0.182 mmol) and DIPEA (0.1 mL, 0.5 mmol) and the mixture was stirred at rt. After 16 h, the reaction mixture was diluted with ethyl acetate and washed with 1N HCl, saturated $NaHCO_3$, and brine. The ethyl acetate layer was dried ($MgSO_4$), filtered and evaporated to dryness to give 1-(2S-tert-butoxycarbonylamino-3,3-dimethylbutyryl)-4R-(7-methoxy-2-pyrazol-1-yl-quinolin-4-yloxy)-pyrrolidine-2S-carboxylic acid methyl ester (3) in quantitative yield.

Step 4

To a solution of crude 1-(2S-tert-butoxycarbonylamino-3,3-dimethylbutyryl)-4R-(7-methoxy-2-pyrazol-1-yl-quinolin-4-yloxy)-pyrrolidine-2S-carboxylic acid methyl ester in dichloromethane (1 mL) was added 4.0 M HCl in dioxane (3.0 mL). After 1 h, the reaction mixture was concentrated and dried to give 1-(2S-amino-3,3-dimethylbutyryl)-4R-(7-methoxy-2-pyrazol-1-yl-quinolin-4-yloxy)-pyrrolidine-2S-carboxylic acid methyl ester HCl salt as a white solid which was used in the next step without further purification.

Step 5

To a solution of 1-(2S-amino-3,3-dimethylbutyryl)-4R-(7-methoxy-2-pyrazol-1-yl-quinolin-4-yloxy)-pyrrolidine-2S-carboxylic acid methyl ester HCl salt (0.165 mmol) in dichloromethane (3.0 mL) was added triethylamine (0.06 mL, 0.413 mmol) and tert-butylisocyanate (0.02 mL, 0.165 mmol) and the reaction mixture was stirred at rt. After 16 h, the reaction mixture was diluted with dichloromethane and washed with 1N HCl, saturated $NaHCO_3$, and brine. The dichloromethane layer was then evaporated to dryness to give 1-[2S-(3-tert-butyl-ureido)-3,3-dimethyl-butyryl]-4R-(7-methoxy-2-pyrazol-1-ylquinolin-4-yloxy)-pyrrolidine-2S-carboxylic acid methyl ester (4).

Step 6

1-[2S-(3-tert-Butyl-ureido)-3,3-dimethyl-butyryl]-4R-(7-methoxy-2-pyrazol-1-ylquinolin-4-yloxy)-pyrrolidine-2S-carboxylic acid methyl ester was treated with methanol (6.0 mL), THF (3.0 mL) and 1N NaOH (6. mL). After 1 h at rt, the reaction mixture was concentrated, acidified with 1N HCl and extracted with ethyl acetate. The combined ethyl acetate layers were then washed with brine and dried ($MgSO_4$). The ethyl acetate layer was then filtered and evaporated to dryness to give 1-[2S-(3-tert-butyl-ureido)-3,3-dimethyl-butyryl]-4R-(7-methoxy-2-pyrazol-1-yl-quinolin-4-yloxy)-pyrrolidine-2S-carboxylic acid (5).

Step 7

[1S-(Cyclopropylcarbamoylhydroxymethyl)butyl]carbamic acid tert-butyl ester (48 mg, 0.165 mmol) was dissolved in dichloromethane (3.0 mL) and TFA (3.0 mL) was added. After stirring for 1 h at rt, the reaction mixture was evaporated to dryness to give 3S-amino-2-hydroxyhexanoic acid cyclopropylamide TFA salt as a white solid. A solution of 1-[2S-(3-tert-butylureido)-3,3-dimethyl-butyryl]-4R-(7-methoxy-2-pyrazol-1-yl-quinolin-4-yloxy)-pyrrolidine-2S-carboxylic acid in dichloromethane/DMF (1:1. 6.0 mL) was added to 3S-amino-2-hydroxyhexanoic acid cyclopropylamide TFA salt followed by HATU (75 mg, 0.198 mmol) and DIPEA (0.1 mL, 0.7 mmol). After 24 h at rt, the reaction mixture was diluted with ethyl acetate and washed with 1N HCl, NaHCO$_3$, and brine. The ethyl acetate layer was dried (MgSO$_4$), filtered and evaporated to dryness. The crude product was then dissolved in dry dichloromethane (10.0 mL) and Dess-Martin periodinane (112 mg, 0.264 mmol) was added. After stirring at rt for 2 h, the reaction mixture was quenched with 0.26 M Na$_2$S$_2$O$_3$ in saturated NaHCO$_3$ and extracted with ethyl acetate. The combined ethyl acetate layers were then washed with saturated NaHCO$_3$ and brine. Purification by preparative HPLC gave the title compound (7) in >99% purity by HPLC.

1H NMR: (DMSO-d$_6$) δ 8.76-8.70 (m, 2H); 8.22 (d, J=6.8 Hz, 1H); 8.11 (d, J=9.6 Hz, 1H); 7.87 (d, J=1.2 Hz, 1H); 7.45 (s, 1H); 7.27 (d, J=2.4 Hz, 1H); 7.00-6.97 (dd, J=2.8 and 9.6 Hz, 1H); 6.64-6.62 (m, 1H); 5.92 (brs, 1H); 5.49 (brs, 1H); 5.00-4.96 (m, 1H); 4.55-4.49 (m, 2H); 4.18 (d, J=5.6 Hz, 1H); 3.90 (s, 3H); 3.91-3.82 (m, 1H); 3.54 (brs, 1H); 2.75-2.72 (m, 1H); 2.54-2.51 (m, 1H); 2.17-2.14 (m, 1H); 1.69-1.66 (m, 1H); 1.40-1.34 (m, 3H); 1.13 (m, 9H); 0.93 (m, 9H); 0.90-0.82 (m, 3H); 0.65-0.53 (m, 4H). MS (M$^+$+1) 733.

Example 2

Synthesis of 1-[2S-(3-tert-butylureido)-3,3-dimethyl-butyryl]-4R-(7-methoxy-2-pyrazol-1-yl quinolin-4-yloxy)-pyrrolidine-2-carboxylic acid (1S-cyclobutyl-methyl-2-cyclopropylcarbamoyl-2-oxoethyl)amide (9)

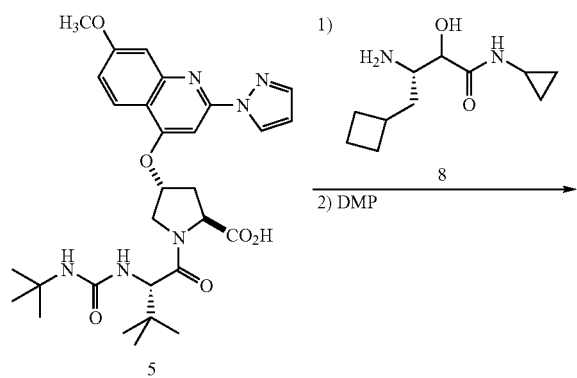

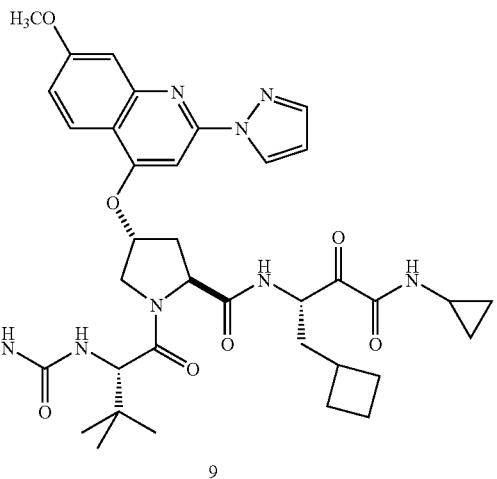

Step 1

(1S-Cyclobutylmethyl-2-cyclopropylcarbamoyl-2-hydroxy-ethyl)-carbamic acid tert-butyl ester (51 mg, 0.165 mmol) was dissolved in dichloromethane (3.0 mL) and TFA (3.0 mL) was added. After stirring for 1 h at rt, the reaction mixture was evaporated to dryness to give 3S-amino-4-cyclobutyl-N-cyclopropyl-2-hydroxy-butyramide TFA salt as a white solid. A solution of 1-[2S-(3-tert-butylureido)-3,3-dimethyl-butyryl]-4R-(7-methoxy-2-pyrazol-1-yl-quinolin-4-yloxy)-pyrrolidine-2S-carboxylic acid in dichloromethane/DMF (1:1. 6.0 mL) to added to 3S-amino-4-cyclobutyl-N-cyclopropyl-2-hydroxy-butyramide TFA salt followed by HATU (75 mg, 0.198 mmol) and DIPEA (0.1 mL, 0.7 mmol). After 24 h at rt, the reaction mixture was diluted with ethyl acetate and washed with 1N HCl, saturated NaHCO$_3$, and brine. The ethyl acetate layer was dried (MgSO$_4$), filtered and evaporated to dryness. The crude product was then dissolved in dry dichloromethane (10.0 mL) and Dess-Martin periodinane (112 mg, 0.264 mmol) was added. After stirring at rt for 2 h, the reaction mixture was quenched with 0.26M Na$_2$S$_2$O$_3$ in saturated NaHCO$_3$ and extracted with ethyl acetate. The combined ethyl acetate layers were then washed with saturated NaHCO$_3$ and brine. Purification by preparative HPLC gave the title compound (9) in >99% purity by HPLC.

$^1$H NMR: (DMSO-d$_6$) δ 8.76-8.69 (m, 2H); 8.19 (d, J=8.0 Hz, 1H); 8.10 (d, J=8.0 Hz, 1H); 7.87-7.86 (m, 1H); 7.45 (s, 1H); 7.27 (d, J=2.8 Hz, 1H); 7.00-6.97 (dd, J=2.8 and 9.6 Hz, 1H); 6.64-6.62 (m, 1H); 5.93 (brs, 1H); 5.48 (brs, 1H); 5.00-4.96 (m, 1H); 4.53-4.49 (m, 2H); 4.18 (d, J=9.2 Hz, 1H); 3.90 (s, 3H); 3.91-3.82 (m, 1H); 3.42 (brs, 2H); 2.75-2.72 (m, 1H); 2.54-2.51 (m, 1H); 2.17-2.14 (m, 1H); 1.96-1.89 (m, 2H); 1.78-1.50 (m, 6H); 1.13 (m, 9H); 0.94 (m, 9H); 0.65-0.53 (m, 4H). MS (M$^+$+1) 759.

Example 3
Synthesis of 1-[2S-(3-tert-butylureido)-3,3-dimethyl-butyryl]-4R-(5-chloropyridin-2-yloxy)-pyrrolidine-2S-carboxylic acid (1S-cyclobutylmethyl-2-cyclopropylcarbamoyl-2-oxoethyl)-amide (15)
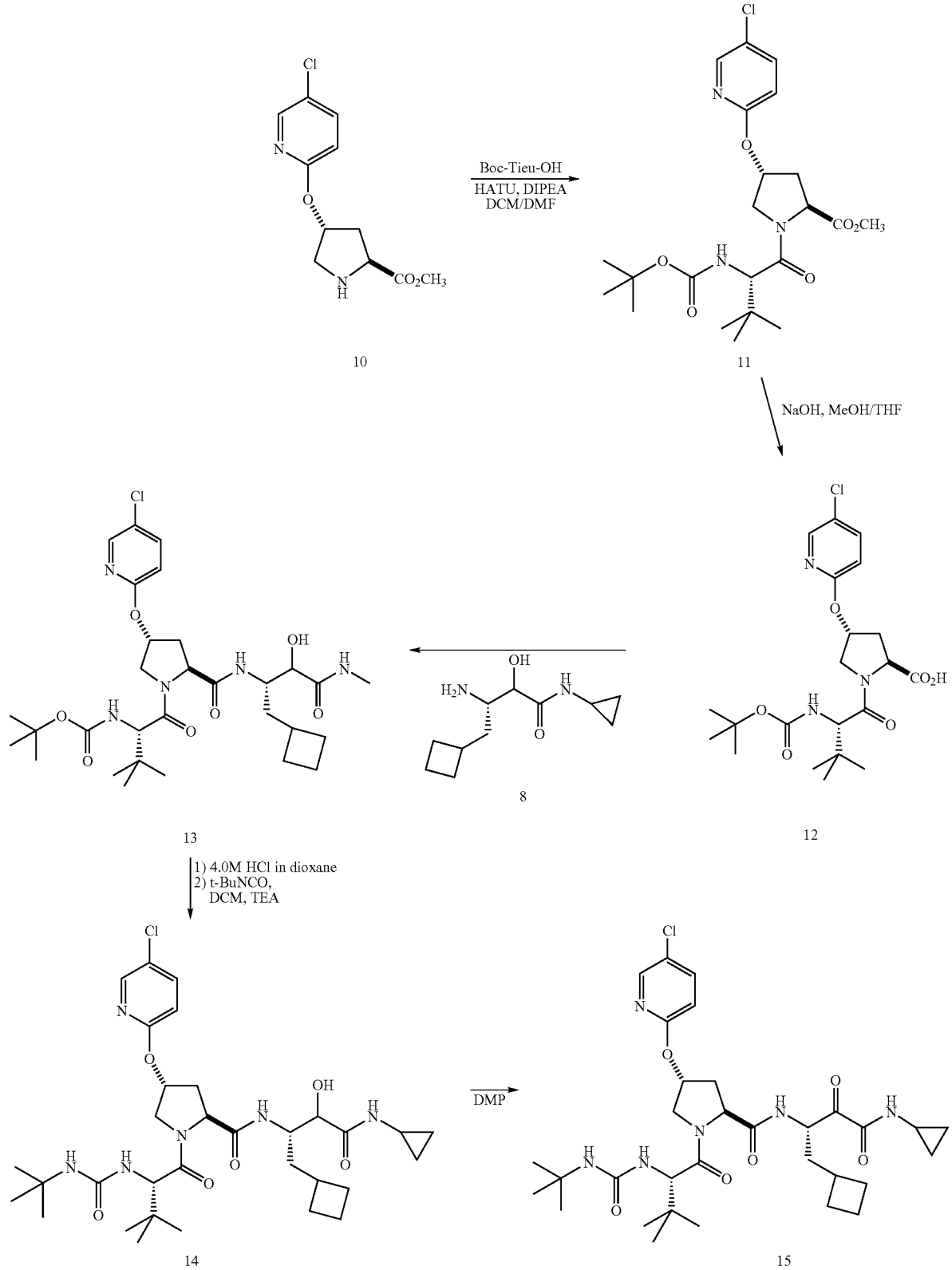

Preparation of 10, HCl Salt

To commercially available t-Boc-(2S,4R)-hydroxyproline (1 mmol) in DMSO was added potassium tert-butoxide (3 mmol) in small portions over 15 min at 23° C. The mixture was stirred at 23° C. for 30 min, then cooled to 0° C. before adding 2,5-dichloropyridine (1.1 mmol) in small portions over 10 min. The reaction mixture was stirred at 23° C. for 16 h. The resulting suspension was poured into 5% aqueous citric acid and extracted with EtOAc. The combined EtOAc layers were washed with brine and dried (MgSO$_4$). The organic portions were filtered and concentrated to give a white solid. The solid material was dissolved in 4.0 M HCl in dioxane (10 mL). After 1 h, the reaction mixture was concentrated and dried to give 4R-(5-Chloropyridin-2-yloxy)-pyrrolidine-2S-carboxylic acid methyl ester HCl salt.

Step 1

To 4R-(5-Chloropyridin-2-yloxy)-pyrrolidine-2S-carboxylic acid methyl ester HCl salt (242 mg, 0.829 mmol) in dichloromethane/DMF (10 mL, 1:1) was added Boc-L-tert-Leu-OH (192 mg, 0.829 mmol), HATU (347 mg, 0.912 mmol) and DIPEA (0.37 mL, 2.07 mmol) and the reaction mixture was stirred at rt. After 16 h, the reaction mixture was diluted with ethyl acetate and washed with saturated NaHCO$_3$, and brine. The ethyl acetate layer was dried (MgSO$_4$), filtered and evaporated to dryness to give 1-(2S-tert-butoxycarbonylamino-3,3-dimethylbutyryl)-4-(5-chloro-pyridin-2-yloxy)-pyrrolidine-2S-carboxylic acid methyl ester (11) in quantitative yield.

Step 2

1-(2S-tert-Butoxycarbonylamino-3,3-dimethylbut 1)-4R-(5-chloropyridin-2-yloxy)-pyrrolidine-2S-carboxylic acid methyl ester was treated with methanol (5.0 mL), THF (3.0 mL) and 1N NaOH (5.0 mL). After 2 h at rt, the reaction mixture was concentrated, acidified with 1N HCl and extracted with ethyl acetate. The combined ethyl acetate layers were then washed with brine and dried (MgSO$_4$). The ethyl acetate layer was then filtered and evaporated to dryness to give 1-(2S-tert-butoxycarbonylamino-3,3-dimethyl-butyryl)-4R-(5-chloro-pyridin-2-yloxy)-pyrrolidine-2S-carboxylic acid (12).

Step 3

To (1S-Cyclobutylmethyl-2-cyclopropylcarbamoyl-2-hydroxy-ethyl)-carbamic acid tert-butyl ester (214 mg, 0.83 mmol) was added 4.0 M HCl in dioxane (11.0 mL). After 1 h, the reaction mixture was concentrated and dried to give 3S-amino-4-cyclobutyl-N-cyclopropyl-2-hydroxy-butyramide HCl salt as a white solid. To 3S-amino-4-cyclobutyl-N-cyclopropyl-2-hydroxy-butyramide was added 1-(2S-tert-butoxycarbonylamino-3,3-dimethyl-butyryl)-4R-(5-chloro-pyridin-2-yloxy)-pyrrolidine-2S-carboxylic acid in dichloromethane/DMF (1:1. 10.0 mL), EDC (238 mg, 1.24 mmol), HOBt (190 mg, 1.24 mmol) and NMM (0.6 mL, 3.32 mmol). After 16 h at rt, the reaction mixture was diluted with ethyl acetate and washed with saturated NaHCO$_3$, brine, and dried (MgSO$_4$). The ethyl acetate layer was then filtered, concentrated and purified by flash chromatography to give {1-[4R-(5-chloropyridin-2-yloxy)-2S-(1S-cyclobutylmethyl-2-cyclopropylcarbamoyl-2-hydroxyethyl-carbamoyl)-pyrrolidine-1-carbonyl]-2,2-dimethyl-propyl}-carbamic acid tert-butyl ester (13) in 58% yield.

Step 4

To {1-[4R-(5-chloropyridin-2-yloxy)-2S-(1S-cyclobutylmethyl-2-cyclopropylcarbamoyl-2-hydroxyethyl-carbamoyl)-pyrrolidine-1-carbonyl]-2,2-dimethyl-propyl}-carbamic acid tert-butyl ester (313 mg, 0.482 mmol) in dichloromethane (2 mL) was added 4.0 M HCl in dioxane (3.0 mL). After 1 h, the reaction mixture was concentrated and dried to give 1-(2S-amino-3,3-dimethylbutyryl)-4R-(5-chloropyridin-2-yloxy)-pyrrolidine-2-carboxylic acid (1-cyclobutyl-methyl-2-cyclopropylcarbamoyl-2-hydroxyethyl)-amide HCl salt as a white solid.

Step 5

To a solution of 1-(2S-amino-3,3-dimethylbutyryl)-4R-(5-chloropyridin-2-yloxy)-pyrrolidine-2-carboxylic acid (1-cyclobutyl-methyl-2-cyclopropylcarbamoyl-2-hydroxyethyl)-amide HCl salt (45 mg, 0.077 mmol) in dichloromethane (3.0 mL) was added triethylamine (0.02 mL, 0.154 mmol). After 5 min at rt, tert-butylisocyanate (0.01 mL, 0.077 mmol) was added and the reaction mixture was stirred at rt. After 16 h, the reaction mixture was diluted with dichloromethane and washed with 1N HCl, saturated NaHCO$_3$, and brine. The dichloromethane layer was then evaporated to dryness to give 1-[2S-(3-tert-butyl-ureido)-3,3-dimethyl-butyryl]-4R-(5-chloropyridin-2-yloxy)-pyrrolidine-2S-carboxylic acid (1S-cyclobutylmethyl-2-cyclopropylcarbamoyl-2-hydroxyethyl)-amide (14).

Step 6

1-[2S-(3-tert-Butyl-ureido)-3,3-dimethyl-butyryl]-4R-(5-chloropyridin-2-yloxy)-pyrrolidine-2S-carboxylic acid (1S-cyclobutylmethyl-2-cyclopropylcarbamoyl-2-hydroxyethyl)-amide was dissolved in dry dichloromethane (4.0 mL) and Dess-Martin periodinane (44 mg, 0.103 mmol) was added. After stirring at rt for 2 h reaction mixture was quenched with 0.26M Na$_2$S$_2$O$_3$ in saturated NaHCO$_3$ and extracted with ethyl acetate. The combined ethyl acetate layers were then washed with saturated NaHCO$_3$ and brine. Purification by preparative HPLC gave the title compound (15) in >90% purity by HPLC.

$^1$H NMR: (DMSO) 8.91-8.73 (m, 1H); 8.30-8.24 (m, 2H); 7.92-7.7.80 (m, 1H); 6.94-6.84 (m, 1H); 5.97 (brs, 1H); 5.50 (s, 1H); 5.00-4.95 (m, 1H); 4.54-4.52 (m, 1H); 4.17-3.88 (m, 3H); 2.75-2.72 (m, 1H); 2.54-2.51 (m, 1H); 2.40-2.32 (m, 1H); 2.17-1.60 (m, 10H); 1.13 (m, 9H); 0.91 (m, 9H); 0.67-0.58 (m, 4H). MS (M$^+$+1) 648.

Example 4

Synthesis of {1S-[2S-(1S-cyclopropylaminooxalyl-butylcarbamoyl)-4R-(7-methoxy-2-pyrazol-1-yl-quinolin-4-yloxy)-pyrrolidine-1-carbonyl]-2,2-dimethylpropyl}-carbamic acid tert-butyl ester (16)

16

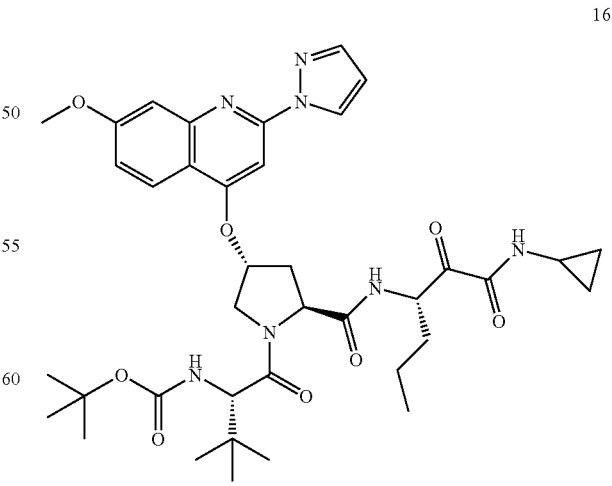

Proceeding as described in Example 1 above, provided {1S-[2R-(1S-cyclopropylamino-oxalylbutylcarbamoyl)-4R-

(7-methoxy-2-pyrazol-1-yl-quinolin-4-yloxy)-pyrrolidine-1-carbonyl]-2,2-dimethylpropyl}carbamic acid tert-butyl ester. MS: 734 (M+1)MS: 734 (M+1).

Example 5

Synthesis of {1S-[2S-(1S-cyclopropylaminooxalyl-butylcarbamoyl)-4R-(7-methoxy-2-pyrazol-1-yl-quinolin-4-yloxy)-pyrrolidine-1-carbonyl]-2,2-dimethylpropyl}-carbamic acid tert-butyl ester (17)

17

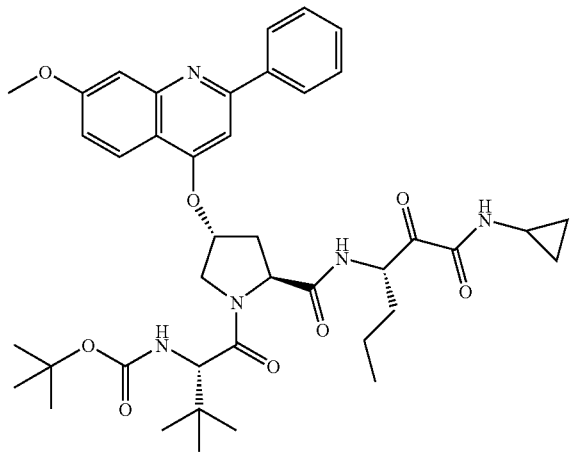

Proceeding as described in Example 4 above, but substituting 7-methoxy-2-pyrazol-1-yl-quinolin-4-ol with 7-methoxy-2-phenyl-quinolin-4-ol provided the title compound. MS: 744 (M+1)

Example 6

Synthesis of {1S-[4R-(5-chloropyridin-2-yloxy)-2S-(1S-cyclopropylaminooxalylbutyl-carbamoyl)-pyrrolidine-1-carbonyl]-2,2-dimethyl-propyl}-carbamic acid tent-butyl ester (18)

18

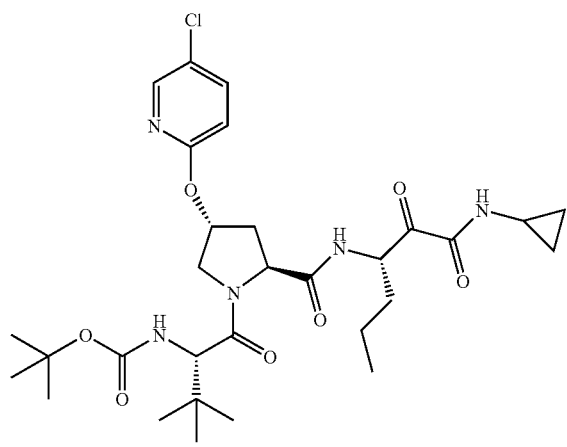

Proceeding as described in Example 4 above, but substituting 4R-(7-methoxy-2-pyrazol-1-yl-quinolin-4-yloxy)-pyrrolidine-2S-carboxylic acid methyl ester hydrochloride with 4R-(5-chloropyridin-2-yloxy)pyrrolidine-2-carboxylic acid methyl ester hydrochloride provided the title compound. MS: 622 (M+1).

Example 7

Synthesis of {1S-[4R-(5-chloropyridin-2-yloxy)-2S-(1S-cyclobutylmethyl-2-cyclopropylcarbamoyl-2-oxo-ethylcarbamoyl)-pyrrolidine-1-carbonyl]-2,2-dimethyl-propyl}-carbamic acid tert-butyl ester (19)

19

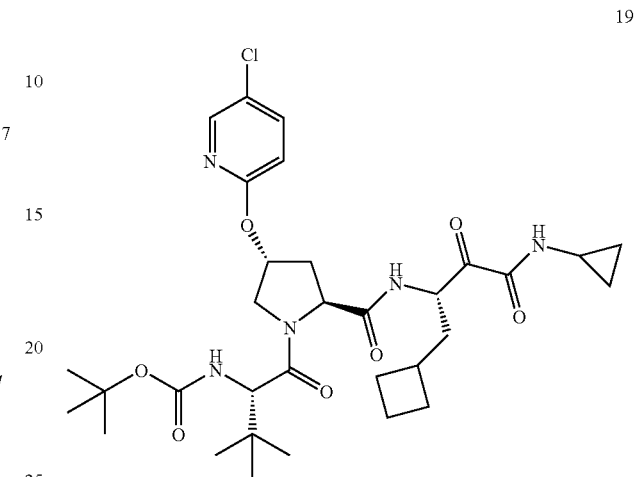

Proceeding as described in Example 4 above, but substituting 4R-(7-methoxy-2-pyrazol-1-yl-quinolin-4-yloxy)-pyrrolidine-2S-carboxylic acid methyl ester hydrochloride with 4R-(5-chloro-pyridin-2-yloxy)pyrrolidine-2-carboxylic acid methyl ester hydrochloride and (1S-cyclobutylmethyl-2-cyclopropylcarbamoyl-2-hydroxyethyl)-carbamic acid tert-butyl ester in place of [1S-(cyclopropylcarbamoylhydroxymethyl)butyl]carbamic acid tert-butyl ester provided the title compound. MS: 648 (M+1)

Example 8

Synthesis of 1-[2-(3-tert-butylureido)-3,3-dimethyl-butyryl]-4-(5-chloro-pyridin-2-yloxy)-pyrrolidine-2-carboxylic acid (1-cyclopropylaminooxalyl-butyl)-amide (20)

20

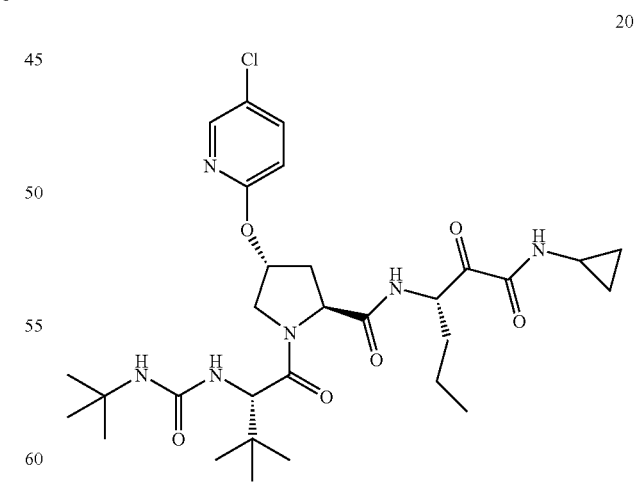

Proceeding as described in Example 3 above but substituting (1S-cyclobutylmethyl-2-cyclopropylcarbamoyl-2-hydroxyethyl)-carbamic acid tert-butyl ester with [15-(cyclopropyl-carbamoylhydroxymethyl)butyl]carbamic acid tert-butyl ester provided the title compound. MS: 621 (M+1).

Example 9

Synthesis of 1-[2S-(3-tert-Butyl-ureido)-3,3-dimethyl-butyryl]-4R-(6-methoxy-isoquinolin-1-yloxy)-pyrrolidine-2S-carboxylic acid (1S-cyclopropylaminooxalyl-butyl)-amide (21)

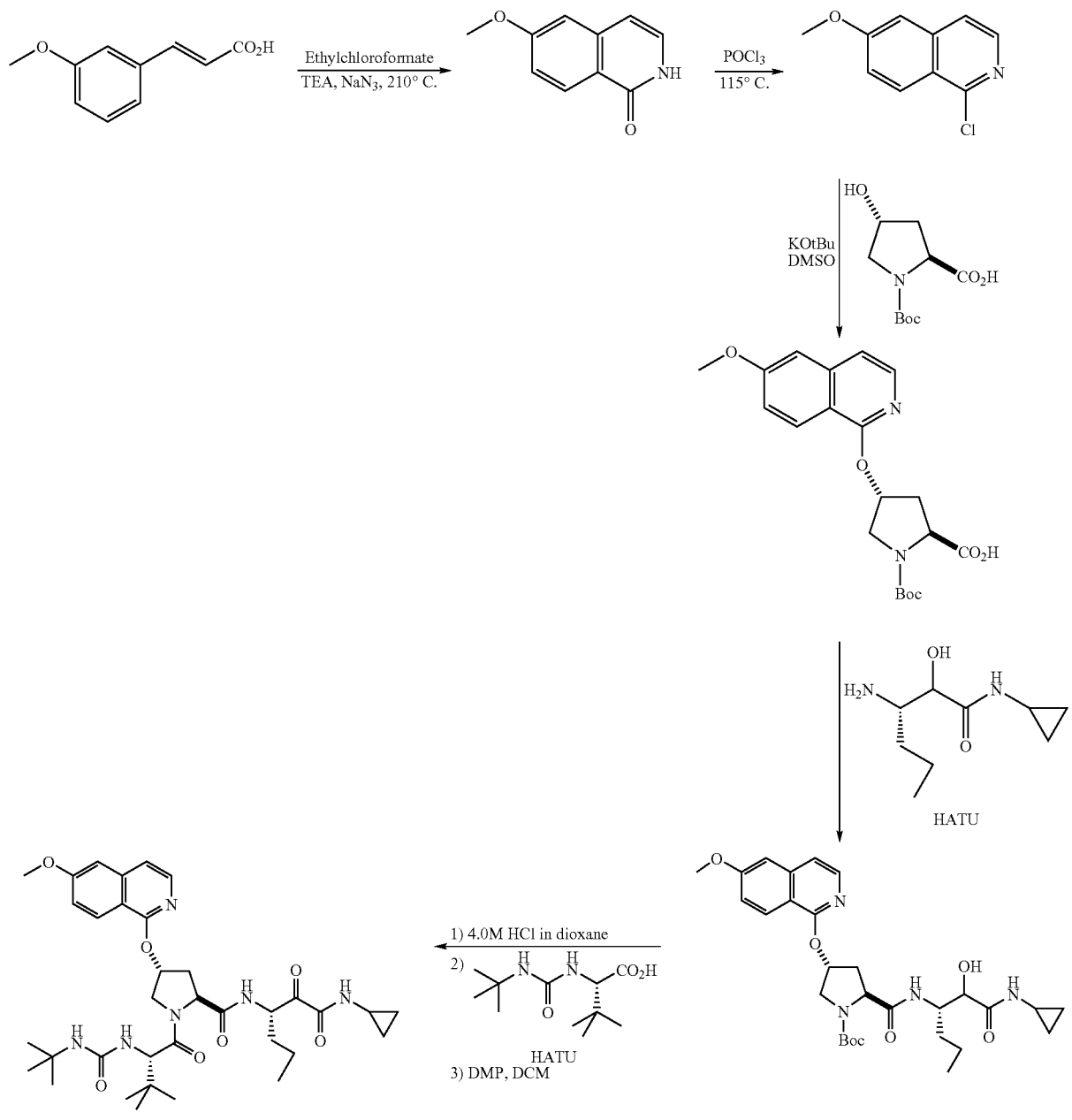

Step 1

Ethyl chloroformate (4.3 mL, 44.5 mmol) was added drop wise at 0° C. to a solution of 3-methoxy cinnamic acid (5.3 g, 29.7 mmol) and triethylamine (8.3 mL, 59.4 mmol) in acetone (35 mL). After 1 h at 0° C., aqueous sodium azide (3.1 g, 47.5 mmol, 16 mL water) was added drop wise and the reaction mixture was stirred at 23° C. for 16 h. Water (50 mL) was added to the mixture and the volatile was removed under vacuo. The resulting slurry was extracted with toluene (3×25 mL) and the combined organic layers were dried (MgSO$_4$). The dried solution was filtered and added drop wise at 190° C. to a solution of diphenylmethane (25 mL) and tributylamine (14.2 mL, 59.4 mmol). The toluene was distilled off as added. After complete addition, the reaction temperature was raised to 210° C. for 2 h. After cooling, the precipitated product was collected by filtration and washed with hexanes and dried under vacuum to yield 6-Methoxy-2H-isoquinolin-1-one (1.7 g, 9.7 mmol, 33% yield). MS m/z 176 (M$^+$+H).

Step 2

A suspension of 6-Methoxy-2H-isoquinolin-1-one (900 mgs, 5.1 mmol) in POCl$_3$ (4 mL) was heated at 110° C. for 3 h (clear solution obtained upon heating). After 3 h, the reaction mixture was concentrated under reduced pressure. The residue was poured into iced water (10 mL), pH was then adjusted to 10 with 3N NaOH and extracted with CHCl₃ (3×25 mL). The combined CHCl₃ layers were washed with brine and dried (MgSO₄). The organic layer was then filtered, concentrated and purified by flash chromatography (50% ethyl acetate/hexane) to give 1-chloro-6-methoxy-isoquinoline (720 mgs, 3.7 mmol, 73% yield) as white solid. ¹H NMR (CD₃OD): 8.23 (d, 1H, J=8.8 Hz); 8.11 (d, 1H, J=6.0 Hz); 7.69 (d, 1H, J=6.0 Hz); 7.37-7.33 (m, 2H); 3.97 (s, 3H). MS m/z 194 (M⁺+H).

Step 3

To commercially available N-t-Boc-(2S,4R)-hydroxyproline (684 mg, 2.96 mmol) in DMSO (20 mL), potassium tert-butoxide (997 mgs, 8.88 mmol) was added in small portions, over 15 min at 23° C. The mixture was stirred at 23° C. for 30 min and then cooled to 0° C. At 0° C., 1-chloro-6-methoxy-isoquinoline (600 mgs, 3.11 mmol) was added in small portions over 10 min. The reaction mixture was stirred at 23° C. for 16 h. The resulting suspension was poured into 5% aqueous citric acid (100 mL) and extract with EtOAc (3×50 mL). The combined EtOAc layers were washed with brine and dried (MgSO₄). The organic layer was then filtered and concentrated to give (2S,4R)-(6-Methoxy-isoquinolin-1-yloxy)-pyrrolidine-1,2-dicarboxylic acid 1-tert-butyl ester (1.04 g, 2.68 mmol, 91% yield) as white solid. MS m/z 389 (M⁺+H). This material was used in the next step as crude without further purification.

Step 4

To [1S-(Cyclopropylcarbamoyl-hydroxy-methyl)-butyl]-carbamic acid tert-butyl ester (100 mg, 0.35 mmol) was added 4.0 M HCl in dioxane (10 mL). After 1 h, the reaction mixture was concentrated and dried to give the corresponding HCl salt as a white solid. To the above amine HCl salt in DCM/DMF (8:3. 11.0 mL) was added (2S,4R)-(6-Methoxy-isoquinolin-1-yloxy)-pyrrolidine-1,2-dicarboxylic acid 1-tert-butyl ester (136 mg, 0.35 mmol), HATU (160 mg, 0.42 mmol) and DIPEA (0.2 mL, 1.05 mmol). After 2 h at rt reaction mixture was diluted with ethyl acetate and washed with 1N HCl (2×), NaHCO₃ (1×), and brine (1×). The ethyl acetate layer was dried (MgSO₄), filtered and evaporated to dryness to give 2S-[1S-(Cyclopropylcarbamoyl-hydroxy-methyl)-butylcarbamoyl]-4R-(6-methoxy-isoquinolin-1-yloxy)-pyrrolidine-1-carboxylic acid tert-butyl ester.

Step 5

To the above crude compound was added 4.0 M HCl in dioxane (10 mL). After 1 h, the reaction mixture was concentrated and dried to give the corresponding HCl salt as a white solid. To the above amine HCl salt in DCM/DMF (8:3. 11.0 mL) was added 2S-(3-tert-Butyl-ureido)-3,3-dimethyl-butyric acid (81.0 mg, 0.35 mmol), HATU (160 mg, 0.42 mmol) and DIPEA (0.2 mL, 1.05 mmol). After 16 h at rt, the reaction mixture was diluted with ethyl acetate and washed with 1N HCl (2×), NaHCO₃ (1×), and brine (1×). The ethyl acetate layer was dried (MgSO₄), filtered and evaporated to dryness.

Step 6

The crude product was then dissolved in dry DCM (10.0 mL) and Dess-Martin periodinane (223 mg, 0.525 mmol) was added. After stirring at rt for 2 h, the reaction mixture was quenched with 0.26M Na₂S₂O₃ in saturated NaHCO₃ and extracted with ethyl acetate (3×). The combined ethyl acetate layers were then washed with saturated NaHCO₃ (2×) and brine (1×). Purification by preparative HPLC gave 1-[2S-(3-tert-Butyl-ureido)-3,3-dimethyl-butyryl]-4R-(6-methoxy-isoquinolin-1-yloxy)-pyrrolidine-2S-carboxylic acid (1S-cyclopropylaminooxalyl-butyl)-amide (21) in >95% purity by HPLC. ¹H NMR: (DMSO-d₆) 8.74 (d, 1H, J=4.8 Hz); 8.28 (d, 1H, J=7.2 Hz); 8.15 (d, 1H, J=9.2 Hz); 7.97 (d, 1H, J=6.0 Hz); 7.34-7.32 (m, 2H); 7.11-7.08 (m, 1H); 5.94 (brs, 1H); 5.72-5.70 (m, 1H); 5.04-5.00 (m, 1H); 4.58 (t, 1H, J=8.4 Hz); 4.34-4.22 (m, 2H); 3.91 (s, 3H); 3.90-3.86 (m, 1H); 2.79-2.74 (m, 1H); 2.54-2.51 (m, 1H); 2.18-2.11 (m, 1H); 1.77-1.70 (m, 1H); 1.48-1.38 (m, 3H); 1.15 (m, 9H); 0.91 (m, 9H); 0.90-0.86 (m, 3H); 0.69-0.56 (m, 4H). MS m/z 667 (M⁺+H), 689 (M⁺+Na), 665 (M⁺−H).

Example 10

Synthesis of 1-[2S-(3-tert-Butyl-ureido)-3,3-dimethyl-butyryl]-4R-(6-methoxy-isoquinolin-1-yloxy)-pyrrolidine-2S-carboxylic acid (2-cyclopropylcarbamoyl-1S-cyclopropylmethyl-2-oxo-ethyl)-amide (23)

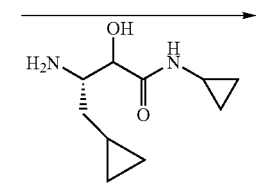

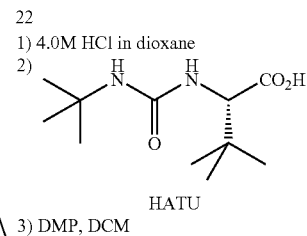

22

1) 4.0M HCl in dioxane
2) <br>HATU<br>3) DMP, DCM

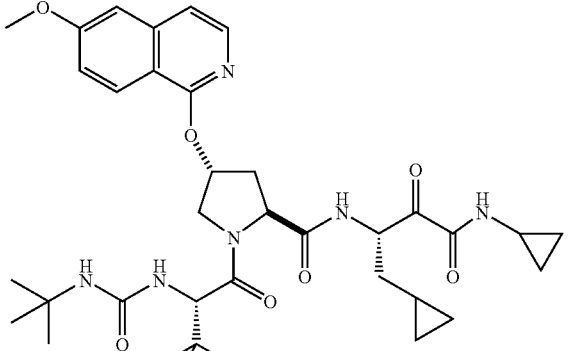

23

Step 1

To (S)-3-Amino-4,N-dicyclopropyl-2-hydroxy-butyramide HCl salt (47 mg, 0.2 mmol) in DCM/DMF (5:1.5, 6.5 mL) was added (2S,4R)-(6-Methoxy-isoquinolin-1-yloxy)-pyrrolidine-1,2-dicarboxylic acid 1-tert-butyl ester (78 mg, 0.2 mmol), HATU (91 mg, 0.4 mmol) and DIPEA (0.1 mL, 0.6 mmol). After 16 h at rt, the reaction mixture was diluted with ethyl acetate and washed with 1N HCl (2×), NaHCO$_3$ (1×), and brine (1×). The ethyl acetate layer was dried (MgSO$_4$), filtered and evaporated to dryness to give 2S-(2-Cyclopropylcarbamoyl-1S-cyclopropylmethyl-2(±)-hydroxy-ethylcarbamoyl)-4R-(6-methoxy-isoquinolin-1-yloxy)-pyrrolidine-1-carboxylic acid tert-butyl ester (22).

Step 2

To the above crude compound was added 4.0 M HCl in dioxane (5.0 mL). After 1 h, the reaction mixture was concentrated and dried to give the corresponding HCl salt as a white solid. To the above amine HCl salt in DCM/DMF (7:3. 10.0 mL) was added 2S-(3-tert-Butyl-ureido)-3,3-dimethyl-butyric acid (46 mg, 0.2 mmol), HATU (91 mg, 0.24 mmol) and DIPEA (0.1 mL, 0.6 mmol). After 3 h at rt, the reaction mixture was diluted with ethyl acetate and washed with 1N HCl (2×), NaHCO$_3$ (1×), and brine (1×). The ethyl acetate layer was dried (MgSO$_4$), filtered and evaporated to dryness.

Step 3

The crude product was then dissolved in dry DCM (8.0 mL) and Dess-Martin periodinane (127 mg, 0.3 mmol) was added. After stirring at rt for 2 h, the reaction mixture was quenched with 0.26 M Na$_2$S$_2$O$_3$ in saturated NaHCO$_3$ and extracted with ethyl acetate (3×). The combined ethyl acetate layers were then washed with saturated NaHCO$_3$ (2×) and brine (1×). Purification by preparative HPLC gave 1-[2S-(3-tert-Butyl-ureido)-3,3-dimethyl-butyryl]-4R-(6-methoxy-isoquinolin-1-yloxy)-pyrrolidine-2S-carboxylic acid (2-cyclopropylcarbamoyl-1S-cyclopropylmethyl-2-oxo-ethyl)-amide (23) in >95% purity by HPLC. MS m/z 679 (M$^+$+H), 701 (M$^+$+Na), 677 (M$^+$−H).

Example 11

Synthesis of 1-[2S-(3-tert-Butyl-ureido)-3,3-dimethyl-butyryl]-4R-(6-ethoxy-isoquinolin-1-yloxy)-pyrrolidine-2-carboxylic acid (2-cyclopropylcarbamoyl-1S-cyclopropylmethyl-2S-oxo-ethyl)-amide (26)

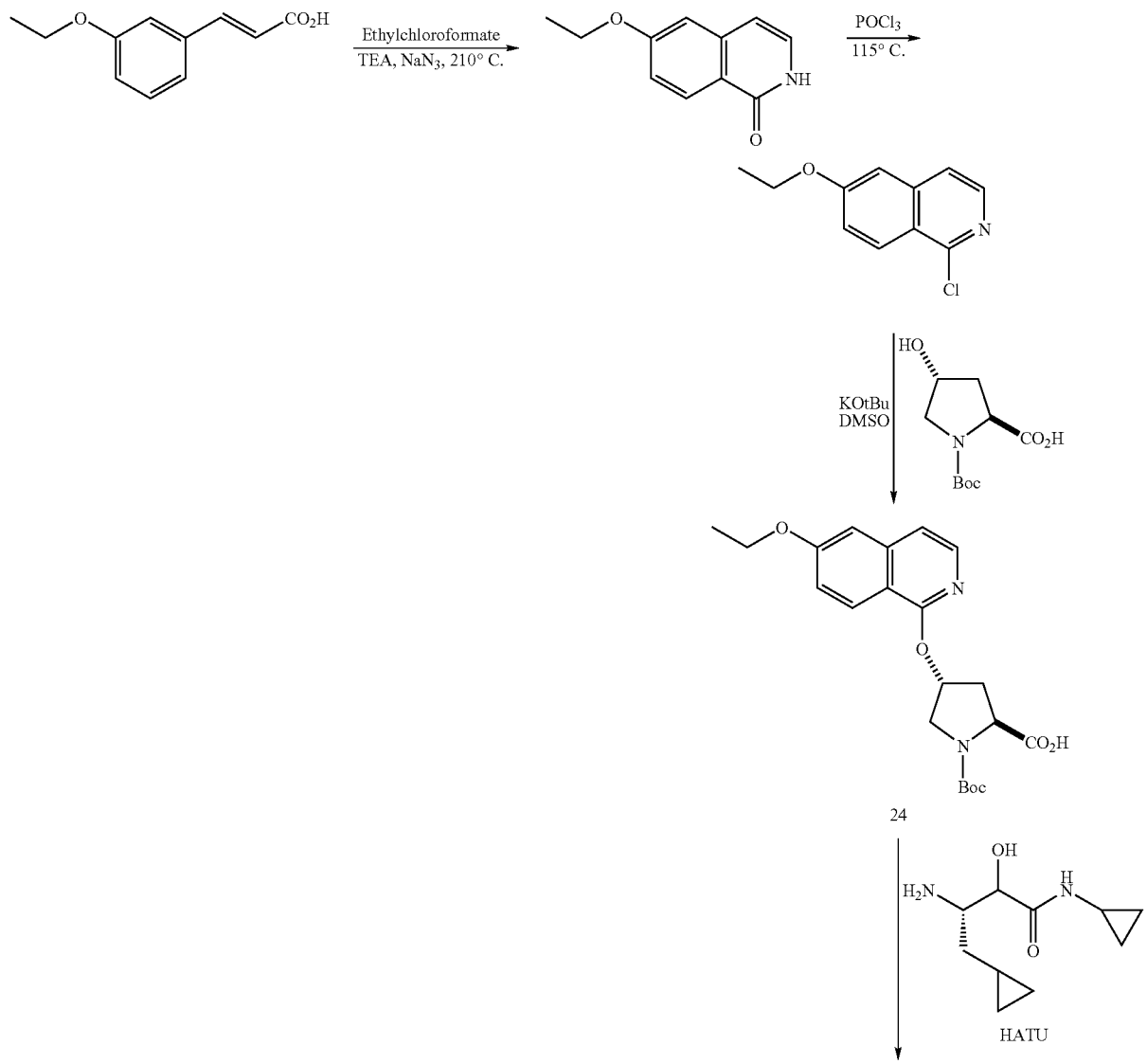

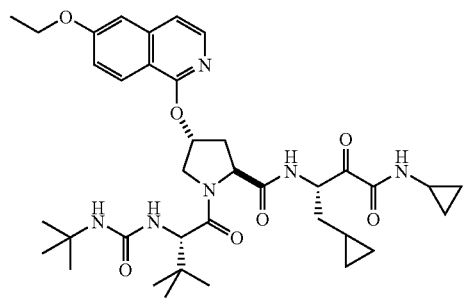 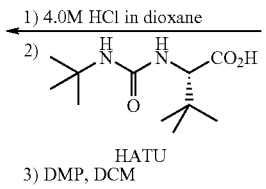 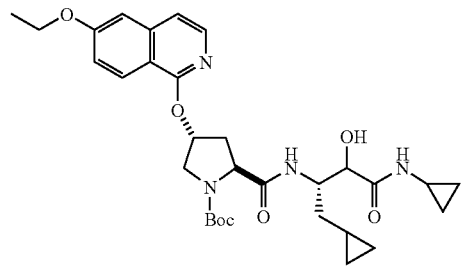

26

25

Step 1

Ethyl chloroformate (4.3 mL, 44.5 mmol) was added drop wise at 0° C. to a solution of 3-Ethoxy cinnamic acid (5.71 g, 29.7 mmol) and triethylamine (8.3 mL, 59.4 mmol) in acetone (35 mL). After 1 h at 0° C., aqueous sodium azide (3.1 g, 47.5 mmol, 16 mL water) was added dropwise and the reaction mixture was stirred at 23° C. for 16 h. Water (50 mL) was added to the mixture and the volatile was removed under vacuo. The resulting slurry was extracted with toluene (3×25 mL) and the combined organic layers were dried (MgSO$_4$). The dried solution was filtered and added dropwise at 190° C. to a solution of diphenylmethane (25 mL) and tributylamine (14.2 mL, 59.4 mmol). The toluene was distilled off as added. After complete addition, the reaction temperature was raised to 210° C. for 2 h. After cooling, the precipitated product was collected by filtration and washed with hexanes and dried under vacuum to yield 6-Ethoxy-2H-isoquinolin-1-one (1.92 g, 10.2 mmol, 34% yield). MS m/z 190 (M$^+$+H).

Step 2

A suspension of 6-Ethoxy-2H-isoquinolin-1-one (896 mg, 4.74 mmol) in POCl$_3$ (4 mL) was heated at 110° C. for 3 h (clear solution obtained upon heating). After 3 h, the reaction mixture was concentrated under reduced pressure. The residue was poured into iced water (10 mL), pH was then adjusted to 10 with 3N NaOH and extracted with CHCl$_3$ (3×25 mL). The combined CHCl$_3$ layers were washed with brine and dried (MgSO$_4$). The organic layer was then filtered and concentrated to give 1-chloro-6-ethoxy-isoquinoline (866 mg, 4.18 mmol, 88% yield, >90% pure) as tan solid. MS m/z 208 (M$^+$+H).

Step 3

To commercially available N-t-Boc-(2S,4R)-hydroxyproline (531 mg, 2.30 mmol) in DMSO (20 mL), potassium tert-butoxide (774 mg, 6.9 mmol) was added in small portions, over 15 min at 23° C. The mixture was stirred at 23° C. for 30 min and then cooled to 0° C. At 0° C., 1-chloro-6-ethoxy-isoquinoline (500 mgs, 2.41 mmol) was added in small portions over 10 min. The reaction mixture was stirred at 23° C. for 16 h. The resulting suspension was poured into water and the mixture was washed with ether (2×) and ethylacetate (2×). The aqueous layer was acidified with aqueous 1N HCl to pH ~4 and extracted with DCM (3×). The combined DCM layers were washed with brine and dried (MgSO$_4$). The organic layer was then filtered, and concentrated to give (2S,4R)-(6-ethoxy-isoquinolin-1-yloxy)-pyrrolidine-1,2-dicarboxylic acid 1-tert-butyl ester (24) (crude wt=1.18 g, >90% pure). MS m/z 403 (M$^+$+H), 401 (M$^+$–H), 303 (M$^+$–Boc). This material was used in the next step as crude without further purification.

Step 4

To (S)-3-Amino-4,N-dicyclopropyl-2-hydroxy-butyramide HCl salt (66 mgs, 0.28 mmol) in DCM/DMF (10:3, 13 mL) was added (2S,4R)-(6-ethoxy-isoquinolin-1-yloxy)-pyrrolidine-1,2-dicarboxylic acid 1-tert-butyl ester (114 mgs, 0.28 mmol), HATU (128 mg, 0.34 mmol) and DIPEA (0.15 mL, 0.84 mmol). After 1 h at rt, the reaction mixture was diluted with ethyl acetate and washed with 1N HCl (2×), NaHCO$_3$ (1×), and brine (1×). The ethyl acetate layer was dried (MgSO$_4$), filtered and evaporated to dryness to give 2S-(2-Cyclopropylcarbamoyl-1S-cyclopropylmethyl-2-hydroxy-ethylcarbamoyl)-4R-(6-ethoxy-isoquinolin-1-yloxy)-pyrrolidine-1-carboxylic acid tert-butyl ester (25).

Step 5

To the above crude compound was added 4.0 M HCl in dioxane (10 mL). After 1 h, the reaction mixture was concentrated and dried to give the corresponding HCl salt as a white solid. To the above amine HCl salt in DCM/DMF (10:3, 13 mL) was added 2S-(3-tert-Butyl-ureido)-3,3-dimethyl-butyric acid (64 mgs, 0.28 mmol), HATU (128 mg, 0.34 mmol) and DIPEA (0.15 mL, 0.84 mmol). After 1 h at rt, the reaction mixture was diluted with ethyl acetate and washed with 1N HCl (2×), NaHCO$_3$ (1×), and brine (1×). The ethyl acetate layer was dried (MgSO$_4$), filtered and evaporated to dryness.

Step 6

The crude product was then dissolved in dry DCM (10.0 mL) and Dess-Martin periodinane (154 mgs, 0.364 mmol) was added. After stirring at rt for 1 h, the reaction mixture was quenched with 0.26M Na$_2$S$_2$O$_3$ in saturated NaHCO$_3$ and extracted with EtOAc (3×). The combined EtOAc layers were then washed with saturated NaHCO$_3$ (2×), brine (1×) and dried (MgSO$_4$). The organic layer was then filtered, concentrated and purified by flash chromatography (65% ethyl acetate/hexane) to give 1-[2S-(3-tert-Butyl-ureido)-3,3-dimethyl-butyryl]-4R-(6-ethoxy-isoquinolin-1-yloxy)-pyrrolidine-2-carboxylic acid (2-cyclopropylcarbamoyl-1S-cyclopropylmethyl-2S-oxo-ethyl)-amide (26) (80.7 mg, 0.116 mmol, 42% yield) as white solid. $^1$H NMR: (DMSO) 8.67 (d, 1H, J=5.6 Hz); 8.26 (d, 1H, J=6.8 Hz); 8.06 (d, 1H, J=8.8 Hz); 7.89 (d, 1H, J=5.6 Hz); 7.24-7.22 (m, 1H); 7.01-6.98 (dd, 1H, J=2.4, 8.8 Hz); 5.90-5.85 (m, 2H); 5.65-5.62 (m, 1H); 5.06-5.01 (m, 1H); 4.53 (t, 1H, J=8.0 Hz); 4.26-4.23 (m, 1H); 4.16-4.08 (m, 3H); 3.84-3.80 (m, 1H); 2.69-2.65 (m, 1H); 2.11-2.04 (m, 1H); 1.64-1.57 (m, 1H); 1.35-1.29 (m, 3H); 1.15 (m, 9H); 0.91 (m, 9H); 0.89-0.81 (m, 3H); 0.61-0.48 (m, 4H); 0.36-0.27 (m, 2H). MS m/z 693 (M$^+$+H), 715 (M$^+$+Na), 691 (M$^+$–H).

Example 12

Synthesis of 1-[2S-(3-tert-Butyl-ureido)-3,3-dimethyl-butyryl]-4R-(6-ethoxy-isoquinolin-1-yloxy)-pyrrolidine-2S-carboxylic acid (1S-cyclopropylaminooxalyl-butyl)-amide (28)

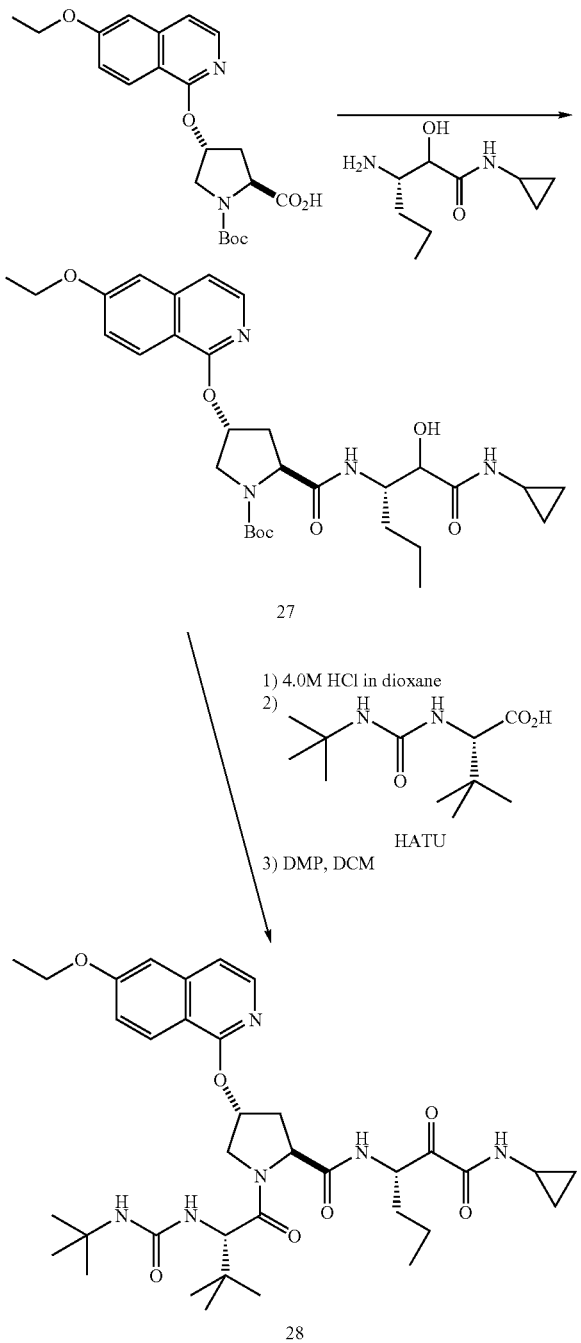

Step 1

To [1S-(Cyclopropylcarbamoyl-hydroxy-methyl)-butyl]-carbamic acid tert-butyl ester (75 mg, 0.26 mmol) was added 4.0 M HCl in dioxane (6.0 mL). After 1 h, the reaction mixture was concentrated and dried to give the corresponding HCl salt as a white solid. To the above amine HCl salt in DCM/DMF (10:3, 13 mL) was added (2S,4R)-(6-ethoxy-isoquinolin-1-yloxy)-pyrrolidine-1,2-dicarboxylic acid 1-tert-butyl ester (106 mgs, 0.26 mmol), HATU (119 mg, 0.31 mmol) and DIPEA (0.15 mL, 0.78 mmol). After 1 h at rt reaction mixture was diluted with ethyl acetate and washed with 1N HCl (2×), NaHCO$_3$ (1×), and brine (1×). The ethyl acetate layer was dried (MgSO$_4$), filtered and evaporated to dryness to give 2S-[1S-(Cyclopropylcarbamoyl-hydroxy-methyl)-butylcarbamoyl]-4R-(6-ethoxy-isoquinolin-1-yloxy)-pyrrolidine-1-carboxylic acid tert-butyl ester (27).

Step 2

To the above crude compound was added 4.0 M HCl in dioxane (10 mL). After 1 h, the reaction mixture was concentrated and dried to give the corresponding HCl salt as a white solid. To the above amine HCl salt in DCM/DMF (10:3, 13 mL) was added 2S-(3-tert-Butyl-ureido)-3,3-dimethyl-butyric acid (60 mgs, 0.26 mmol), HATU (128 mg, 0.34 mmol) and DIPEA (0.15 mL, 0.84 mmol). After 1 h at rt, the reaction mixture was diluted with ethyl acetate and washed with 1N HCl (2×), NaHCO$_3$ (1×), and brine (1×). The ethyl acetate layer was dried (MgSO$_4$), filtered and evaporated to dryness.

Step 3

The crude product was then dissolved in dry DCM (10.0 mL) and Dess-Martin periodinane (143 mgs, 0.338 mmol) was added. After stirring at rt for 1 h reaction mixture was quenched with 0.26 M Na$_2$S$_2$O$_3$ in saturated NaHCO$_3$ and extracted with ethyl acetate (3×). The combined ethylacetate layers were then washed with saturated NaHCO$_3$ (2×), brine (1×) and dried (MgSO$_4$). The organic layer was then filtered, concentrated and purified by flash chromatography (65% ethyl acetate/hexane) to give 1-[2S-(3-tert-Butyl-ureido)-3,3-dimethyl-butyryl]-4R-(6-ethoxy-isoquinolin-1-yloxy)-pyrrolidine-2S-carboxylic acid (1S-cyclopropylaminooxalyl-butyl)-amide (28) (75.7 mg, 0.11 mmol, 43% yield) as white solid. $^1$H NMR: (DMSO-d$_6$) 8.75 (d, 1H, J=4.8 Hz); 8.28 (d, 1H, J=7.2 Hz); 8.13 (d, 1H, J=8.8 Hz); 7.96 (d, 1H, J=6.0 Hz); 7.31-7.29 (m, 2H); 7.10-7.06 (dd, 1H, J=2.4, 9.2 Hz); 5.94-5.92 (m, 2H); 5.72-5.70 (m, 1H); 5.04-5.00 (m, 1H); 4.58 (t, 1H, J=7.6 Hz); 4.34-4.30 (m, 1H); 4.23-4.17 (m, 3H); 3.90-3.86 (m, 1H); 2.79-2.74 (m, 1H); 2.54-2.51 (m, 1H); 2.18-2.11 (m, 1H); 1.77-1.70 (m, 1H); 1.48-1.38 (m, 3H); 1.15 (m, 9H); 0.91 (m, 9H); 0.89-0.86 (m, 3H); 0.69-0.59 (m, 4H). MS m/z 681 (M$^+$+H), 703 (M$^+$+Na), 679 (M$^+$−H).

Example 13

Synthesis of 1-[2S-(3-tert-Butyl-ureido)-3,3-dimethyl-butyryl]-4R-(6-methoxy-isoquinolin-1-yloxy)-pyrrolidine-2S-carboxylic acid (1S-cyclopropylaminooxalyl-pentyl)-amide (30)

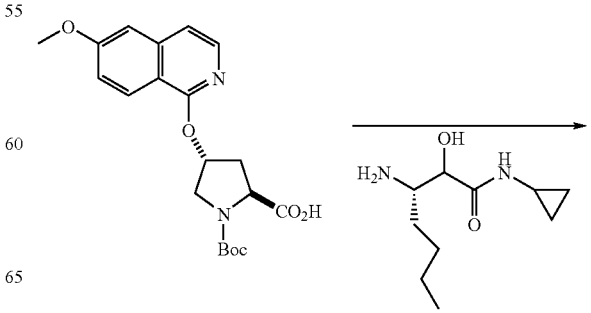

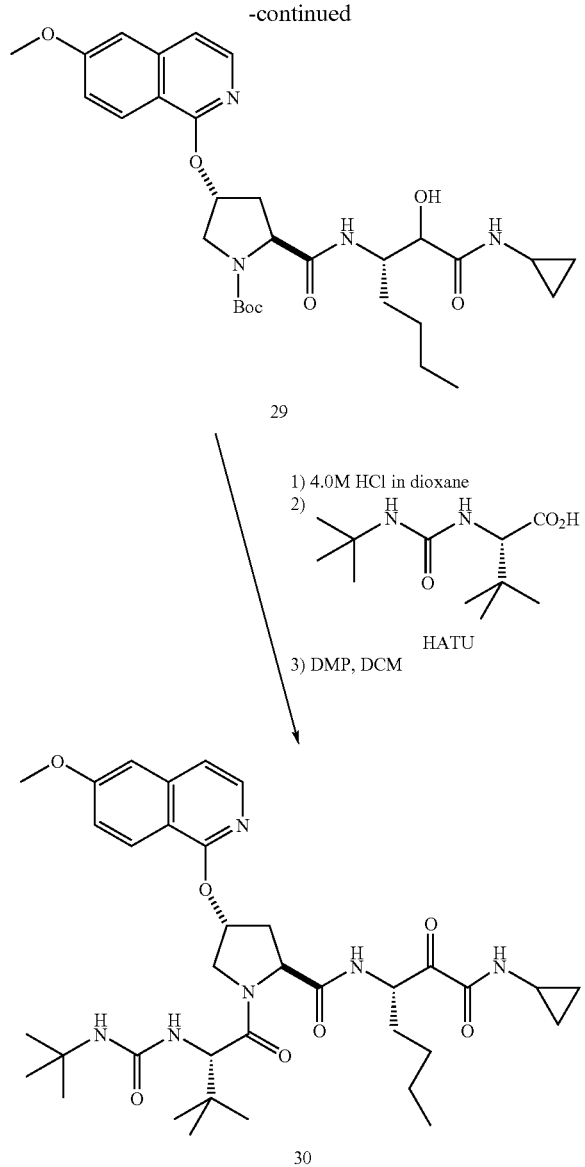

pyrrolidine-1,2-dicarboxylic acid 1-tert-butyl ester (157 mgs, 0.40 mmol), HATU (200 mg, 0.53 mmol) and DIPEA (0.35 mL, 2.0 mmol). After 1 h at rt reaction mixture was diluted with ethyl acetate and washed with 1N HCl (2×), NaHCO$_3$ (1×), and brine (1×). The ethyl acetate layer was dried (MgSO$_4$), filtered and evaporated to dryness to give 2S-[1S-(Cyclopropylcarbamoyl-(±)-hydroxy-methyl)-pentylcarbamoyl]-4R-(6-methoxy-isoquinolin-1-yloxy)-pyrrolidine-1-carboxylic acid tert-butyl ester (29). MS m/z 571 (M$^+$+H), 593 (M$^+$+Na), 569 (M$^+$–H), 471 (M$^+$–Boc).

Step 2

To the above crude compound was added 4.0 M HCl in dioxane (10 mL). After 1 h at rt, the reaction mixture was concentrated and dried to give the corresponding HCl salt as a white solid. To the above amine HCl salt in DCM/DMF (10:3, 13 mL) was added 2S-(3-tert-Butyl-ureido)-3,3-dimethyl-butyric acid (93 mgs, 0.40 mmol), HATU (200 mg, 0.53 mmol) and DIPEA (0.35 mL, 2.0 mmol). After 1 h at rt reaction mixture was diluted with ethyl acetate and washed with 1N HCl (2×), NaHCO$_3$ (1×), and brine (1×). The ethyl acetate layer was dried (MgSO$_4$), filtered and evaporated to dryness. MS m/z 683 (M$^+$+H), 705 (M$^+$+Na), 681 (M$^+$–H).

Step 3

The crude product was then dissolved in dry DCM (10.0 mL) and Dess-Martin periodinane (223 mgs, 0.53 mmol) was added. After stirring at rt for 2 h reaction mixture was quenched with 0.26M Na$_2$S$_2$O$_3$ in saturated NaHCO$_3$ and extracted with ethyl acetate (3×). The combined ethylacetate layers were then washed with saturated NaHCO$_3$ (2×), brine (1×) and dried (MgSO$_4$). The organic layer was then filtered, concentrated and purified by flash chromatography (45% ethyl acetate/hexane) to give 1-[2S-(3-tert-Butyl-ureido)-3,3-dimethyl-butyryl]-4R-(6-methoxy-isoquinolin-1-yloxy)-pyrrolidine-2S-carboxylic acid (1S-cyclopropylaminooxalyl-pentyl)-amide (30) (83.5 mg, 0.12 mmol, 31% yield) as white solid. $^1$H NMR: (DMSO) 8.74 (d, 1H, J=4.8 Hz); 8.27 (d, 1H, J=7.2 Hz); 8.15 (d, 1H, J=9.2 Hz); 7.97 (d, 1H, J=6.0 Hz); 7.33-7.31 (m, 2H); 7.10-7.08 (dd, 1H, J=2, 8.8 Hz); 5.96 (s, 1H); 5.94 (d, 1H, J=9.6 Hz); 5.71-5.69 (m, 1H); 5.02-4.98 (m, 1H); 4.60 (t, 1H, J=8.4 Hz); 4.34-4.22 (m, 1H); 4.23 (d, 1H, J=9.2 Hz); 3.91 (s, 3H); 3.90-3.87 (m, 1H); 2.78-2.73 (m, 1H); 2.54-2.51 (m, 1H); 2.17-2.11 (m, 1H); 1.77-1.72 (m, 1H); 1.43-1.33 (m, 5H); 1.20 (m, 9H); 0.95 (m, 9H); 0.88-0.85 (m, 5H); 0.69-0.58 (m, 4H). MS m/z 681 (M$^+$+H), 703 (M$^+$+Na), 680 (M$^+$–H).

Step 1

To (S)-3-Amino-2-hydroxy-heptanoic acid cyclopropylamide HCl salt (96 mgs, 0.40 mmol) in DCM/DMF (10:3, 13 mL) was added (2S,4R)-(6-Methoxy-isoquinolin-1-yloxy)-

Example 14

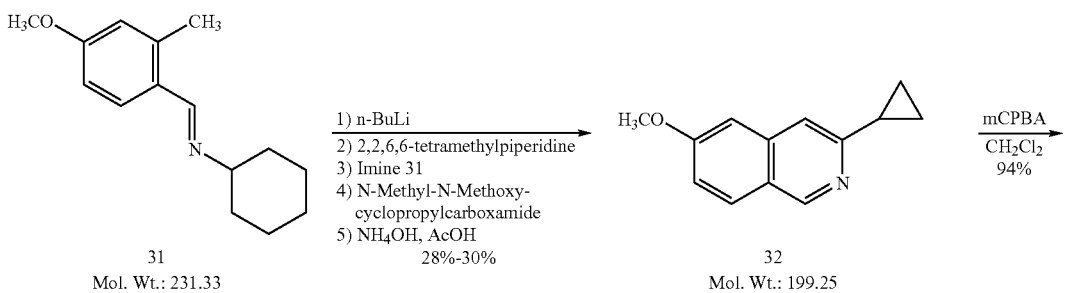

-continued
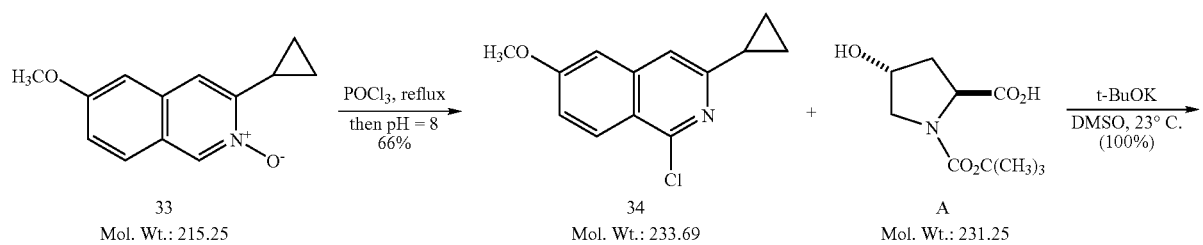
33
Mol. Wt.: 215.25
34
Mol. Wt.: 233.69
A
Mol. Wt.: 231.25
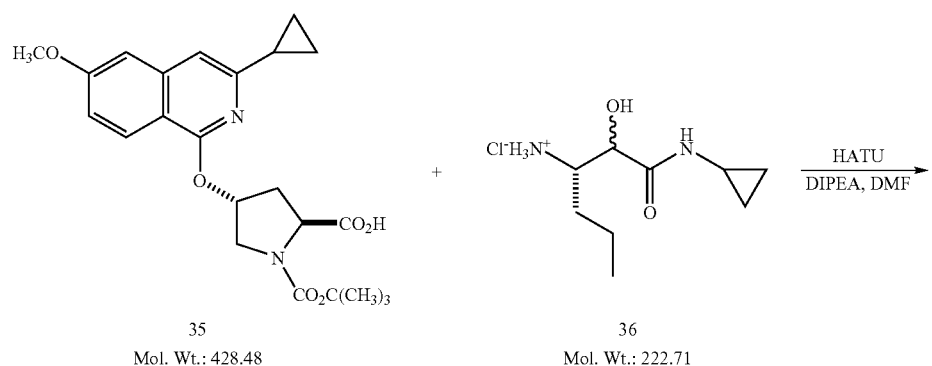
35
Mol. Wt.: 428.48
36
Mol. Wt.: 222.71
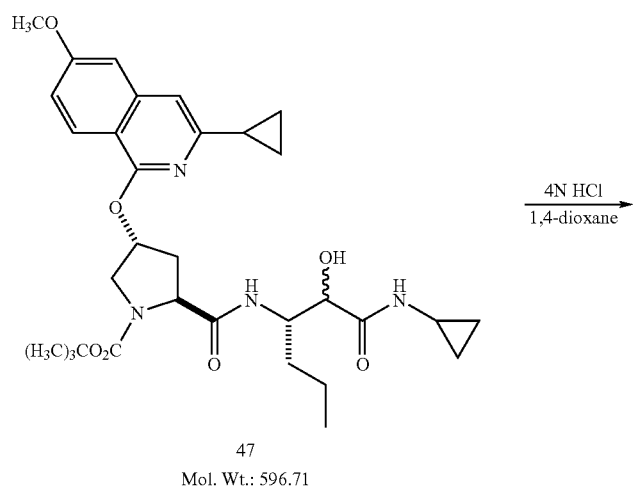
47
Mol. Wt.: 596.71
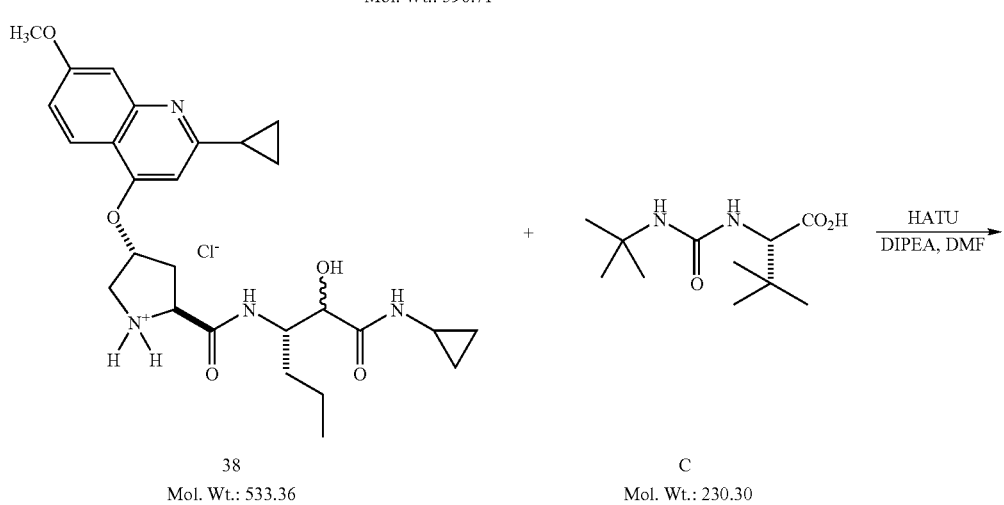
38
Mol. Wt.: 533.36
C
Mol. Wt.: 230.30

-continued

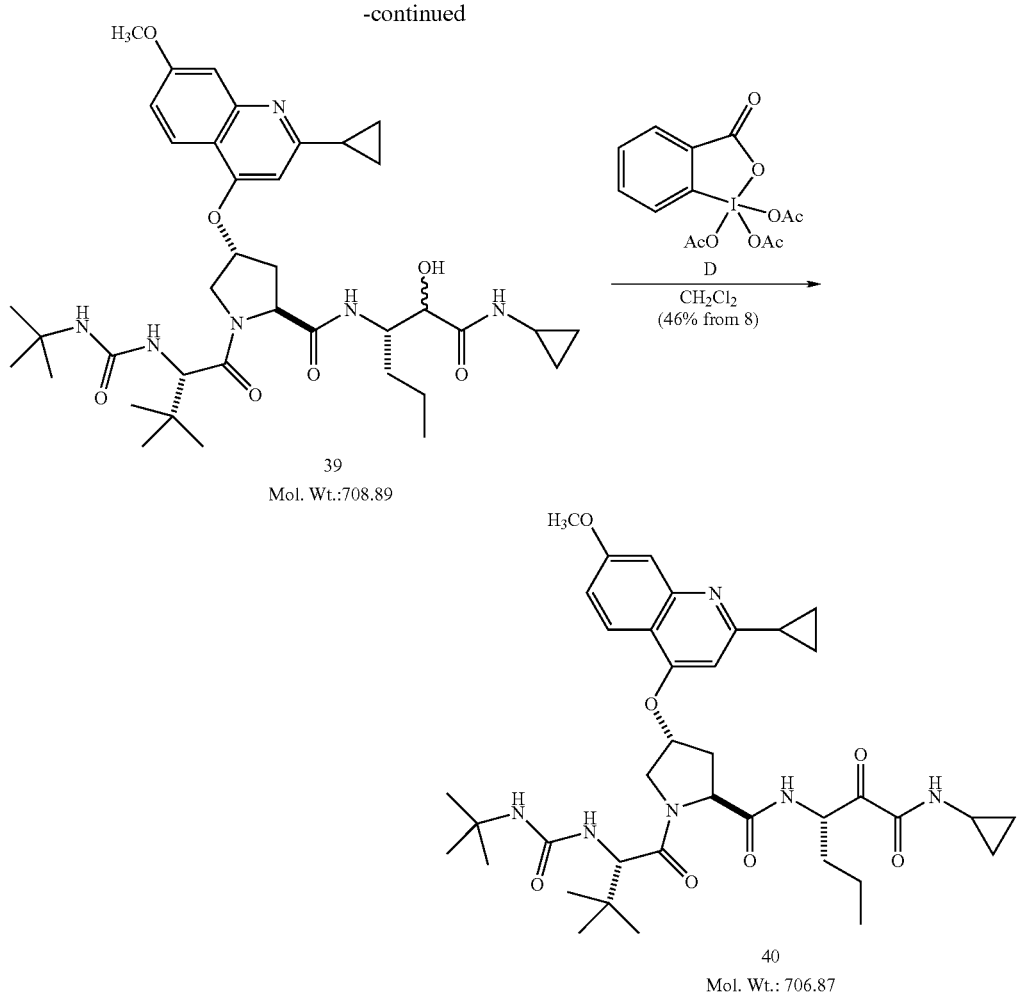

39
Mol. Wt.:708.89

40
Mol. Wt.: 706.87

Step 1

3-Cyclopropyl-6-methoxyisoquinoline (32). Lithium tetramethylpiperidide was prepared by the treatment of 2,2,6,6-tetramethylpiperidine (1.0 g; 7.0 mmol) in THF (17 mL) with n-BuLi (1.6 M in hexanes; 8.0 mmol) dropwise at −15° C. After 15 min at −15° C., a solution of cyclohexyl(4-methoxy-2-methylbenzylidene)amine (660 mg; 2.86 mmol) in THF (3 mL) was added dropwise to give a purple solution. The reaction mixture was allowed to warm to 0° C. over a 20-min period then a solution of N-methyl-N-methoxycyclopropanecarboxamide (630 mg; 4.4 mmol) in THF (2 mL) was added in one portion while at 0° C. The reaction mixture was kept at room temperature for 30 min and then added to saturated aq. $NH_4Cl$. The solution was extracted with diethyl ether and the organic phase was washed with saturated aq. NaCl, dried and concentrated in vacuo.

The residue was dissolved in concentrated $NH_4OH$ (15 mL) and treated with acetic acid (1 mL) then heated to reflux. The mixture was diluted with water, and the resulting solution extracted with diethyl ether. The ether extracts were washed with water, and saturated aq. NaCl, then dried and concentrated in vacuo. Chromatography ($SiO_2$; 4:1 hexane/EtOAc) provided 160 mg (28%) of the title compound. Execution of the process with 1.5 g of the imine provided 400 mg (30%) of the title compound.

Step 2

1-Chloro-3-cyclopropyl-6-methoxy-isoquinoline (34). 3-Cyclopropyl-6-methoxyisoquinoline (32) was dissolved in dichloromethane (8 mL) and cooled to 0° C. This solution was treated with a solution of m-chloroperbenzoic acid (mCPBA; 412 mg; 2.4 mmol) in dichloromethane (8 mL) and the mixture was stirred for 2 h at RT. The reaction mixture was quenched with dimethyl sulfide (100 µL) and stirred for another 15 min. The mixture was treated with saturated aq. sodium bicarbonate (20 mL) and the layers were separated. The aq. phase was extracted with dichloromethane and the combined organic phases were dried, concentrated in vacuo and chromatographed ($SiO_2$; 10% MeOH in $CH_2Cl_2$) to give 405 mg (94%) of the N-oxide of 3-cyclopropyl-6-methoxy-isoquinoline (33).

The N-oxide was dissolved in dichloromethane (5 mL) and 1 mL of $POCl_3$ was added. The mixture was heated at reflux for 2 h, cooled and poured onto ice. The mixture was treated with $NH_4OH$ to pH 8 and the resulting solution was extracted with ethyl acetate. The organic phase was washed with sat. aq. NaCl, dried and concentrated in vacuo. The crude product was purified by chromatography ($SiO_2$; Hexane/EtOAc, 4:1) to provide 310 mg (66% overall) of the title compound.

Step 3

1-N-BOC-4-(3-Cyclopropyl-6-methoxyisoquinolin-1-yloxy)pyrrolidine-2-carboxylic acid (37). N-BOC-4-hydroxy-L-proline (A; 192 mg; 830 µmol) was dissolved in DMSO (5 mL) at RT then potassium t-butoxide (270 mg; 2.4 mmol) was added. The resulting solution was stirred at RT for 1.5 h then 1-Chloro-3-cyclopropyl-6-methoxyisoquinoline (4; 192 mg; 820 μmol) was added. The resulting solution was stirred overnight, diluted with 15 mL of 5% aq. citric acid and extracted with ethyl acetate. The organic phase was washed with sat. aq. NaCl, dried and concentrated in vacuo to give 375 mg of the crude arylether of N-BOC-4-hydroxy-L-proline (35).

The crude aryl ether was dissolved in DMF (2 mL) and (O-7-azabenzotriazol-1-yl)-1,1,3,3-tetramethyluronium hexafluorophosphate (HATU; 380 mg; 830 μmol) was added followed by 3-(S)-amino-2-(RS)-hydroxyhexanoic acid-N-cyclopropylcarboxamide hydrochloride (36; 190 mg; 830 mop and N,N-diisopropylethylamine (DIPEA; 800 pt). The resulting mixture was stirred overnight then diluted with water. The resulting precipitate was filtered, washed with water and dried to give 460 mg (93%) of the title compound (37).

Step 4

(S)-1-[2-(3-tert-Butylureido)-3,3-dimethylbutyryl]-4-trans-(2-cyclopropyl-7-methoxyquinolin-4-yloxy)pyrrolidine-2-(S)-carboxylic acid (1-cyclopropylaminooxalyl-butyl)amide Hydrochloride (40). Compound 37 was dissolved in 4N HCl in 1,4-dioxane (2 mL) and stirred 1 h at RT. The reaction mixture was concentrated in vacuo and the residue (compound 38) was dissolved in DMF (2 mL). The solution was treated with (S)-2-(3-tert-butylureido)-3,3-dimethylbutyric acid (C; 100 mg; 440 μmol), HATU (200 mg; 520 gmol), and DIPEA (800 mL). The reaction mixture was diluted with water and the resulting precipitate was filtered, washed with water and dried to give 250 mg (80%) of the corresponding 2-hydroxycarboxamide 39. The solid was dissolved in dichloromethane (20 mL) and treated with 1,1,1-tris(acetyloxy)-1,1-dihydro-1,2-benziodoxol-3-(1H)-one (D; 220 mg; 660 μmol). The reaction mixture was stirred for 2 h at RT. The solution was diluted with diethyl ether (40 mL) followed by the addition of saturated aq. $Na_2S_2O_3$ (10 mL) and 10 mL of aq. $NaHCO_3$ (10 mL). The biphasic mixture was stirred for 10 min and the layers were separated. The organic phase was washed with saturated aq. NaCl, dried and concentrated in vacuo. The residue was purified by chromatography ($SiO_2$; Hexane/EtOAc, 1:1) then the isolated material was lyophilized from acetonitrile and 0.01% aq. HCl to give 150 mg (46%) of the title compound (40) as the HCl salt. Mass Spec (M+Na) 705.

Example 15

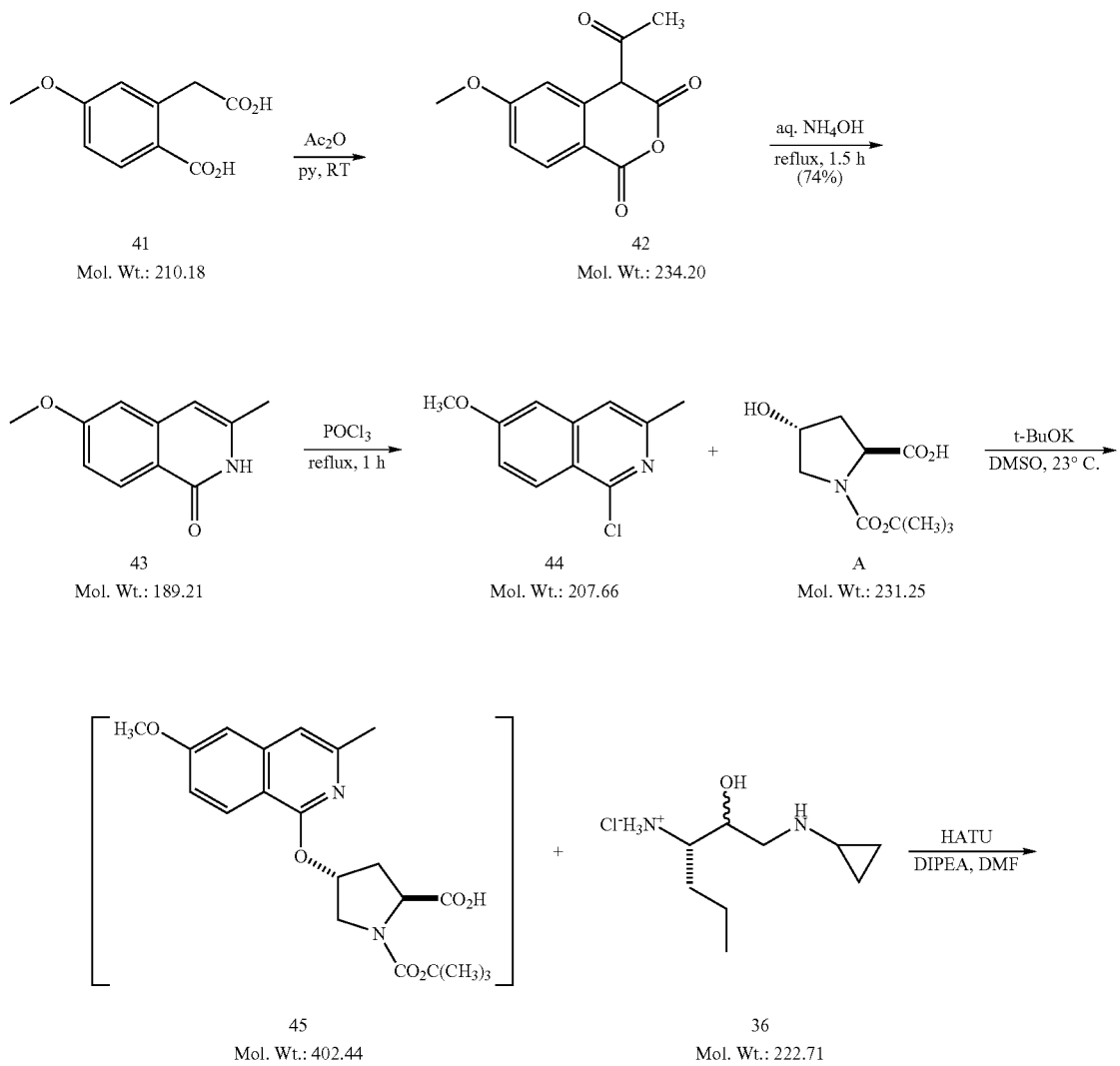

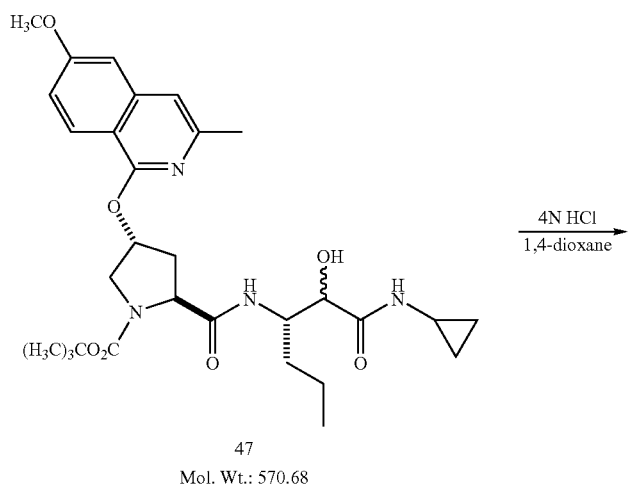
47
Mol. Wt.: 570.68
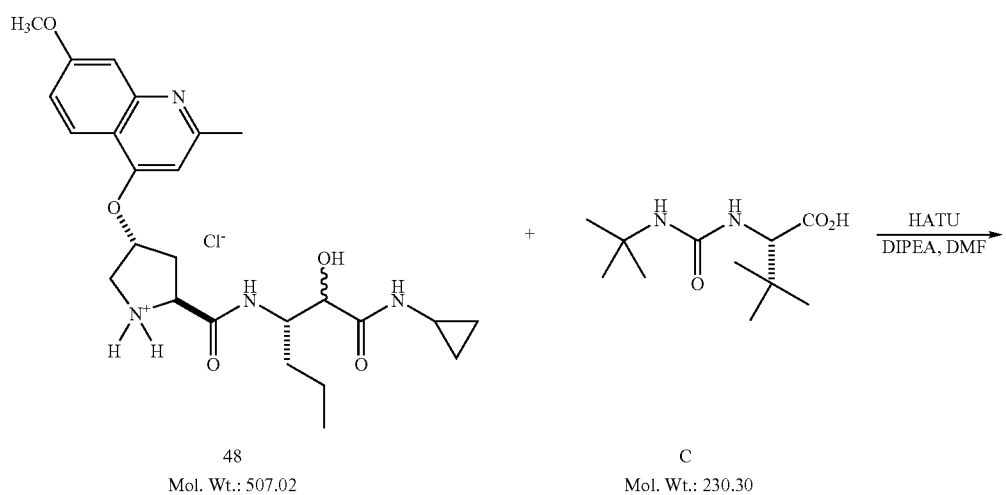
48
Mol. Wt.: 507.02
C
Mol. Wt.: 230.30
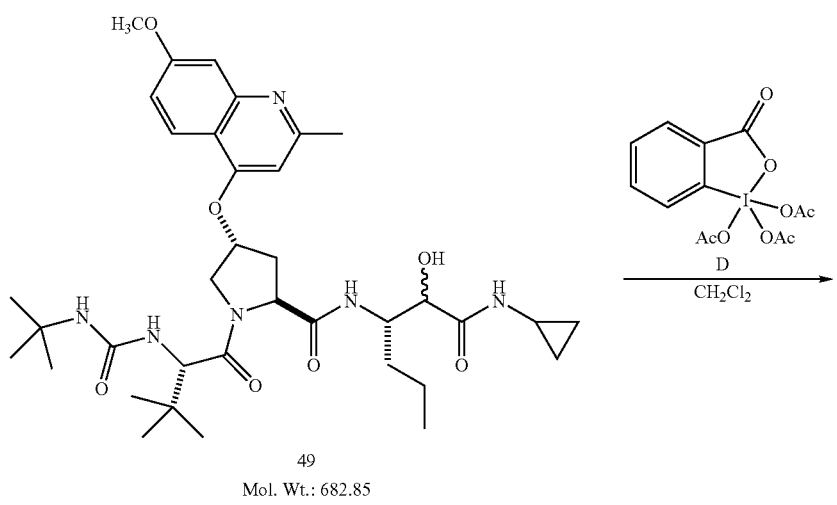
49
Mol. Wt.: 682.85

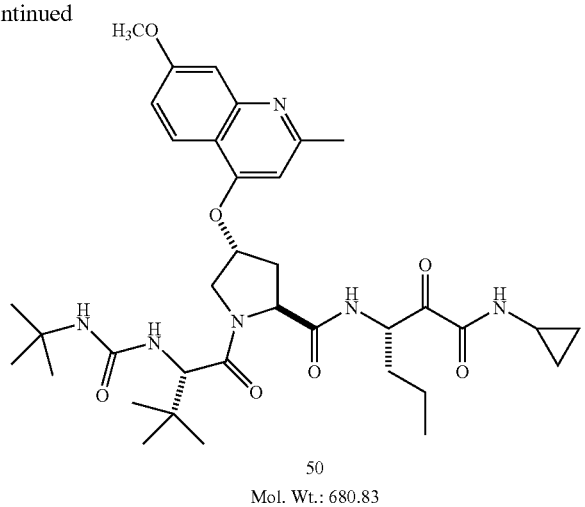

50
Mol. Wt.: 680.83

Step 1
4-Acetyl-6-methoxyisochroman-1,3-dione (42). Following a literature procedure (*Ind. J. Chem. Sec. B,* 1986, 25B, 640-643), 2-carboxymethyl-4-methoxybenzoic acid (41; 1.0 g; 4.8 mmol) was dissolved in a mixture of pyridine (1.4 mL) and acetic anhydride (8.6 mL; 9.3 g; 91 mmol) then stirred for 3 h during which time a solid had formed. The suspension was diluted with diethyl ether, filtered and the filter cake washed with diethyl ether. Yield: 905 mg (81%) of the title compound.

Step 2
6-Methoxy-3-methyl-2H-isoquinolin-1-one (43). Cyclic anhydride 42 (405 mg; 1.73 mmol) was dissolved in aqueous NH₄OH and heated at reflux for 1.5 h. The mixture was cooled to RT and the solid was filtered then dried overnight to give 270 mg (74%) of the title compound.

Step 3
1-Chloro-6-methoxy-3-methylisoquinoline (44). Isoquinoline-1-one 43 was dissolved in POCl₃ (2.5 mL) and heated at reflux for 1 h. The excess POCl₃ was removed in vacuo and the residue was dissolved in CHCl₃. The resulting solution was washed with 1N aq. NaOH, water and saturated aq. NaCl. Evaporation of the solvent gave crude 44 which was used directly in the next step.

Step 4
1-N-BOC-4-(6-Methoxy-3-methylisoquinolin-1-yloxy)pyrrolidine-2-carboxylic acid (45). N-BOC-4-hydroxy-L-proline (A; 281 mg; 1.21 mmol) was dissolved in DMSO (3 mL) at RT then potassium t-butoxide (270 mg; 2.4 mmol) was added. The resulting solution was stirred at RT for 2 h then cooled to 0° C. Next a solution of isoquinoline 14 in DMSO (3 mL) was added dropwise to the cold solution of A and t-BuOK, then the mixture was allowed to warm up to RT. The solution was stirred for 16 h, and an addition 0.2 equivalents of A was added and the mixture stirred for an additional 1.5 h. The reaction mixture was acidified to pH=4 with 5% aq. citric acid. The solution was extracted with ethyl acetate and the organic phase washed with water followed by saturated aq. NaCl. The organic phase was concentrated in vacuo to give the title compound.

Step 5
1-N-BOC-2-[1-(Cyclopropylcarbamoylhydroxymethyl)butylcarbamoyl]-4-(6-methoxy-3-methyl-isoquinolin-1-yloxy)pyrrolidine (47). Compound 45 (196 mg; 487 μmol) was converted to the title compound according to the same process described for compound 5. Pyrrolidine 47 (210 mg; 77% yield) was used in the subsequent step without further purification.

Step 6
1-[2-(3-tert-Butyl-ureido)-3,3-dimethyl-butyryl]-4-(7-methoxy-2-methylquinolin-4-yloxy)-pyrrolidine-2-carboxylic acid (1-cyclopropylaminooxalylbutyl)-amide (50). Compound 47 (210 mg; 368 μmol) was converted to the corresponding HCl salt as described for compound 48. The HCl salt 48 was then converted to the tripeptide 49 with intermediate C and HATU using the same conditions employed for compound 39. Finally 49 was converted to the title compound, α-ketoamide 50 employing D in dichloromethane according to the same procedure give above for the conversion of 39 to 40. Purification of the crude product by chromatography (SiO₂; 45% ethyl acetate in hexane) provided 85 mg of 50 (34% from 17). Mass Spec (M+) 680.

Example 16

Synthesis of 1-[2S-(3-tert-Butyl-ureido)-3,3-dimethyl-butyryl]-4R-(7-methoxy-2-pyrazol-1-yl-quinolin-4-yloxy)pyrrolidine-2S-carboxylicacid(1S-cyclopropylaminooxalyl-butyl)-amide (1)

Alternative route for compound 7

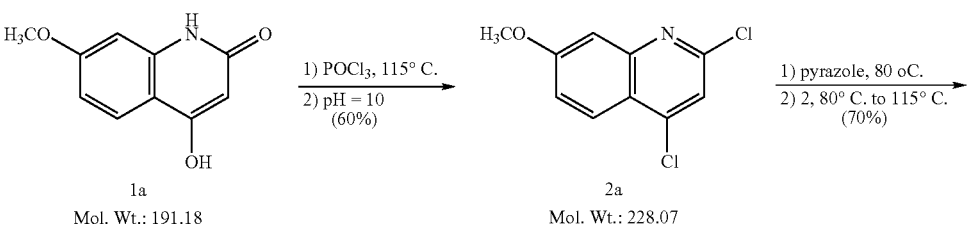

-continued
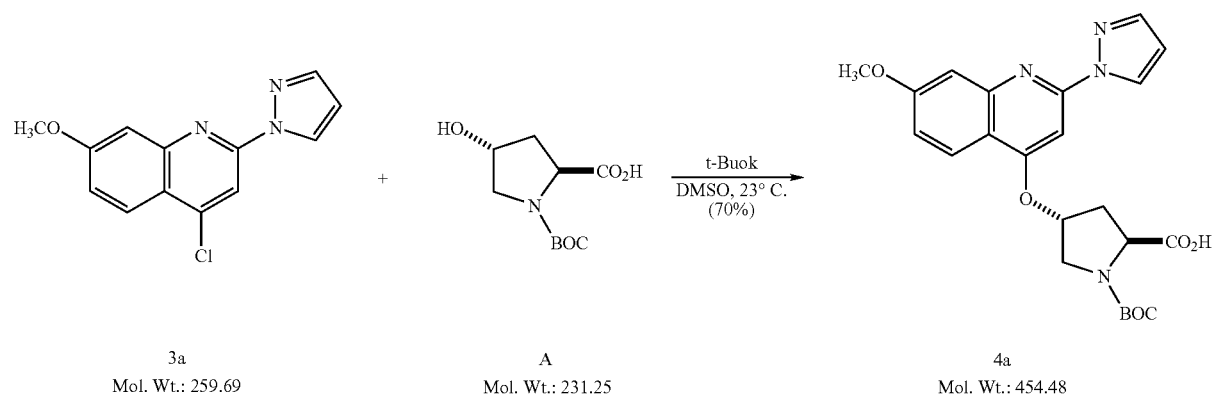
3a
Mol. Wt.: 259.69
A
Mol. Wt.: 231.25
4a
Mol. Wt.: 454.48
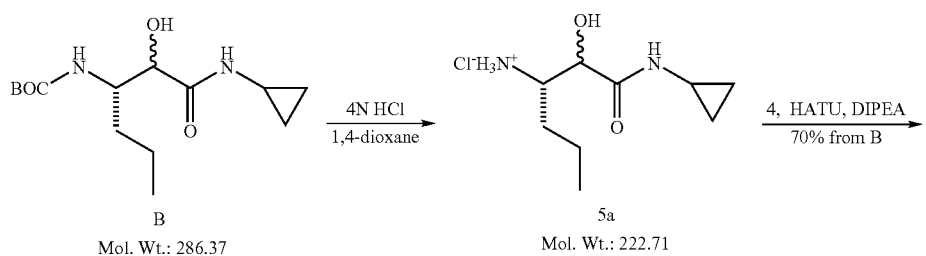
B
Mol. Wt.: 286.37
5a
Mol. Wt.: 222.71
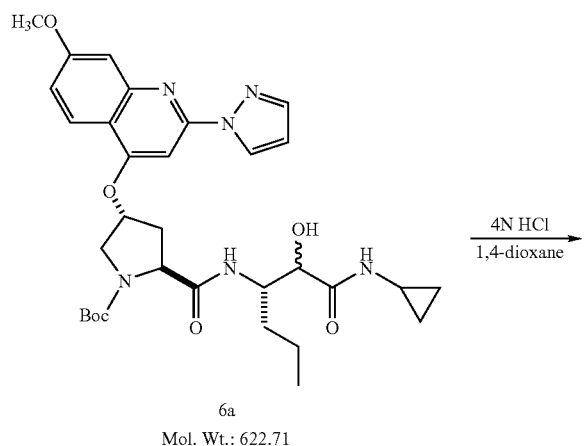
6a
Mol. Wt.: 622.71
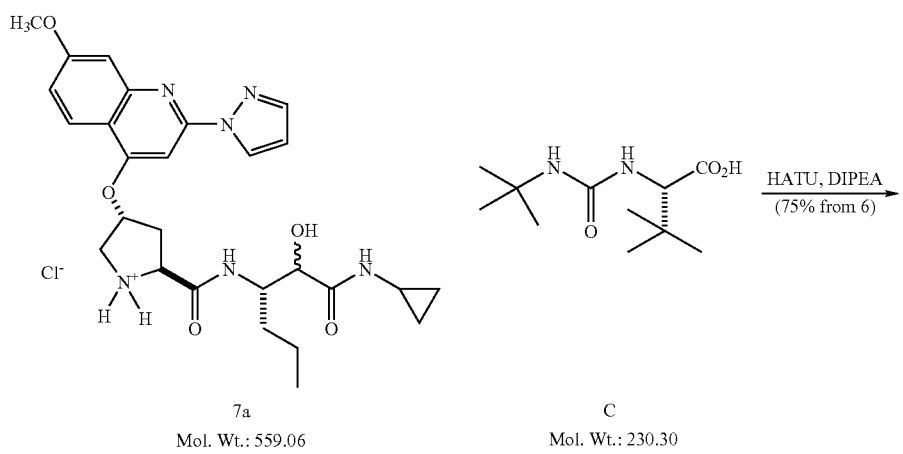
7a
Mol. Wt.: 559.06
C
Mol. Wt.: 230.30

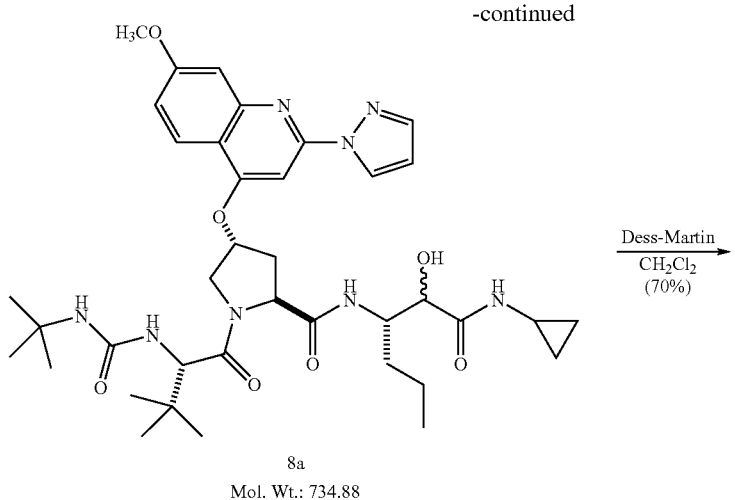

8a
Mol. Wt.: 734.88

Dess-Martin
CH₂Cl₂
(70%)

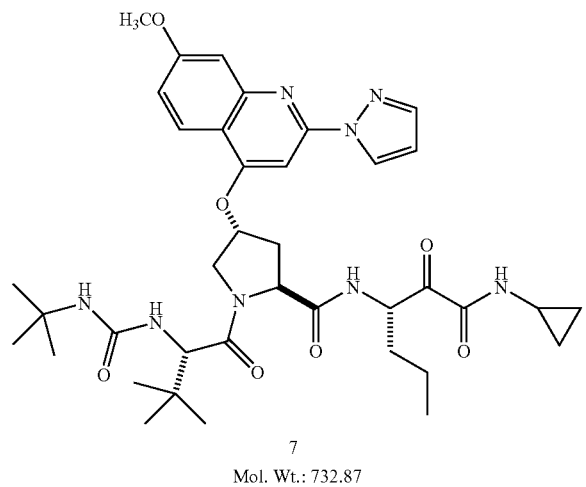

7
Mol. Wt.: 732.87

Step 1

A suspension of 4-hydroxy-7-methoxy-2-oxo-1,2-dihydroquinoline (Faber K. et al., *J. Heterocyclic chem.*, 1985 22, 1080) (5.0 g, 26.17 mmol) in POCl₃ (25 mL, 261.7 mmol) was heated at 115° C. for 3 h (clear solution obtained upon heating). After 3 h, the reaction mixture was concentrated under reduced pressure. The residue was poured into iced water (40 mL), pH was then adjusted to 10 with 3 N NaOH and extracted with CHCl₃ (3×100 mL). The combined CHCl₃ layers were washed with brine and dried (MgSO₄). The organic layer was then filtered and concentrated to give 2,4-Dichloro-7-methoxy-quinoline (4.9 g, 21.49 mmol, 82% yield) as brown solid. MS m/z 229 (M⁺+H).

Step 2

Solid pyrazole (3.2 g, 47.36 mmol, 3.0 equiv.) was heated and melted at 80° C. Then solid 2,4-Dichloro-7-methoxy-quinoline (3.6 g, 15.78 mmol, 1.0 equiv.) was added and the mixture was then heated to 115 fo 3 h. Then the mixture was cooled to rt and purified by flash chromatography (20% ethyl acetate/hexane) to give 4-Chloro-7-methoxy-2-pyrazol-1-yl-quinoline (2.3 g, 8.88 mmol, 56% yield) as white solid. ¹H NMR (CDCl₃): 8.77 (d, 1H, J=2.8 Hz); 8.18 (s, 1.14); 8.10 (d, 1H, J=9.2 Hz); 7.79 (s, 1H); 7.38 (d, 1H, J=2.8 Hz); 7.23 (dd, 1H, J=2.0, 8.8 Hz); 6.53-6.52 (m, 1H); 3.98 (s, 3H). MS m/z 260 (M⁺+H).

Step 3

To commercially available N-t-Boc-(2S,4R)-hydroxyproline (1.53 g, 6.64 mmol) in DMSO (20 mL), potassium tert-butoxide (1.9 g, 16.6 mmol) was added in small portions, over 15 min at 23° C. The mixture was stirred at 23° C. for 1.5 h and then 4-Chloro-7-methoxy-2-pyrazol-1-yl-quinoline (1.9 g, 7.30 mmol) was added in small portions over 15 min. The reaction mixture was stirred at 23° C. for 16 h. The resulting suspension was poured into water (150 mL) and the mixture was washed with ethylacetate (2×100 mL). The aqueous layer was acidified with aqueous 1N HCl to pH ~4 and extracted with CHCl₃ (3×100 mL). The combined CHCl₃ layers were washed with brine and dried (MgSO₄). The organic layer was then filtered, and concentrated to give (2S,4R)-(7-Methoxy-2-pyrazol-1-yl-quinolin-4-yloxy)-pyrrolidine-1,2-dicarboxylic acid 1-tent-butyl ester (2.7 g, 5.95 mmol, 90% yield). MS m/z 455 (M⁺+H), 453 (M⁺-H), 355 (M⁺-Boc). This material was used in the next step as crude without further purification.

Step 4

To [1S-(Cyclopropylcarbamoyl-hydroxy-methyl)-butyl]-carbamic acid tert-butyl ester (1.05 g, 3.67 mmol) was added 4.0 M HCl in dioxane (13 mL). After 1 h, the reaction mixture was concentrated and dried to give the corresponding HCl salt as a white solid. To the above amine HCl salt in DCM/DMF (3:1, 60 mL) was added (2S,4R)-(7-Methoxy-2-pyrazol-1-yl-quinolin-4-yloxy)-pyrrolidine-1,2-dicarboxylic acid 1-tert-butyl ester (1.66 g, 3.67 mmol), HATU (1.67 g, 4.40 mmol) and DIPEA (2.6 mL, 14.08 mmol). After 1 h at rt, the reaction mixture was diluted with ethyl acetate (100 mL) and washed with 1N HCl (2×50 mL), NaHCO₃ (1×100 mL) and brine (1×). The ethyl acetate layer was dried (MgSO₄), filtered and evaporated to dryness to give 2S-[1S-(Cyclopropylcarbamoyl-hydroxy-methyl)-butylcarbamoyl]-4R-(7-methoxy-2-pyrazol-1-yl-quinolin-4-yloxy)-pyrrolidine-1-carboxylic acid tert-butyl ester as mixture of diastereomers. This material was used in the next step as crude without further purification.

Step 5

To the above compound was added 4.0 M HCl in dioxane (15 mL). After 1 h, the reaction mixture was concentrated and dried to give the corresponding HCl salt as a white solid. To the above amine HCl salt in DCM/DMF (3:1, 60 mL) was added 2S-(3-tert-Butyl-ureido)-3,3-dimethyl-butyric acid (848 mg, 3.67 mmol), HATU (1.67 g, 4.40 mmol) and DIPEA (2.6 mL, 14.08 mmol). After 1 h at rt, the reaction mixture was diluted with ethyl acetate (100 mL) and washed with 1N HCl (2×50 mL), NaHCO$_3$ (1×100 mL), and brine (1×). The ethyl acetate layer was dried (MgSO$_4$), filtered and evaporated to dryness. This material was used in the next step as crude without further purification.

Step 6

The above crude product was then dissolved in dry DCM (25 mL) and Dess-Martin periodinane (2.0 g, 4.71 mmol) was added. After stirring at rt for 1 h reaction mixture was quenched with 0.26 M Na$_2$S$_2$O$_3$ in saturated NaHCO$_3$ and extracted with DCM (3×). The combined DCM layers were then washed with saturated NaHCO$_3$ (2×), brine (1×) and dried (MgSO$_4$). The organic layer was then filtered, concentrated and purified by flash chromatography (60% ethyl acetate/hexane) to give 1-[2S-(3-tert-Butyl-ureido)-3,3-dimethyl-butyryl]-4R-(7-methoxy-2-pyrazol-1-yl-quinolin-4-yloxy)pyrrolidine-2S-carboxylic acid (1S-cyclopropylaminooxalyl-butyl)-amide (7) (1.6 g, 2.18 mmol, 60% yield) as white solid. $^1$H NMR: (DMSO-d$_6$) 8.76-8.70 (m, 2H); 8.22 (d, J=6.8 Hz, 1H); 8.11 (d, J=9.6 Hz, 1H); 7.87 (d, J=1.2 Hz, 1H); 7.45 (s, 1H); 7.27 (d, J=2.4 Hz, 1H); 7.00-6.97 (dd, J=2.8 and 9.6 Hz, 1H); 6.64-6.62 (m, 1H); 5.92 (brs, 1H); 5.49 (brs, 1H); 5.00-4.96 (m, 1H); 4.55-4.49 (m, 2H); 4.18 (d, J=5.6 Hz, 1H); 3.90 (s, 3H); 3.91-3.82 (m, 1H); 3.54 (brs, 1H); 2.75-2.72 (m, 1H); 2.54-2.51 (m, 1H); 2.17-2.14 (m, 1H); 1.69-1.66 (m, 1H); 1.40-1.34 (m, 3H); 1.13 (m, 9H); 0.93 (m, 9H); 0.90-0.82 (m, 3H); 0.65-0.53 (m, 4H). MS m/z 733 (M$^+$+H), 755 (M$^+$+Na), 731 (M$^+$−H).

Biological Examples

Example 1

HCV Replicon Assay

The HCV replicon assay is a cell-culture system that mimics in vivo HCV replication and provides a system to study HCV replication in vitro. It was created by transfecting cloned viral RNA derived from a consensus HCV genomic sequence into human Huh7 hepatoma cells that are semi-permissive for viral RNA production (Lohmann V., Korner F., Koch J.-O., Herian U., Theilmann L. and Bartenschlager R. (1999). *Replication of subgenomic Hepatitis C virus RNAs in a hepatoma cell line*. Science 285, 110-113 and Blight K. J., Kolykhalov A. A. and Rice C. M. (2000). *Efficient initiation of HCV RNA Replication in cell culture*. Science 290, 972-1974). These transfected cell lines contain a subgenomic HCV RNA genome that includes (1) the HCV 5'NTR fused to 12 amino acids of the capsid coding region, (2) the neomycin phosphotransferase gene (Neo) as a selectable marker, (3) the internal ribosome entry site (IRES) from encephalomyocarditis virus (EMCV) that directs translation of HCV non-structural proteins (variously NS2 or NS3 to NS5B), and (4) the 3' NTR. Replicon-containing cells autonomously and persistently replicate HCV RNA that can be measured quantitatively by real-time qPCR. Therefore, the replicon system facilitates quantitative assessment of anti-viral activity by monitoring changes in HCV RNA replication in a cell-based assay.

HCV replicon-containing cells (Huh7/Clone A) were routinely maintained in Clone A growth medium (DMEM medium [Invitrogen], supplemented with 10% Fetal Bovine Serum, 1% Non Essential Amino Acids and 1 g/L G418). Test compounds were dissolved in dimethyl sulfoxide (DMSO) to make 200× stock solutions for all doses prior to treatment.

For the HCV replicon assay, Huh7/Clone A cells were trypsinized from culture flasks, seeded in 1 ml of Clone A growth medium without G418 at 4×10$^4$ cells per well in 24-well plates and incubated at 37° C. in a humidified CO$_2$ (5%) incubator overnight. Following overnight incubation, compound solutions were added into wells in the same volume (5 μl of 200× compound stock per well) to give a final DMSO concentration of 0.5%. Three wells on each plate supplemented with 5 μl of DMSO served as untreated controls. For IC$_{50}$ determinations, compounds were tested at 7 serial dilutions in triplicates from the starting stock solutions. The plates were incubated at 37° C. for 48 hours. After incubation, cells were harvested, transferred to 96-well plates, and subjected to total RNA extraction using the RNA Isolation Kit (RNeasy 96, Qiagen) according to the protocol described by the manufacture's RNeasy 96 Handbook (Qiagen).

Total RNA eluted in 130 μl of RNase-free dH$_2$O was quantitated by the RiboGreen Assay according to the supplier's protocol (Molecular Probe). Briefly, 5 μl of RNA samples were aliquoted in duplicate to a 96-well black microplate and a 96-well TaqMan Optical plate. RNA samples in the black microplate were mixed with 95 μl of diluted RiboGreen reagent (1:250 dilution in TE buffer) and sample fluorescence was measured using a fluorescence microplate reader at standard fluorescein wavelengths (excitation ~480 nm, emission ~520 nm). Ribosomal RNA (Molecular Probe) was used as standard.

TaqMan quantitative PCR (RT-qPCR) was used to quantitate the amount of HCV replicon RNA in each sample. The RT-qPCR reactions were performed in 25 μl on an ABI PRISM 7900 HT Sequence Detection System (Applied Biosystems). The reaction mixture contained 5 μl of total RNA (10-100 ng), 1×TaqMan Buffer A (Applied Biosystems), 5.5 mM MgCl$_2$, 1.2 mM dNTP mix, 0.625 U of AmpliTaq Gold (Applied Biosystems), 5 U of MMLV reverse transcriptase (Promega), 5 U of rRNasin (Promega), 300 nM each of the forward and reverse primers, and 100 nM TaqMan MGB probe. Primers and probe were designed to hybridize to a portion of the neomycin resistance gene (neo) in the replicon and the sequences are as follows: forward primer 5'-GGCTACCTGCCCATTCGA-3' (SEQ ID NO: 1); reverse primer 5'-CCGGCTTCCATCCGAGTAC-3' (SEQ ID NO:2); MGB probe 5'-CCACCAAGCGAAACA-3' (SEQ ID NO:3). The RT step was performed at 48° C. for 30 min, followed by 10 min at 95° C. The thermal cycling program consisted of 40 cycles of 15 s at 95° C. and 1 min at 60° C. TaqMan raw data (Ct values) were analyzed using the Sequence Detection System (SDS) software, mathematically converted to HCV RNA genome amount and normalized to total RNA in each sample. The sample without compound treatment served as a control and the HCV replicon RNA level from untreated cells was defined as 100%. Compound inhibitory activity was determined as the ratio of the normalized HCV RNA amount in treated samples relative to the untreated control. Compound IC$_{50}$s were calculated using a standard 4 parameter curve fit model.

Compounds of the invention were tested by the above-described assay and observed to inhibit HCV replication with $IC_{50}$'s<100 micromolar. Compounds 3, 6 and 7 inhibited HCV replication with $IC_{50}$'s<50 micromolar; while compounds 1, 2, 5, 8-13 and 15 inhibited HCV replication with $IC_{50}$'s<10 micromolar.

Example 1

Representative pharmaceutical formulations containing a Compound of Formula (I)

Oral Formulation

| | |
|---|---|
| Compound of Formula (I) | 10-100 mg |
| Citric Acid Monohydrate | 105 mg |
| Sodium Hydroxide | 18 mg |
| Flavoring | |
| Water | q.s. to 100 mL |

Intravenous Formulation

| | |
|---|---|
| Compound of Formula (I) | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

Tablet Formulation

| | |
|---|---|
| Compound of Formula (I) | 1% |
| Microcrystalline Cellulose | 73% |
| Stearic Acid | 25% |
| Colloidal Silica | 1% |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A compound of Formula (I):

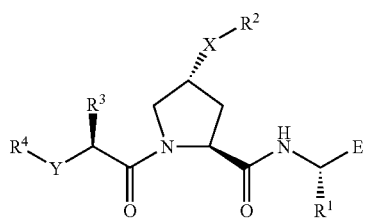

wherein
E is —COCONR$^5$R$^6$, where R$^5$ and R$^6$ are each independently selected from hydrogen, alkyl, cycloalkyl, cycloalkylalkyl, aryl, aralkyl, heteroaryl, heteroaralkyl, heterocyclyl, or heterocyclylalkyl;
R$^1$ is alkyl, haloalkyl, cycloalkyl, or cycloalkylalkyl;
X is —O—;
R$^3$ is alkyl, haloalkyl, cycloalkyl, or cycloalkylalkyl;
Y is —OC(O)NH—, —NR$^{14}$—C(O)NH—, or —NR$^{14}$C(O)O— where each R$^{14}$ is selected from hydrogen or alkyl;
R$^2$ is a group of formula (b):

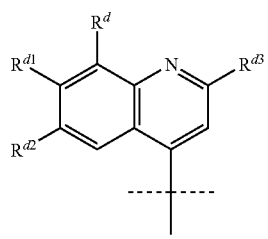

where:
R$^{d1}$ is hydrogen, hydroxy, or alkoxy;
R$^d$ and R$^{d2}$ are independently hydrogen, alkyl, halo, or alkoxy;
R$^{d3}$ is hydrogen, alkyl, cycloalkyl, or cycloalkylalkyl; and
R$^4$ is alkyl; or
a pharmaceutically acceptable salt thereof.

2. The compound of claim 1 wherein R$^{d3}$ is hydrogen, methyl, ethyl, n-propyl, i-propyl, n-butyl, 1-methylpropyl, 2-methylpropyl, tert-butyl, 2,2,dimethylpropyl, 1,2-dimethylpropyl, 1,2,2-trimethylpropyl, cyclopropyl, cyclobutyl, cyclopentyl, cyclohexyl, cyclopropylmethyl, cyclobutylmethyl, cyclopentylmethyl or cyclohexylmethyl.

3. The compound of claim 1 wherein R$^{d1}$ is hydrogen, hydroxy, or alkoxy; R$^d$ and R$^{d2}$ are independently hydrogen, alkyl, halo, or alkoxy; and R$^{d3}$ is a hydrogen, alkyl or cycloalkyl.

4. The compound of claim 3 wherein R$^{d1}$ is hydrogen, hydroxy, methoxy, ethoxy, n-propoxy, or iso-propoxy; R$^d$ and R$^{d2}$ are independently, fluoro, chloro, methyl, ethyl, methoxy, or ethoxy.

5. The compound of claim 3 wherein R$^{d1}$ is hydrogen, hydroxy, methoxy, or ethoxy; R$^d$ and R$^{d2}$ are independently, hydrogen, fluoro, chloro or methyl.

6. The compound of claim 5 wherein R$^{d1}$ is methoxy or ethoxy; and R$^d$, R$^{d2}$ and R$^{d3}$ are each hydrogen.

7. The compound of claim 1 wherein X is —O—; R$^1$ is alkyl or cycloalkylalkyl; and R$^3$ is 1-methylethyl, 1-methylpropyl, tert-butyl, cyclopropyl, or cyclohexyl.

8. The compound of claim 7 wherein X is —O—; R$^1$ is cyclobutylmethyl, ethyl, or n-propyl; and R$^3$ is tert-butyl or cyclohexyl.

9. The compound of claim 1 wherein E is —COCONHR$^6$ where R$^6$ is hydrogen, alkyl, cycloalkyl, aralkyl, or heteroaralkyl.

10. The compound of claim 1 wherein E is —COCONHR$^6$ where R$^6$ is cyclopropyl.

11. The compound of claim 1 wherein Y is —NHC(O)NH— and R$^4$ is alkyl.

12. The compound of claim 1 wherein Y is —OC(O)NH— and R$^4$ is alkyl.

13. The compound of claim 1, wherein the compound has the following structure:

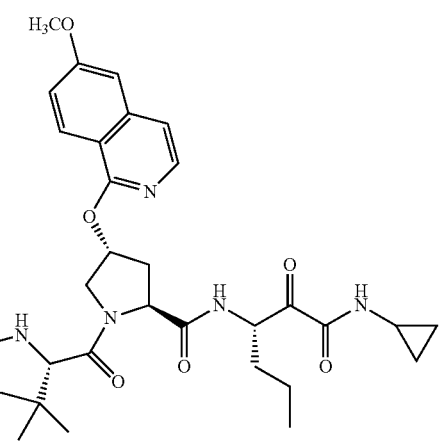

or a pharmaceutically acceptable salt thereof.

14. The compound of claim 1, wherein the compound has the following structure:

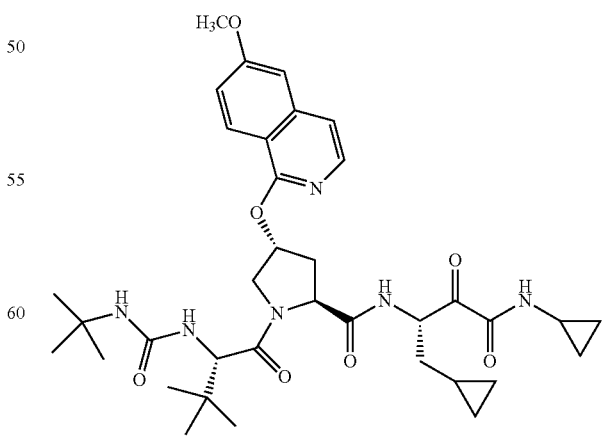

or a pharmaceutically acceptable salt thereof.

15. The compound of claim 1, wherein the compound has the following structure:

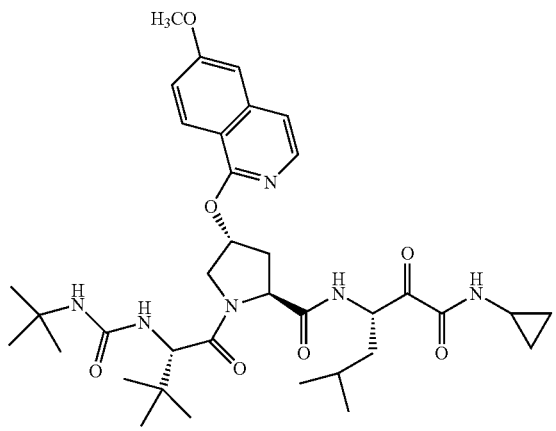 [SMILES: COc1ccc2c(O[C@@H]3C[C@@H](C(=O)N[C@@H](CC(C)C)C(=O)C(=O)NC4CC4)N(C(=O)[C@@H](NC(=O)NC(C)(C)C)C(C)(C)C)C3)nccc2c1]

or a pharmaceutically acceptable salt thereof.

16. The compound of claim 1, wherein the compound has the following structure:

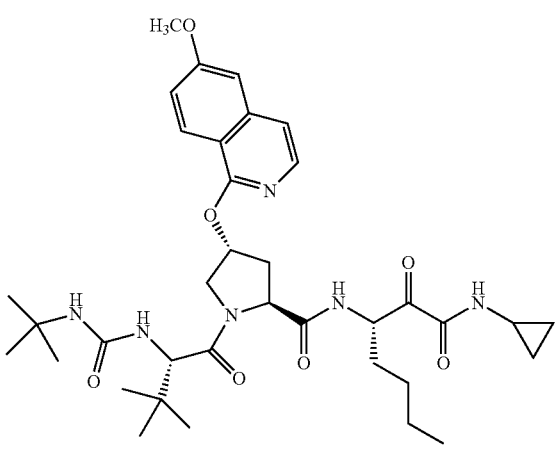 [SMILES: CCCC[C@H](NC(=O)[C@@H]1C[C@@H](Oc2nccc3cc(OC)ccc23)CN1C(=O)[C@@H](NC(=O)NC(C)(C)C)C(C)(C)C)C(=O)C(=O)NC1CC1]

or a pharmaceutically acceptable salt thereof.

17. The compound of claim 1, wherein the compound has the following structure:

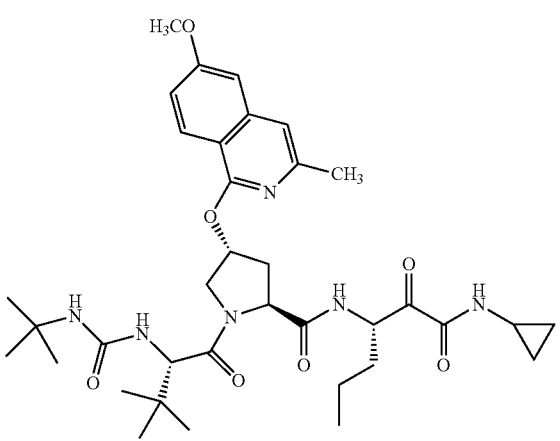 [SMILES: CCC[C@H](NC(=O)[C@@H]1C[C@@H](Oc2nc(C)cc3cc(OC)ccc23)CN1C(=O)[C@@H](NC(=O)NC(C)(C)C)C(C)(C)C)C(=O)C(=O)NC1CC1]

or a pharmaceutically acceptable salt thereof.

18. The compound of claim 1, wherein the compound has the following structure:

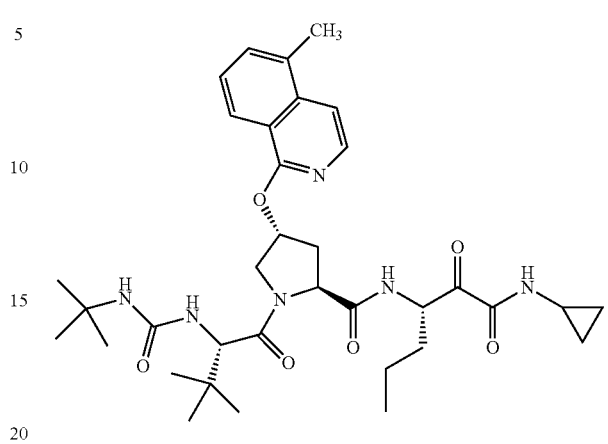

or a pharmaceutically acceptable salt thereof.

19. The compound of claim 1, wherein the compound has the following structure:

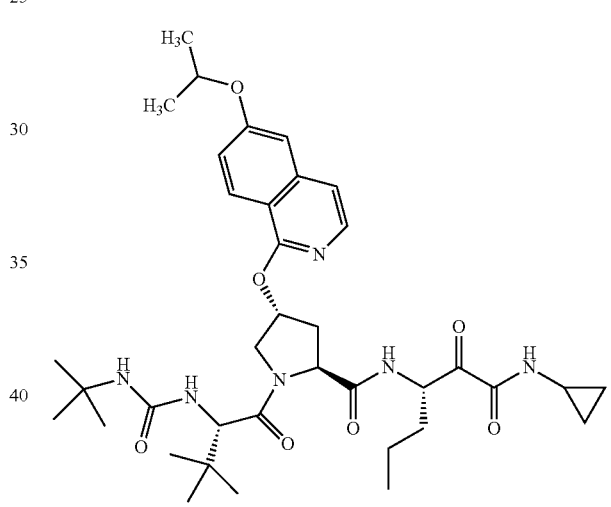

or a pharmaceutically acceptable salt thereof.

20. The compound of claim 1, wherein the compound has the following structure:

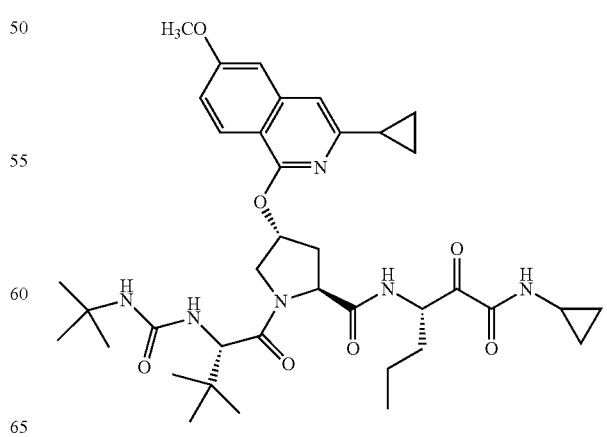

or a pharmaceutically acceptable salt thereof.

21. The compound of claim 1, wherein the compound is selected from the group consisting of:
- 1-[2S-(3-tert-Butyl-ureido)-3,3-dimethyl-butyryl]-4R-(6-methoxy-isoquinolin-yloxy)-pyrrolidine-2S-carboxylic acid (1S-cyclopropylaminooxalyl-butyl)-amide;
- 1-[2S-(3-tert-Butyl-ureido)-3,3-dimethyl-butyryl]-4R-(6-methoxy-isoquinolin-1-yloxy)-pyrrolidine-2S-carboxylic acid (2-cyclopropylcarbamoyl-1S-cyclopropylmethyl-2-oxo-ethyl)-amide;
- 1-[2S-(3-tert-Butyl-ureido)-3,3-dimethyl-butyryl]-4R-(6-ethoxy-isoquinolin-yloxy)-pyrrolidine-2-carboxylic acid (2-cyclopropylcarbamoyl-1S-cyclopropylmethyl-2S-oxo-ethyl)-amide;
- 1-[2S-(3-tert-Butyl-ureido)-3,3-dimethyl-butyryl]-4R-(6-ethoxy-isoquinolin-1-yloxy)-pyrrolidine-2S-carboxylic acid (1S-cyclopropylaminooxalyl-butyl)-amide; and
- 1-[2S-(3-tert-Butyl-ureido)-3,3-dimethyl-butyryl]-4R-(6-methoxy-isoquinolin-1-yloxy)-pyrrolidine-2S-carboxylic acid (1S-cyclopropylaminooxalyl-pentyl)-amide.

22. A pharmaceutical composition comprising a compound of any one of the claims 1-9, 10-17, and 18-21 and one or more pharmaceutically acceptable excipients.

23. A method of treating hepatitis C infections in a patient comprising administering to the patient a pharmaceutical composition comprising a compound of any one of the claims 1-9, 10-17, and 18-21 and one or more pharmaceutically acceptable excipients.

24. The compound of any one of claims 1-9, 10-17, and 18-21; or a pharmaceutically acceptable sulfate or sulfonate salt thereof.

25. The pharmaceutical composition of claim 22, further comprising a second antiviral agent.

26. The pharmaceutical composition of claim 25, wherein said second antiviral agent is Ribavirin or a polymerase inhibitor.

27. A method of treating HCV infections in a patient comprising administering to said patient a compound of any of claims 1-9, 10-17, and 18-21 or a pharmaceutical composition comprising a compound of claim 1 and a second antiviral agent selected from the group consisting of interferon, pegylated or unpegylated congeners of interferon, Ribavirin, a HCV polymerase inhibitor and a toll receptor agonist.

28. A compound of Formula (I):

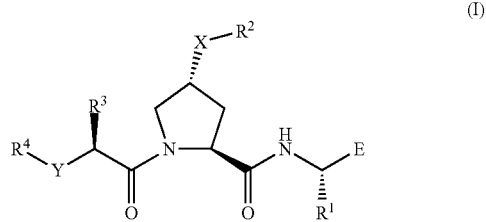

wherein
E is —COCONHR$^6$ where R$^6$ is cyclopropyl;
R$^1$ is cyclobutylmethyl, ethyl, or n-propyl;
X is —O—;
R$^3$ is tert-butyl;
Y is —NHC(O)NH—;
R$^2$ is heteroaryl optionally substituted with one or two substituents independently selected from alkoxy and haloalkyl; and
R$^4$ is alkyl; or
a pharmaceutically acceptable salt thereof.

* * * * *

SEQUENCE LISTING

```
<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: TaqMan quantitative PCR (RT-qPCR) hepatitis C
      virus (HCV) replicon neomycin resistance gene (neo) forward primer

<400> SEQUENCE: 1
ggctacctgc ccattcga                                                   18

<210> SEQ ID NO 2
<211> LENGTH: 19
<212> TYPE: DNA
<213> ORGANISM: Artificial Sequence
<220> FEATURE:
<223> OTHER INFORMATION: TaqMan quantitative PCR (RT-qPCR) hepatitis C
      virus (HCV) replicon neomycin resistance gene(neo) reverse primer

<400> SEQUENCE: 2
ccggcttcca tccgagtac                                                  19

<210> SEQ ID NO 3
<211> LENGTH: 15
<212> TYPE: DNA
<213> ORGANISM: Artificial Sequence
<220> FEATURE:
<223> OTHER INFORMATION: TaqMan quantitative PCR (RT-qPCR) hepatitis C
      virus (HCV) replicon neomycin resistance gene(neo) TaqMan MGB
      probe

<400> SEQUENCE: 3
ccaccaagcg aaaca                                                      15
```